United States Patent [19]

Van Toan et al.

[11] Patent Number: 5,538,840
[45] Date of Patent: Jul. 23, 1996

[54] PHOTOGRAPHIC RECORDING MATERIAL CONTAINING A UV ABSORBER

[75] Inventors: Vien Van Toan, Lentigny; David G. Leppard, Marly; Gerhard Rytz, Bern; Norbert Würms, St. Ursen; Pascal Hayoz, Villars-sur-Glâne, all of Switzerland

[73] Assignee: Ciba-Geigy Corporation, Tarrytown, N.Y.

[21] Appl. No.: 538,090

[22] Filed: Oct. 2, 1995

[30] Foreign Application Priority Data

Oct. 4, 1994 [CH] Switzerland ............... 2988/94
Oct. 10, 1994 [CH] Switzerland ............... 3039/94
Feb. 8, 1995 [CH] Switzerland ............... 364/95
Feb. 8, 1995 [CH] Switzerland ............... 365/95

[51] Int. Cl.$^6$ ................................. G03C 1/815
[52] U.S. Cl. .............................. 430/5.2; 430/507
[58] Field of Search ........................ 430/507, 512

[56] References Cited

U.S. PATENT DOCUMENTS

| | | | |
|---|---|---|---|
| 3,423,360 | 1/1969 | Huber et al. | 260/47 |
| 3,843,371 | 10/1974 | Piller et al. | 96/84 R |
| 4,551,420 | 11/1985 | Sugimoto et al. | 430/512 |
| 5,189,084 | 2/1993 | Birbaum et al. | 524/100 |
| 5,300,414 | 4/1994 | Leppard et al. | 430/512 |
| 5,364,749 | 11/1994 | Leppard et al. | 430/512 |
| 5,384,235 | 1/1995 | Chen et al. | 430/512 |

FOREIGN PATENT DOCUMENTS

| | | |
|---|---|---|
| 0434608 | 6/1991 | European Pat. Off. . |
| 0530135 | 3/1993 | European Pat. Off. . |
| 0577122 | 1/1994 | European Pat. Off. . |
| 4340725 | 6/1994 | Germany . |
| 481954 | 1/1970 | Switzerland . |
| 2273498 | 6/1994 | United Kingdom . |

OTHER PUBLICATIONS

Derwent Abstract 93–069133 of EP 0,530,135.
Derwent Abstract 83–711952 of CH 481,954.
Derwent Abstract CA72:122267 of CH 481,954.
Chem. Abst. 119:213920n of EP 0530,135.

*Primary Examiner*—Lee C. Wright
*Attorney, Agent, or Firm*—Michele A. Kovaleski

[57] ABSTRACT

The invention relates to a photographic recording material comprising, on a base, at least one silver-halide emulsion layer and, if desired, at least one interlayer and/or a protection layer, where at least one of said layers contains a UV absorber of the 2-hydroxyphenyltriazine type, as described in greater detail in claim 1; this UV absorber can also be in the form of a homopolymer or copolymer.

17 Claims, No Drawings

PHOTOGRAPHIC RECORDING MATERIAL CONTAINING A UV ABSORBER

The present invention relates to a novel photographic recording material which contains a UV absorber of the 2-hydroxyphenyltriazinyl type.

Photographic recording materials are typically based on silver-halide emulsions, where the silver-halide and, in the case of colour-photographic materials, also the dyes or dye precursors are sensitive to UV radiation. In particular, UV radiation having a wavelength of from 300 to 400 nm modifies, discolours or bleaches the material. This sensitivity to UV radiation is undesired. These effects can be suppressed in full or part by adding stabilizers typically UV absorbers with an absorption maximum of from 300 to 400 nm, to the cyan, magenta and yellow dyes and to the couplers; known examples of these stabilizers are compounds from the 2-hydroxyphenylbenzotriazole class.

However, the use of the UV absorbers (UVAs) known hitherto frequently results in undesired effects, for example discoloration and/or spotting as a consequence of inadequate inherent stability to light, heat or moisture. Furthermore, the high-boiling organic solvent used to prepare the UVA emulsion can cause softening of the layer and impaired adhesion between the various layers. Compensation for this effect by increasing the gelatin content generally only results in destabilization of the layer, while an additional gelatin protective layer over the UVA-containing layers causes an undesired increase in the overall layer thickness. Other disadvantages of conventional UVA systems can be migration, surface crystallization or blooming, caking and light scattering at oversized oil droplets which contain the UVA and are prepared by known emulsification methods.

It is known that polymer lattices prepared by polymerization of certain UV monomers can provide a partial solution to the abovementioned problems, as discussed, for example, in EP-A-0 577 122 for polymeric 2-hydroxyphenylbenzotriazoles.

It has also already been proposed (EP-A-0 530 135, U.S. Pat. No. 5,364,749, U.S. Pat. No. 5,300,414) to use some UV absorbers of the 2-hydroxyphenyltriazine type in photographic materials. Other compounds of this type are described, for example, in EP-A-0 434 608 and U.S. Pat. No. 5,189,084.

A specific group of 2-hydroxyphenyltriazine UV absorbers has now been found whose use for the stabilization of photographic recording materials surprisingly has none of said disadvantages and which have improved inherent stability to light and which, furthermore, are suitable for increasing the stability of the cyan, magenta and yellow layers in photographic materials. The novel photographic materials offer the advantage over known materials stabilized using hydrophenyltriazine UV absorbers (for example U.S. Pat. No. 5,364,749) of, for example, a paler yellow coloration without impairment of the light-protection action.

The novel UV absorbers can be used for silver-halide-containing recording materials of all types. For example, they can be employed for colour paper, colour reversal paper, direct-positive colour material, colour negative film, colour positive film, colour reversal film, etc. They are preferably used, inter alia, for photosensitive colour material which has a reversal substrate or forms positives.

These triazines can furthermore advantageously be combined with UV absorbers of the hydroxyphenylbenzotriazole type, in particular representatives thereof which are liquid at room temperature (cf., for example, U.S. Pat. No. 4,853,471, 4,973,702, 4,921,966 and U.S. Pat. No. 4,973,701).

Combinations of the hydroxyphenyltriazines with UV absorbers of other types, such as benzophenones, oxanilides, cyanoacrylates, salicylates, acrylonitriles or thiazolines, are also suitable for use in photographic recording materials.

The present application thus relates to a photographic recording material comprising, on a base, at least one silver-halide emulsion layer and, if desired, at least one interlayer and/or a protection layer, where at least one of said layers contains a UV absorber, wherein said UV absorber is a homopolymer obtained by addition polymerization of a monomer of the formula I, a copolymer of at least two different compounds of the formula I, or a copolymer of at least one compound of the formula I and at least one further ethylenically unsaturated compound

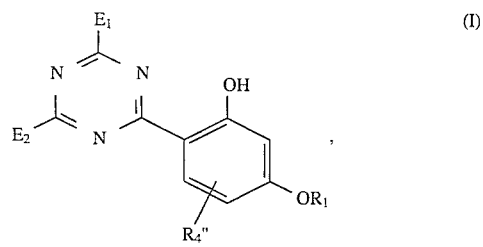

in which $E_1$ and $E_2$, independently of one another, are each a group of the formula Ia or Ib

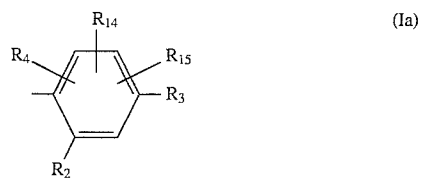

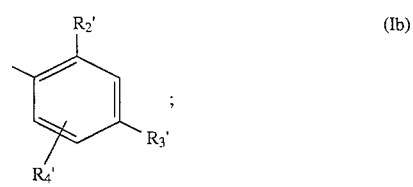

$R_1$, independently of one another, are —A, —CH$_2$—CH(XA)—CH$_2$—O—R$_7$, —CR$_8$R'$_8$ —(CH$_2$)$_l$—XA, —CH$_2$—CH(OA)—R$_9$, —CH$_2$—CH(OH)—CH$_2$—XA,

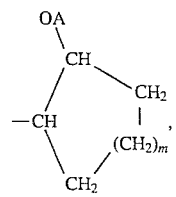

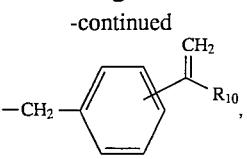

—CH$_2$—C(=CH$_2$)—R$_{10}$, —(CH$_2$)$_p$—SiR$_{11}$R$_{11}$'—CH=CH$_2$, —C(=O)—(CH$_2$)$_q$—CH=CH$_2$, —CHR$_8$—(CH$_2$)$_r$—C(=O)—O—CH$_2$—CH(OH)—CH$_2$—OA, —CR$_8$R'$_8$—(CH$_2$)$_l$—C(=O)—XA or —C(=O)—O—CH$_2$—C(=CH$_2$)—R$_{10}$;

A is —C(=O)—CR$_5$=CH—R$_6$;

R$_2$, independently of one another, are H, C$_1$–C$_{12}$alkyl, C$_5$–C$_{12}$cycloalkyl, C$_3$–C$_6$ alkenyl, halogen, phenyl or trifluoromethyl;

R$_2$', independently of one another, are C$_1$–C$_{18}$alkoxy, C$_3$–C$_{18}$alkenoxy, —O—CO—R$_{12}$, —OH or —OA;

R$_3$ and R$_3$', independently of one another, are H, —OH, —OR$_1$, —OR$_{131}$, C$_1$–C$_{18}$alkyl, C$_3$–C$_{18}$alkenyl, C$_6$–C$_{12}$cycloalkyl, halogen, trifluoromethyl, phenyl, phenyl-C$_1$–C$_4$alkyl, —CN, C$_1$–C$_{18}$alkyl-S(=O)$_t$— or phenyl-S(=O)$_t$—;

R$_4$, R$_4$' and R$_4$", independently of one another, are H, C$_1$–C$_{18}$alkyl, C$_3$–C$_6$ alkenyl, —OR$_{131}$, halogen, trifluoromethyl, phenyl, phenyl-C$_1$–C$_4$alkyl, mono- to tri-C$_1$–C$_4$alkyl-substituted phenyl-C$_1$–C$_4$alkyl, —CN, C$_1$–C$_{18}$alkyl-S(=O)$_t$— or phenyl-S(=O)$_t$—;

R$_5$ is H, —CH$_2$—COOR$_{13}$, C$_1$–C$_4$alkyl or —CN;

R$_6$ is H, —COOR$_{13}$, C$_1$–C$_{17}$alkyl or phenyl;

R$_7$ is C$_1$–C$_{18}$alkyl, C$_5$–C$_{12}$cycloalkyl, C$_3$–C$_{18}$alkenyl; phenyl; phenyl which is substituted by one to three C$_1$–C$_8$alkyl, C$_1$–C$_8$alkoxy, C$_3$–C$_8$alkenoxy, halogen or trifluoromethyl radicals; phenyl-C$_1$–C$_4$alkyl; C$_3$–C$_{50}$alkyl which is interrupted by one or more —O—; 1-adamantyl; 2-adamantyl; norbornyl; 2-methylnorbornyl, —C(=O)—R$_{12}$ or —A; R$_8$ and R$_8$', independently of one another, are H; C$_1$–C$_{18}$alkyl; phenyl; phenyl which is substituted by one to three C$_1$–C$_8$alkyl, C$_1$–C$_8$alkoxy, C$_3$–C$_8$alkenoxy, halogen or trifluoromethyl radicals; or are phenyl-C$_1$–C$_4$alkyl;

R$_9$ is C$_1$–C$_{18}$alkyl, phenyl or phenyl-C$_1$–C$_4$alkyl;

R$_{10}$ is H or —CH$_3$;

R$_{11}$ and R$_{11}$', independently of one another, are C$_1$–C$_4$alkyl or phenyl or phenyl which is substituted by one to three C$_1$–C$_8$alkyl, C$_1$–C$_8$alkoxy, C$_3$–C$_8$alkenoxy, halogen or trifluoromethyl radicals;

R$_{12}$ is H, C$_1$–C$_{18}$alkyl, phenyl, phenyl-C$_1$–C$_4$alkyl, C$_5$–C$_{12}$cycloalkyl, C$_1$–C$_{12}$alkoxy, phenoxy, norborn-2-yl, 5-norbornen-2-yl or 1-adamantyl;

R$_{13}$ is C$_1$–C$_{18}$alkyl; C$_3$–C$_{18}$alkenyl; phenyl; C$_5$–C$_{12}$cycloalkyl; C$_3$–C$_{50}$ alkyl which is interrupted by one or more —O—; phenyl which is substituted by one to three C$_1$–C$_8$alkyl, C$_1$–C$_8$alkoxy, C$_3$–C$_8$alkenoxy, halogen or trifluoromethyl radicals; phenyl-C$_1$–C$_4$alkyl; 2-adamantyl; norbornyl or 2-methylnorbornyl;

R$_{14}$ and R$_{15}$, independently of one another, are H, C$_1$–C$_{18}$alkyl, C$_3$–C$_{18}$alkenyl, C$_6$–C$_{12}$cycloalkyl, halogen, trifluormethyl, phenyl, phenyl-C$_1$–C$_4$-alkyl, —CN, C$_1$–C$_{18}$alkyl-(S=O)$_t$—, phenyl-(S=O)$_t$— or —OR$_{131}$; R$_{131}$ is C$_1$–C$_{18}$alkyl; C$_1$–C$_{18}$alkyl which is substituted by —OH, C$_1$–C$_{18}$alkoxy, C$_5$–C$_{12}$cycloalkoxy, C$_3$–C$_6$alkenyloxy, halogen, —COOR$_{13}$, —CONH$_2$, —COHNR$_{132}$, —CON(R$_{132}$)(R$_{133}$), —NHCOR$_{12}$, —CN, —OCOR$_{12}$, phenoxy and/or by phenoxy which is substituted by C$_1$–C$_{18}$alkyl, C$_1$–C$_{18}$alkoxy or halogen; or is C$_3$–C$_{18}$alkenyl;

C$_6$–C$_{12}$cycloalkyl; C$_{1–C4}$alkyl- and/or —OCOR$_{12}$-substituted C$_6$–C$_{12}$cycloalkyl; C$_3$–C$_{50}$alkyl which is interrupted by one or more —O—; C$_3$–C$_{50}$alkyl which is interrupted by one or more —O— and substituted by —OA or —O—CO—R$_{12}$; phenyl; phenyl-C$_1$–C$_4$alkyl; —COR$_{12}$ or —SO$_2$R$_{12}$;

R$_{132}$ and R$_{133}$, independently of one another, are C$_1$–C$_{12}$alkyl, C$_3$–C$_{12}$alkoxyalkyl, C$_4$–C$_{16}$dialkylaminoalkyl or C$_5$–C$_{12}$cycloalkyl; or R$_{132}$ and R$_{133}$ together are C$_3$–C$_9$alkylene, C$_3$–C$_9$oxaalkylene or -azaalkylene; X is —NR$_8$, —O—, —NH—(C$_n$H$_{2n}$)—NH— or —O—(C$_k$H$_{2k}$)—NH;

k is a number from 2 to 4;

l is a number from 0 to 19;

m is a number from 2 to 8;

n is a number from 0 to 4;

p is a number from 0 to 10;

q is a number from 1 to 8;

r is a number from 0 to 18; and t is the number 0, 1 or 2.

If monomer units of the formula I contain more than one of the radicals mentioned above, these can be identical or different within the definitions given.

The application furthermore relates to the use of the above compounds for stabilizing photographic recording materials and to a process for stabilizing photographic recording materials by incorporating the above compounds into the materials.

Any substituents in the compounds of the formula (I) which are alkyl having up to 18 carbon atoms are radicals such as methyl, ethyl, propyl, butyl, pentyl, hexyl, heptyl, octyl, nonyl, decyl, undecyl, dodecyl, tetradecyl, hexadecyl or octadecyl, or the corresponding branched isomers.

Any substituents in the compounds of the formula (I) which are alkoxy having up to 18 carbon atoms are radicals such as methoxy or ethoxy, or radicals analogous to the above alkyl radicals.

Any substituents in the compounds of the formula (I) which are alkenyl having up to 18 carbon atoms are radicals such as vinyl, prop-1-enyl (—CH=CH—CH$_3$) or prop-2-enyl (—CH$_2$—CH=CH$_2$), or radicals analogous to the above alkyl radicals.

Any substituents in the compounds of the formula (I) which are alkenoxy having up to 18 carbon atoms are radicals such as ethenoxy, prop-1-enoxy (—O—CH=CH—CH$_3$) or prop-2-enoxy (—O—CH$_2$—CH=CH$_2$), or radicals analogous to the above alkyl radicals.

Any substituents in the compounds of the formula (I) which are phenyl-C$_1$–C$_4$alkyl or mono- to tri-C$_1$–C$_4$alkyl-substituted phenyl-$C_1$-$C_4$alkyl are radicals such as

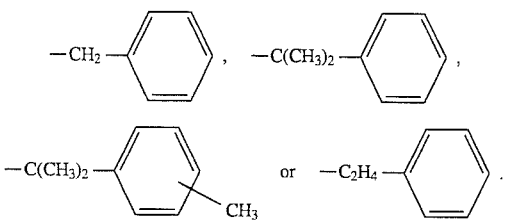

Any substituents in the compounds of the formula (I) which are phenyl-$C_1$-$C_4$alkoxy are radicals such as

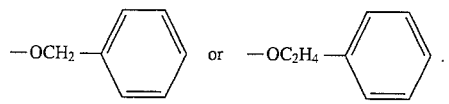

Any substituents in the compounds of the formula (I) which are halogen are fluorine, chlorine, bromine or iodine.

$R_1$ is preferably —A, —$CH_2$—CH(XA)—$CH_2$—O—$R_7$, —$CR_8R'_8$—$(CH_2)_1$—XA, —$CH_2$—CH(OA)—$R_9$, —$CH_2$—CH(OH)—$CH_2$—XA,

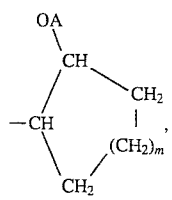

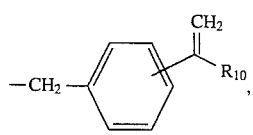

—$CHR_8$—$(CH_2)_r$—C(=O)—O—$CH_2$—CH(OH)—$CH_2$—OA; particularly preferably —A, —$CH_2$—CH(OA)—$CH_2$—O—$R_7$, —$CHR_8$—$(CH_2)_1$—OA, —$CH_2$—CH(OA)—$R_9$, —$CH_2$—CH(OH)—$CH_2$—OA,

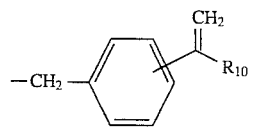

or

—$CHR_8$—$(CH_2)_r$—C(=O)—O—$CH_2$—CH(OH)—$CH_2$—OA; and very particularly preferably —A, —$CH_2$—CH(OA)—$CH_2$—O—$R_7$, —$CHR_8$—$(CH_2)_1$—OA, —$CH_2$—CH(OA)—$R_9$ or

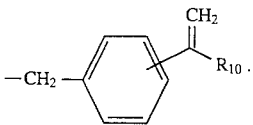

$R_2$ is preferably H, $C_1$-$C_4$alkyl, $C_3$alkenyl, F, Cl or phenyl; particularly preferably H, —$CH_3$ or Cl; and very particularly preferably H or —$CH_3$.

$R_2'$ is preferably H, —OH, $C_1$-$C_4$alkoxy, $C_3$alkenoxy; particularly $C_1$-$C_2$alkoxy or OH.

$R_3$ and $R_3'$ are preferably H, —OH, —$OR_1$, —$OR_{131}$, $C_1$-$C_4$alkyl, cyclohexyl, $C_3$alkenyl, F, Cl, trifluoromethyl, phenyl, benzyl or —CN; particularly preferably H, —OH, —$OR_1$, —$CH_3$, $C_1$-$C_{12}$alkoxy, $C_2$-$C_6$alkanoyloxy-substituted $C_2$-$C_{18}$alkoxy, $C_3$alkenoxy, F, Cl, phenyl, benzoxy or —CN; and very particularly preferably H, —$OR_1$, —$CH_3$, $C_1$-$C_{12}$alkoxy, Cl phenyl or —CN.

Frequently, $R_3'$ is —OH, —$OR_1$ or —$OR_{131}$ and $R_3$ is not —$OR_1$.

$R_4$, $R_4'$ and $R_4''$ are preferably, H, $C_1$-$C_4$alkyl, $C_3$alkenyl, $C_1$-$C_4$ alkoxy, $C_3$alkenoxy, F, Cl, trifluoromethyl, phenyl, phenyl-$C_1$-$C_3$alkyl or —CN; particularly preferably H, —$CH_3$, $C_3$alkenyl, —$OCH_3$, $C_3$alkenoxy, F, Cl, phenyl-$C_3$alkyl or —CN; and very particularly preferably H, —$OCH_3$ or —$CH_3$.

$R_5$ is preferably H or —$CH_3$.

$R_6$ is preferably H, —$COOR_{13}$, —$CH_3$ or phenyl; and particularly preferably H or —$CH_3$.

$R_7$ is preferably $C_1$-$C_8$alkyl, $C_5$-$C_8$cycloalkyl, $C_3$-$C_8$alkenyl, phenyl, phenyl or benzyl which is substituted by one to three $C_1$-$C_4$alkyl or $C_1$-$C_4$alkoxy radicals, and particularly preferably $C_1$-$C_8$alkyl, cyclopentyl, cyclohexyl, $C_3$alkenyl, phenyl or benzyl.

$R_8$ and $R_8'$ are preferably, independently of one another, H or $C_1$-$C_{18}$alkyl.

$R_{10}$ is preferably hydrogen.

$R_{11}$ and $R_{11}'$, independently of one another, are preferably $C_1$-$C_4$alkyl or phenyl, especially methyl.

X is preferably —O— or —$NR_8$—, particularly an oxygen atom.

The value of the index 1 is preferably 1–15.

The UV absorber of the invention can also be a monomer. Accordingly, the invention also pertains to a photographic recording material comprising, on a base, a silver-halide emulsion layer or a silver-halide emulsion layer and additionally an interlayer and/or a protection layer, and containing in a layer a UV absorber, wherein said UV absorber is a compound of the formula I

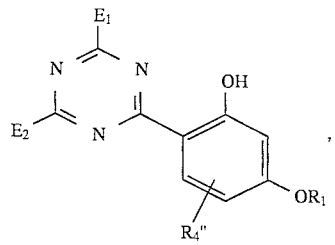

in which $E_1$ and $E_2$, independently of one another, are each a group of the formula Ia or Ib

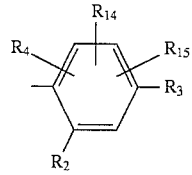

-continued

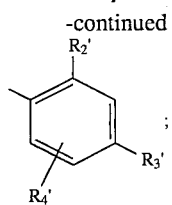
(Ib)

$R_1$ is —A,

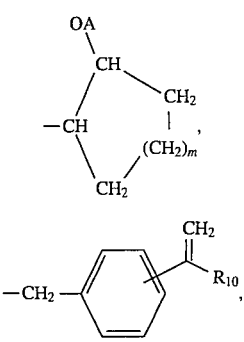

—$CH_2$—$C(=CH_2)$—$R_{10}$,  —$(CH_2)_p$—$SiR_{11}R_{11}'$—$CH=CH_2$,  —$C(=O)$—$(CH_2)_q$—$CH=CH_2$, —$CHR_8$—$(CH_2)_r$—$C(=O)$—$O$—$CH_2$—$CH(OH)$—$CH_2$—$OA$, —$CR_8R'_8$—$(CH_2)_l$—$C(=O)$—$XA$ or —$C(=O)$—$O$—$CH_2$—$C(=CH_2)$—$R_{10}$, and, in case that $E_1$ or $E_1$ and $E_2$ are a group of formula Ib, $R_1$ is also —$CH_2$—$CH(XA)$—$CH_2$—$O$—$R_7$,  —$CR_8R'_8$—$(CH_2)_l$—$XA$, —$CH_2$—$CH(OA)$—$R_9$ or —$CH_2$—$CH(OH)$—$CH_2$—$XA$;

A is —$C(=O)$—$CR_5=CH$—$R_6$;

$R_2$, independently of one another, are H, $C_1$–$C_{12}$alkyl, $C_5$–$C_{12}$cycloalkyl, $C_3$–$C_6$alkenyl, halogen, phenyl or trifluoromethyl;

$R_2'$, independently of one another, are $C_1$–$C_{18}$alkoxy, $C_3$–$C_{18}$alkenoxy, —O—CO—$R_{12}$, —OH or —OA;

$R_3$ and $R_3'$, independently of one another, are H, —OH, —$OR_1$, —$OR_{131}$, $C_1$–$C_{18}$alkyl, $C_3$–$C_{18}$alkenyl, $C_6$–$C_{12}$cycloalkyl, halogen, trifluoromethyl, phenyl, phenyl-$C_1$–$C_4$alkyl, —CN, $C_1$–$C_{18}$alkyl-$S(=O)_t$— or phenyl-$S(=O)_t$—;

$R_4$, $R_4'$ and $R_4''$, independently of one another, are H, $C_1$–$C_{18}$alkyl, $C_3$–$C_6$ alkenyl, —$OR_{131}$, halogen, trifluoromethyl, phenyl, phenyl-$C_1$–$C_4$alkyl, mono- to tri-$C_1$–$C_4$alkyl-substituted phenyl-$C_1$–$C_4$alkyl, —CN, $C_1$–$C_{18}$alkyl-$S(=O)_t$— or phenyl-$S(=O)_t$—;

$R_5$ is H, —$CH_2$—$COOR_{13}$, $C_1$–$C_4$alkyl or —CN;

$R_6$ is H, —$COOR_{13}$, $C_1$–$C_7$alkyl or phenyl;

$R_7$ is $C_1$–$C_{18}$alkyl, $C_5$–$C_{12}$cycloalkyl, $C_3$–$C_{18}$alkenyl; phenyl; phenyl which is substituted by one to three $C_1$–$C_8$alkyl, $C_1$–$C_8$alkoxy, $C_3$—$C_8$alkenoxy, halogen or trifluoromethyl radicals; phenyl-$C_1$–$C_4$alkyl; $C_3$–$C_{50}$alkyl which is interrupted by —O—; 1-adamantyl; 2-adamantyl; norbornyl; 2-methylnorbornyl, —$C(=O)$—$R_{12}$ or —A;

$R_8$ and $R_8'$, independently of one another, are H; $C_1$–$C_{18}$alkyl; phenyl; phenyl which is substituted by one to three $C_1$–$C_8$alkyl, $C_1$–$C_8$alkoxy, $C_3$–$C_8$alkenoxy, halogen or trifluoro methyl radicals; or are phenyl-$C_1$–$C_4$alkyl;

$R_9$ is $C_1$–$C_8$alkyl, phenyl or phenyl-$C_1$–$C_4$alkyl;

$R_{10}$ is H or —$CH_3$;

$R_{11}$ and $R_{11}'$, independently of one another, are $C_1$–$C_4$alkyl or phenyl or phenyl which is substituted by one to three $C_1$–$C_8$alkyl, $C_1$–$C_8$alkoxy, $C_3$–$C_8$alkenoxy, halogen or trifluoromethyl radicals;

$R_{12}$ is H, $C_1$–$C_{18}$alkyl, phenyl, phenyl-$C_1$–$C_4$alkyl, $C_5$–$C_{12}$cycloalkyl, $C_{C1}$–$C_{12}$alkoxy, phenoxy, norborn-2-yl, 5-norbornen-2-yl or 1-adamantyl;

$R_{13}$ is $C_1$–$C_{18}$alkyl; $C_3$–$C_{18}$alkenyl; phenyl; $C_5$–$C_{12}$cycloalkyl; $C_3$–$C_{50}$alkyl which is interrupted by —O—; phenyl which is substituted by one to three $C_1$–$C_8$alkyl, $C_1$–$C_8$alkoxy, $C_3$–$C_8$alkenoxy, halogen or trifluoromethyl radicals; phenyl-$C_1$–$C_4$alkyl; 2-adamantyl; norbornyl or 2-methylnorbornyl;

$R_{14}$ and $R_5$, independently of one another, are H, $C_1$–$C_{18}$alkyl, $C_3$–$C_{18}$alkenyl, $C_6$–$C_{12}$cycloalkyl, halogen, trifluormethyl, phenyl, phenyl-$C_1$–$C_4$-alkyl, —CN, $C_1$–$C_{18}$alkyl-$(S=O)_t$—, phenyl-$(S=O)_t$— or —$OR_{131}$;

$R_{131}$ is $C_1$–$C_{18}$alkyl; $C_1$–$C_{18}$alkyl which is substituted by —OH, $C_1$–$C_8$alkoxy, $C_5$–$C_{12}$cycloalkoxy, $C_3$–$C_6$alkenyloxy, halogen, —$COOR_{13}$, —$CONH_2$, —$COHNR_{132}$, —$CON(R_{132})(R_{133})$, —$NHCOR_{12}$, —CN, —$OCOR_{12}$, phenoxy and/or by phenoxy which is substituted by $C_1$–$C_{18}$alkyl, $C_1$–$C_{18}$alkoxy or halogen; or is $C_3$–$C_{18}$alkenyl; $C_6$–$C_{12}$cycloalkyl; $C_1$–$C_4$alkyl- and/or —$OCOR_{12}$-substituted $C_6$–$C_{12}$cycloalkyl; $C_3$–$C_{50}$alkyl which is interrupted by —O—; $C_3$–$C_{50}$alkyl which is interrupted by —O— and substituted by —OH or —O—CO—$R_{12}$; phenyl; phenyl-$C_1$–$C_4$alkyl; —$COR_{12}$ or —$SO_2R_{12}$;

$R_{132}$ and $R_{133}$, independently of one another, are $C_1$–$C_{12}$alkyl, $C_3$–$C_{12}$alkoxyalkyl, $C_4$–$C_{16}$dialkylaminoalkyl or $C_5$–$C_{12}$cycloalkyl; or $R_{132}$ and $R_{133}$ together are $C_3$–$C_9$alkylene, $C_3$–$C_9$oxaalkylene or -azaalkylene;

X is —$NR_8$, —O—, —NH—$(C_nH_{2n})$—NH— or —O—$(C_kH_{2k})$—NH;

k is a number from 2 to 4; l is a number from 0 to 19;

m is a number from 2 to 8; n is a number from 0 to 4;

p is a number from 0 to 10; q is a number from 1 to 8;

r is a number from 0 to 18; and t is the number 0, 1 or 2.

Application and preferences for these monomeric UV absorber are basically the same as for the polymeric UV absorbers defined in the beginning.

Among the polymeric UV absorbers are those compounds a subject of special interest which are obtainable by polymerization of the monomeric UV absorbers mentioned above, which are compounds of formula I, wherein $R_1$ is —A,

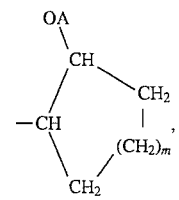

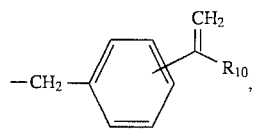

—CH$_2$—C(=CH$_2$)—R$_{10}$, —(CH$_2$)$_p$—SiR$_{11}$R$_{11}$'—CH=CH$_2$, —C(=O)—(CH$_2$)$_q$—CH=CH$_2$, —CHR$_8$—(CH$_2$)$_r$—C(=O)—O—CH$_2$—CH(OH)—CH$_2$—OA, —CR$_8$R'$_8$—(CH$_2$)$_1$—C(=O)—XA or —C(=O)—O—CH$_2$—C(=CH$_2$)—R$_{10}$, and, if E$_1$ or E$_1$ and E$_2$ are a group of formula Ib (compounds derived from bis(2-hydroxyphenyl)triazine or tris(2-hydroxyphenyl)triazine), R$_1$ also embraces —CH$_2$—CH(XA)—CH$_2$—O—R$_7$, —CR$_8$R'$_8$—(CH$_2$)$_1$XA, —CH$_2$—CH(OA)—R$_9$, —CH$_2$—CH(OH)—CH$_2$—XA; especially those, wherein R$_1$ is

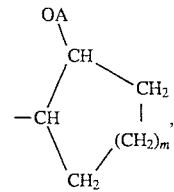

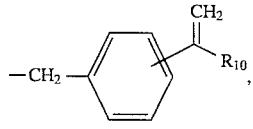

—(CH$_2$)$_p$—SiR$_{11}$R$_{11}$'—CH=CH$_2$, —CHR$_8$—(CH$_2$)$_r$, —C(=O)—O—CH$_2$—CH(OH)—CH$_2$—OA, —CR$_8$R'$_8$—(CH$_2$)$_1$—C(=O)—XA or —C(=O)—O—CH$_2$—C(=CH$_2$)—R$_{10}$, and, if E$_1$ or E$_1$ and E$_2$ are a group of formula Ib, R$_1$ additionally embraces —A, —CH$_2$—C(=CH$_2$)—R$_{10}$, —C(=O)—(CH$_2$)$_q$—CH=CH$_2$, —CH$_2$—CH(XA)—CH$_2$—O—R$_7$, —CR$_8$R'$_8$—(CH$_2$)$_1$—XA, —CH$_2$—CH(OA)—R$_9$, —CH$_2$—CH(OH)—CH$_2$—XA; a group of compounds especially preferred among these are compounds, wherein E$_1$ is a group of formula Ib and E$_2$ is a group of formula Ia (compounds derived from bis(2-hydroxyphenyl)triazine).

Compounds of the formula I which can be employed in accordance with the invention therefore conform, for example, to the formula Ic

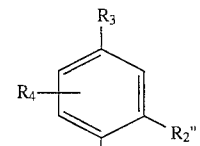

in which

A —C(=O)—CR$_5$=CH—R$_6$;

R$_1$, independently of one another, are —A, —CH$_2$—CH(OA)—CH$_2$—O—R$_7$, —CHR$_8$—(CH$_2$)$_1$—OA, —CH$_2$—CH(OA)—R$_9$, —CH$_2$—CH(OH)—CH$_2$—OA,

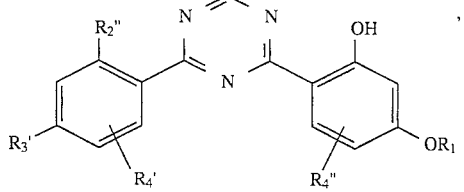

—CH$_2$—C(=CH$_2$)—R$_{10}$, —(CH$_2$)$_p$—SiR$_{11}$R$_{11}$'—CH=CH$_2$, —C(=O)—(CH$_2$)$_q$—CH=CH$_2$, —CHR$_8$—(CH$_2$)$_r$—C(=O)—O—CH$_2$—CH(OH)—CH$_2$—OA or —C(=O)—O—CH$_2$—C(=CH$_2$)—R$_{10}$;

R$_2$", independently of one another, are H, —OH, —OA, C$_1$–C$_{12}$alkyl, cyclohexyl, C$_3$–C$_6$alkenyl, C$_1$–C$_{18}$alkoxy, C$_3$–C$_{18}$alkenoxy, halogen, phenyl or trifluoromethyl;

R$_3$ and R$_3$', independently of one another, are H, —OH, —OR$_1$, C$_1$–C$_{12}$alkyl, cyclohexyl, C$_3$–C$_6$alkenyl, C$_1$–C$_{18}$alkoxy, C$_3$–C$_{18}$alkenoxy, halogen, trifluoromethyl, phenyl, phenoxy, phenyl-C$_1$–C$_4$alkyl, phenyl-C$_1$–C$_4$alkoxy, —CN, C$_1$–C$_{18}$alkyl-S(=O)$_t$— or phenyl-S(=O)$_t$—;

R$_4$, R$_4$' and R$_4$", independently of one another, are H, C$_1$–C$_{12}$alkyl, C$_3$–C$_6$alkenyl, C$_1$–C$_{18}$alkoxy, C$_3$–C$_{18}$alkenoxy, halogen, trifluoromethyl, phenyl, phenoxy, phenyl-C$_1$–C$_4$alkyl, mono- to tri-C$_1$–C$_4$alkyl-substituted phenyl-C$_1$–C$_4$alkyl, phenyl-C$_1$–C$_4$alkoxy, —CN, C$_1$–C$_{18}$alkyl-S(=O)$_t$— or phenyl-S(=O)$_t$—;

R$_5$ is H, —CH$_2$—COOR$_{13}$, C$_1$–C$_4$alkyl or —CN;

R$_6$ is H, —COOR$_{13}$, C$_1$–C$_{17}$ alkyl or phenyl;

R$_7$ is C$_1$–C$_{18}$alkyl, cyclohexyl, C$_3$–C$_{18}$ alkenyl, phenyl, phenyl which is substituted by one three C$_1$–C$_8$alkyl, C$_1$–C$_8$alkoxy, C$_2$–C$_8$alkenoxy, halogen or trifluoromethyl radicals, phenyl-C$_1$–C$_4$alkyl or —C(=O)—R$_{12}$;

R$_8$ is H or C$_1$–C$_{18}$alkyl;

R$_9$ is C$_1$–C$_{18}$alkyl, phenyl or phenyl-C$_1$–C$_4$alkyl;

R$_{10}$ is H or —CH$_3$;

R$_{11}$ and R$_{11}$', independently of one another, are C$_1$–C$_4$alkyl or phenyl or phenyl which is substituted by one to three C$_1$–C$_8$alkyl, C$_1$–C$_8$alkoxy, C$_3$–C$_8$alkenoxy, halogen or trifluoromethyl radicals;

$R_{12}$ is $C_1$–$C_{18}$alkyl, $C_2$–$C_{18}$alkenyl or phenyl;

$R_{13}$ is $C_1$–$C_{18}$alkyl, $C_3$–$C_{18}$alkenyl or phenyl;

l is a number from 0 to 19;

p is a number from 0 to 10;

q is a number from 1 to 8;

r is a number from 0 to 18; and t is the number 0, 1 or 2.

Preference is given to compounds of the formula (I) in which $R_1$, independently of one another, are —A, —$CH_2$—CH(XA)—$CH_2$—O—$R_7$, —$CR_8R_8'$—$(CH_2)_l$—XA,

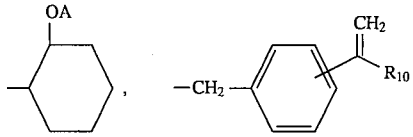

or —$CHR_8$—$(CH_2)_r$—C(=O)—O—$CH_2$—CH(OH)—$CH_2$—OA;

$R_2$ is H, $C_1$–$C_4$ alkyl, $C_3$alkenyl, $C_1$–$C_4$alkoxy, $C_3$alkenoxy, F, Cl or phenyl;

$R_2'$ is $C_1$–$C_4$alkoxy, $C_3$alkenoxy, —O—$COR_{12}$, —OA or —OH;

$R_3$ and $R_3'$, independently of one another, are H, —OH, —$OR_1$, —$OR_{131}$, $C_1$–$C_4$alkyl, cyclohexyl, $C_3$alkenyl, F, Cl, trifluoromethyl, phenyl, benzyl or —CN;

$R_4'$ and $R_4''$, independently of one another, are H, $C_1$–$C_4$alkyl, $C_3$alkenyl, $C_1$–$C_4$alkoxy, $C_3$alkenoxy, F, Cl, trifluoromethyl, phenyl, phenyl-$C_1$–$C_3$alkyl or —CN;

$R_5$ is H or —$CH_3$;

$R_6$ is H, —$COOR_{13}$, —$CH_3$ or phenyl;

$R_7$ is $C_1$–$C_8$alkyl, cyclohexyl, $C_2$–$C_8$alkenyl, phenyl, or phenyl which is substituted by one to three $C_1$–$C_4$alkyl or $C_1$–$C_4$alkoxy substituents, or benzyl;

$R_8$ and $R_8'$, independently of one another, are H or $C_1$–$C_{18}$alkyl;

$R_9$ is $C_1$–$C_{10}$alkyl, phenyl or benzyl;

$R_{12}$ is H, $C_1$–$C_{18}$alkyl, phenyl, phenyl-$C_1$–$C_4$alkyl or cyclohexyl;

$R_{13}$ is $C_1$–$C_4$alkyl, $C_3$alkenyl, cyclohexyl, phenyl-$C_1$–$C_4$alkyl or phenyl;

$R_4$, $R_{14}$ and $R_{15}$, independently of one another, are H, F, Cl, $C_1$–$C_4$alkoxy, $CF_3$, phenyl, CN or $C_1$–$C_4$alkyl;

$R_{131}$ is $C_1$–$C_{18}$alkyl, $C_3$–$C_{18}$alkyl which is substituted by —OH, $C_1$–$C_{18}$alkoxy, $C_5$–$C_{12}$cycloalkoxy, —$COOR_{13}$, —$CONH_2$, —$COHNR_{132}$, —$CON(R_{132})(R_{133})$, —$NHCOR_{12}$, —CN, —$OCOR_{12}$ and/or phenoxy, or is $C_3$alkenyl, $C_6$–$C_{12}$cycloalkyl, $C_3$–$C_{50}$alkyl which is interrupted by one or more —O— and may be substituted by OH or —O—$COR_{12}$, or is phenyl, phenyl-$C_1$–$C_4$alkyl, —$COR_{12}$ or —$SO_2R_{12}$;

X is —O— or —$NR_8$—;

l is a number from 1 to 19; and r is a number from 0 to 10.

Of these, there is particular interest in the compounds of the formula I, in which the radicals $E_1$ and $E_2$, independently of one another, are each a group of the formula Ib or Ie,

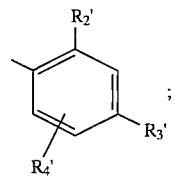

(Ib)

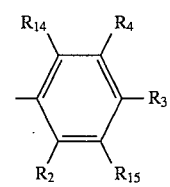

(Ie)

and in which $R_4'$ and $R_4''$ are in the meta-position to the triazine ring.

Particular preference is given to compounds of the formula (I) in which

A is —C(=O)—$CR_5$=CH—$R_6$;

$R_1$, independently of one another, are —A, —$CH_2$—CH(OA)—$CH_2$—O—$R_7$, —$CH_2$—CH(OA)—$R_9$,

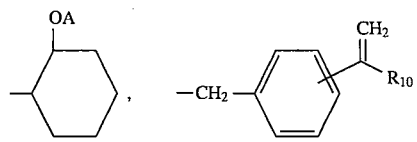

or —$CHR_8$—$(CH_2)_l$—OA;

$R_2$ is H, —$CH_3$, $C_1$–$C_2$alkoxy, $C_3$alkenoxy or Cl;

$R_2'$ is —OH;

$R_3$ is H, —$CH_3$, $C_1$–$C_4$alkoxy, $C_3$alkenoxy, F, Cl, phenyl, benzoxy or —CN;

$R_3'$ is —$OR_1$ or —$OR_{131}$;

$R_4$, $R_{14}$ and $R_{15}$, independently of one another, are H, $OCH_3$, F, Cl, phenyl, CN or $CH_3$;

$R_4'$ and $R_4''$, independently of one another, are H, —$CH_3$, $C_3$alkenyl, —$OCH_3$, $C_3$alkenoxy, F, Cl, phenyl-$C_1$–$C_3$alkyl or —CN;

$R_5$ is H or —$CH_3$;

$R_6$ is H or —$CH_3$;

$R_7$ is $C_1$–$C_8$alkyl, cyclopentyl, cyclohexyl, $C_3$alkenyl, phenyl or benzyl;

$R_8$ is H or $C_1$–$C_{18}$alkyl;

$R_9$ is $C_1$–$C_{10}$alkyl or phenyl;

$R_{12}$ is $C_1$–$C_{18}$alkyl, phenyl or cyclohexyl;

$R_{131}$ is $C_1$–$C_{18}$alkyl or $C_3$–$C_{18}$alkyl which is substituted by $C_1$–$C_{18}$alkoxy, OH, phenoxy, —$NHCOR_{12}$ and/or —$OCOR_{12}$; and l is a number from 1 to 19.

Very particular preference is given to compounds of the formula (I) in which

A is —C(=O)—$CR_5$=CH—$R_6$;

$R_1$, independently of one another, are —A, —$CH_2$—CH(OA)—$CH_2$—O—$R_7$, —$CH_2$—CH(OA)—$R_9$,

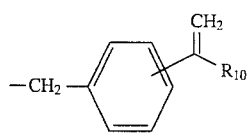

$R_2$ is H or $CH_3$;

$R_2'$ is —OH;

$R_3$ is H, —$CH_3$, $OCH_3$, Cl or phenyl;

$R_3'$ is —$OR_1$ or —$OR_{131}$;

$R_4$ is H, Cl, $OCH_3$, F or $CH_3$;

$R_4'$ and $R_4''$ are H or $CH_3$;

$R_{14}$ and $R_{15}$ are hydrogen, $CH_3$ or $OCH_3$;

$R_5$ is H or —$CH_3$;

$R_6$ is H;

$R_7$ is $C_1$–$C_8$alkyl;

$R_9$ is $C_1$–$C_{10}$alkyl;

$R_{12}$ is $C_1$–$C_8$alkyl;

$R_{131}$ is $C_1$–$C_{18}$alkyl or $C_3$–$C_{18}$alkyl which is substituted by —$OCOR_{12}$; and l is a number from 1 to 10.

A special preference is given to compounds of the formula (I) in which at least one of the radicals $R_3$ and $R_3'$ is —$OR_1$.

The invention furthermore relates, particularly interestingly, to the use of compounds of the formula I in which $E_1$ conforms to the formula Ib and $E_2$ conforms to the formula Ia, in particular to the formula Ie. Of these, particular preference is given to compounds with mixed substituents in which neither $R_3$ nor $R_3'$ is —$OR_1$; especially those in which $R_2'$ is OH and $R_3'$ is $C_1$–$C_{18}$alkoxy or $C_2$–$C_{18}$alkoxy which is interrupted by —O— or by —$OCOR_{12}$ and/or is substituted by OH, $C_1$–$C_{18}$alkoxy or $C_5$–$C_{12}$cycloalkoxy, where $R_{12}$ is $C_1$–$C_{18}$alkyl, phenyl, phenyl-$C_1$–$C_4$alkyl or $C_5$–$C_{12}$cycloalkyl; these are especially compounds wherein $R_1$ is —$CR_8R_8'$—$(CH_2)_l$—XA.

Preference is given to polymeric compounds built up from at least one monomer of the formula (I). Suitable polymeric compounds for this purpose are both homopolymers and copolymers, where the copolymers can be built up from at least two different compounds of the formula (I) or from at least one compound of the formula (I) and a further comonomer.

Preferred monomers of the formula (I) are those which contain any acrylate group, in which case A in the polymer is

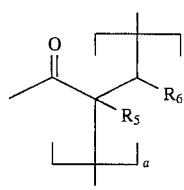

and a is an integer, and those which contain a styrene unit, in which case A in the polymer is

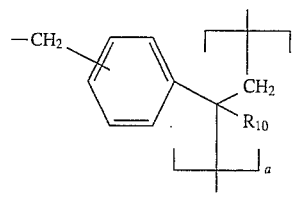

and a is an integer. a is preferably a number in the range from 3 to 100,000, in particular from 4 to 1000.

The terminal groups in the polymers which can be used in accordance with the invention arise in a known manner from the conditions of the polymerization reaction.

The preferences described in greater detail above apply to the monomers of the formula (I) which make up the polymers. Preference is thus given to homopolymers built up from monomers of a compound of the formula (I) mentioned as preferred. Preference is thus given to copolymers built up from monomers of at least two compounds of the formula (I) mentioned as preferred. An analogous situation applies to the particular preferences.

Suitable further comonomers (comonomers which are different from compounds of the formula (I)) include alpha-unsaturated carboxylic acids, for example acrylic and methacrylic acid, vinyl ethers, styrene, vinylpyridine, acrylonitrile, vinylpyrrolidone and derivatives thereof.

Particular importance is attached to the use of other copolymerizable stabilizers, for example ethylenically unsaturated derivatives of sterically hindered amines (HALS), 2-(2'-hydroxyphenyl)benzotriazoles, 2-hydroxybenzophenones, derivatives of cinnamic acid or sterically hindered phenols.

In copolymers which, in addition to units of at least one compound of the formula (I), also contain further comonomers, the comonomer:monomer of the formula I ratio is preferably up to 10:1, in particular in the range from 1:1 to 5:1.

Corresponding HALS which can be used as comonomer are generally characterized by the structural unit

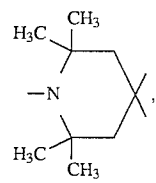

where the 3 free bonds are saturated by H or an organic substituent, and the molecule contains at least one polymerizable, ethylenically unsaturated double bond; corresponding compounds are described, inter alia, in U.S. Pat. Nos. 4,942,238, 4,983,737 and EP-A-0 634 399, and the literature cited therein.

Corresponding 2-(2'-hydroxyphenyl)benzotriazoles which can be used as comonomer are generally characterized by the structural unit

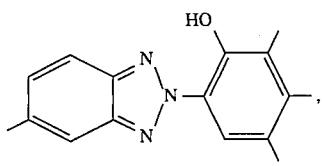

where the four free bonds are saturated by H or organic substituents, and the molecule contains at least one polymerizable, ethylenically unsaturated double bond; corresponding compounds are described, inter alia, in U.S. Pat. Nos. 5,099,027, 4,528,311, 5,147,902, Research Disclosure 32 592, U.S. Pat. Nos. 4,785,063, 4,892,915, 4,611,061, EP-A-o 190 003, EP-A-0 508 744, U.S. Pat. Nos. 4,716,234, 3,493,539, 5,234,807, 5,256,359, 5,385,815, 5,372,922, JP-A-03-139 590, EP-A-0 431 868, JP-A-03-8547, GB-A-2 232 667, EP-A-0 282 294, EP-A-0 343 996, EP-A-0 133 164, EP-A-0 131 468, J. Macromol. Sci., Pure Appl. Chem. A30 (9–10), 741 (1993) and Polm. Bull. 12 (5), 375 (1984), and the literature cited therein.

Corresponding 2-hydroxybenzophenones which can be used as comonomer are generally characterized by the structural unit

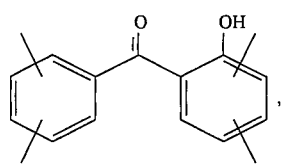

where the four free bonds are saturated by H or organic substituents, and the molecule contains at least one polymerizable, ethylenically unsaturated double bond; corresponding compounds are described, inter alia, in CH-B-383 001 and CH-B-376 899, and the literature cited therein.

Corresponding cinnamic acid derivatives which can be used as comonomer are generally characterized by the structural unit

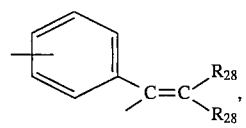

where $R_{28}$ and $R_{28}'$ are independently CN or $COOR_{13}$, $R_{13}$ is as defined above and the two free bonds are saturated by organic substituents, and the molecule contains at least one polymerizable, ethylenically unsaturated double bond.

Corresponding sterically hindered phenols which can be used as comonomer are generally characterized by the structural unit

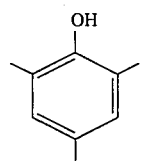

where the three tree bonds are saturated by organic substituents, and the molecule contains at least one polymerizable, ethylenically unsaturated double bond, usually in the substituent in the p-position to the hydroxyl group; corresponding compounds are described, inter alia, in U.S. Pat. No. 3,708,520 and the literature cited therein.

The further comonomers (comonomers different to compounds of the formula (I)) are preferably compounds of the formulae (II)–(VII) below (II) $R_{18}$—CH═C($R_{17}$)—C(═O)—X'—$R_{20}$, in which X' is —O— or —$NR_{19}$—;

$R_{17}$ is H, $C_1$–$C_4$alkyl, —$CH_2$—$COOR_{12}$, —Cl or —CN;

$R_{18}$ is H, —$COOR_{21}$ or —$CH_3$;

$R_{19}$ is H, $C_1$–$C_8$alkyl, $C_4$–$C_{12}$cycloalkyl, —N($R_x$)2-substituted $C_1$—$C_4$alkyl, —S(═O)—$R_x$, —C($CH_3$)$_2$—$CH_2$—C(═O)—$CH_3$, —C($CH_3$)$_2$—$CH_2$—SO$_3$M, —($CH_2$)$_s$—$SO_3$M or

$R_{20}$ is H; $C_1$-$C_{18}$alkyl, $C_2$-$C_{18}$alkenyl, $C_2$-$C_{18}$alkyl which is interrupted by one or more O atoms and can be substituted by OH, or —($CH_2$)$_s$—$SO_3$M;

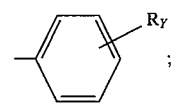

—$CH_2$F, —$CH_2$Cl, —$CH_2$CN, —$CH_2CH_2$Cl, —$CH_2CH_2$CN, —$CH_2CH_2$—$COOR_x$, $C_7$-$C_{11}$phenylalkyl, naphthyl, —N($R_x$)$_2$-substituted $C_1$–$C_4$alkyl, adamantyl or $C_6$-$C_{12}$cycloalkyl;

$R_{21}$ is H, $C_1$-$C_{18}$aAlkyl, phenyl or $C_2$-$C_{18}$alkenyl;

$R_x$ is $C_1$-$C_4$alkyl or phenyl;

$R_y$ is H, $C_1$-$C_{12}$alkyl, phenyl, —CO—$OR_x$, —CN, —F, or —Cl;

M is H or an alkali metal; and s is a number from 1 to 5.

(III) $R_{22}$—C(═O)—O—CH═$CH_2$, in which $R_{22}$ is $C_1$-$C_{19}$alkyl or phenyl.

(IV)

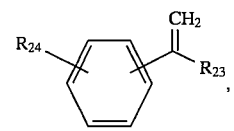

in which $R_{23}$ is H or —$CH_3$;

$R_{24}$ is H, —$CR_{23}$═$CH_2$, —C(O)-phenyl or —$SO_3$M; and

M is H or an alkali metal.

(V)

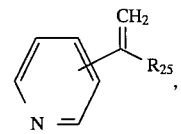

in which $R_{25}$ is H or —$CH_3$.

(VI) $CH_2$═$CR_{26}$—$R_{27}$, in which $R_{26}$ is H, —F, —Cl or —CH$_3$ and
$R_{27}$ is —Cl, —Br, —F or —CN.
(VII)

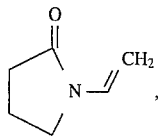

and the abovementioned polymerizable, ethylenically unsaturated derivatives of sterically hindered amines (HALS), 2-(2'-hydroxyphenyl)benzotriazoles, 2-hydroxybenzophenones and sterically hindered phenols.

The possible meanings of the substituents in the formula (II)–(VII) correspond to those as given above for the compounds of the formula (I).

Any substituents in the above formulae which are alkyl having up to 18 carbon atoms which is interrupted by one or more O atoms are radicals such as —(CH$_2$—CH$_2$—O)$_{1-8}$—C$_3$, —(CH$_2$—CH$_2$—O)$_{1-8}$—C$_2$H$_5$ or —(CH$_2$—CH$_2$—CH$_2$—O)$_{1-5}$—CH$_3$.

Any substituents in the above formulae which are alkali metal are Li, Na or K.

Particularly preferred further comonomers (comonomers which are different compounds of the formula (I)) are compounds of the formulae (II), (III), (IV) and (VII).

Preference is given to copolymers obtainable by polymerization of at least one preferred compound of the formula (I) and at least one of the comonomers of the formulae (II)–(VII).

Particular preference is given to copolymers obtainable by polymerization of at least one particularly preferred compound of the formula (I) and at least one of the comonomers of the formulae (II), (III), (IV) or (VII).

Very particular preference is given to copolymers obtainable by polymerization of at least one very particularly preferred compound of the formula (I) and at least one of the comonomers of the formulae (II), (III), (IV) or (VII), where $R_{17}$ is H or —CH$_3$;

$R_{18}$ is H or —CH$_3$;

$R_{19}$ is H, C$_1$–C$_4$alkyl, —C(CH$_3$)$_2$—CH$_2$—SO$_3$M or —(CH$_2$)$_s$—SO$_3$M;

$R_{20}$ is H, C$_1$–C$_8$alkyl, or C$_2$–C$_8$alkyl which is interrupted by one or more O atoms;

$R_{22}$ is —CH$_3$;

$R_{23}$ and $R_{24}$ are H;

M is H, Li, Na or K;

X is —O— or —NR$_{19}$—; and s is the number 2 or 3.

The invention also pertains to a photographic recording material comprising besides the UV absorber of the invention additionally a stabilizer of the class of the sterically hindered amines (HALS) enthält.|17| Preferably, the sterically hindered amine is present in the same layer as the UV absorber of the invention. The sterically hindered amine is usually a cyclic sterically hindered amine, more particularly a compound of the series of the derivatives of polyalkylpiperidines or polyalkylpiperazines, comprising at least one group of formula HALS-II or HALS-III

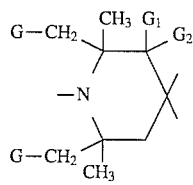

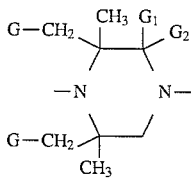

wherein G is hydrogen or methyl, and G$_1$ and G$_2$ are hydrogen, methyl or, taken together, are =O. The polyalkylpiperidine groups of formula II or III are preferably bonded in 4-position to one or two polar substituents or to a polar spiro ring system.

A sterically hindered amine is used in this particular photographic recording material especially in an amount from 1 mg/m$^2$ to 200 mg/m$^2$.

Examples for useful sterically hindered amines are the compounds bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin.

Preferred for use as costabilizer in the photographic recording material of the invention are especially compounds of the type HALS-II, which are substituted on the nitrogen atom by —CO—R, —O—R, benzyl or allyl, where R is a organic radical, mainly a hydrocarbon radical containing 1 to 30 carbon atoms. Examples for such preferred costabilizers can be found in the above list.

Some of said compounds of the formula (I) are known or can be prepared by methods known in principle. The reaction schemes below show a fundamental two-step (a+b) process for the preparation of compounds of the formula (I) derived from triazinylmonoresorcinols. Compounds derived from bis- or trisresorcinol can also be prepared analogously. Further details on possible preparation processes are given in EP-A-0 434 608.

a) Alkylation of the para-OH group of the resorcinol radical (by, for example, a glycidyl ether or an ω-bromoalcohol):

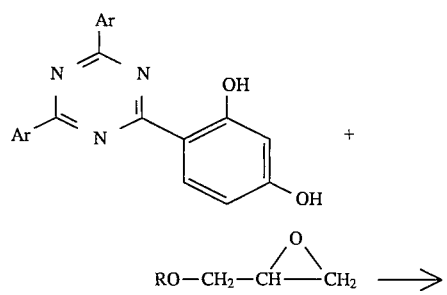

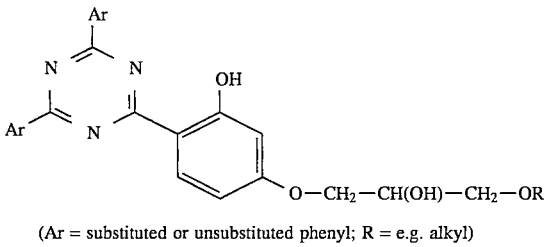

(Ar = substituted or unsubstituted phenyl; R = e.g. alkyl)

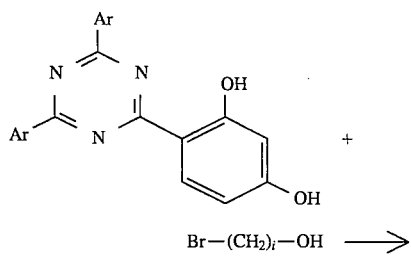

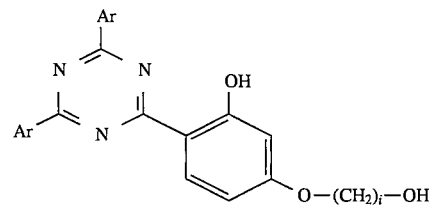

(Ar = substituted or unsubstituted phenyl; i = 1-20)

b) Acrylation or methacrylation of the aliphatic OH group:

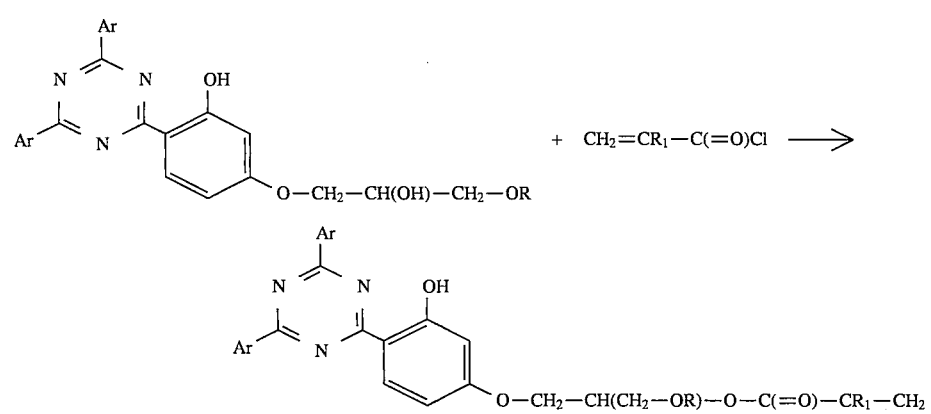

(Ar = substituted or unsubstituted phenyl; R = e.g. alkyl; $R_1$ = H or —$CH_3$)

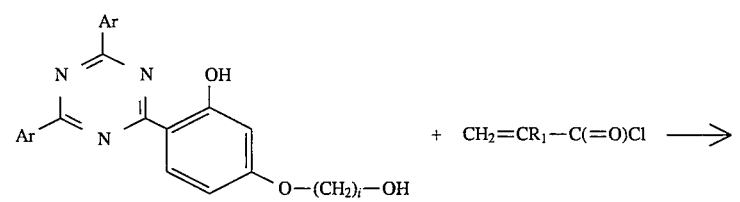

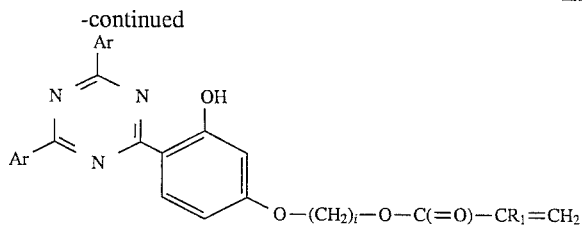

(Ar = substituted or unsubstituted phenyl; i: 1–20; $R_1$ = H or —$CH_3$)

The polymerization of one of the monomeric compounds of the formula (I) can be initiated by free-radical, anionic or cationic initiators. Preference is given to free-radical initiators, which decompose to form free radicals on warming, for example organic peroxides or hydroperoxides, azo compounds or redox catalysts. The polymerization can also be initiated by high-energy radiation. The polymerization can be carried out in solution, emulsion, dispersion or in bulk. These processes are known to the person skilled in the art. Suitable polymerization processes are also described in EP-A-0 5777122, page 9, line 46 to page 10, line 35.

Examples of compounds of the formula (I) are the following:

| No. | $L_1$ |
|---|---|
| (100) | —$CH_2$—$CH(CH_2$—O-n-$C_4H_9)$—O—C(O)—CH=$CH_2$ (n-$C_4H_9$: n-butyl) |
| (101) | —$CH_2$—$CH(CH_2$—O-n-$C_4H_9)$—O—C(O)—C($CH_3$)=$CH_2$ |
| (102) | —$(CH_2)_{11}$—O—C(O)—CH=$CH_2$ |
| (103) | —$(CH_2)_{11}$—O—C(O)—C($CH_3$)=$CH_2$ |
| (104) | —$CH_2$—CH(n-$C_4H_9$)—O—C(O)—C($CH_3$)=$CH_2$ |
| (105) | —$CH_2$—(C_6H_4)—CH=$CH_2$ |
| (106) | —$CH_2$—$CH_2$—O—C(O)—C($CH_3$)=$CH_2$ |
| (107) | —C(O)—C($CH_3$)=$CH_2$ |

| No. | $L_1$ |
|---|---|
| (200) | —$CH_2$—$CH_2$—O—C(O)—CH=$CH_2$ |

-continued

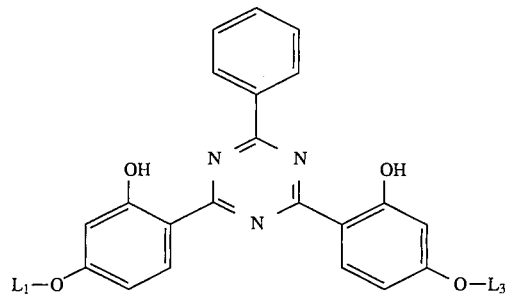

| No. | L₁, L₃ |
|---|---|
| (201) | —CH₂—CH₂—O—C(O)—C(CH₃)=CH₂ |
| (202) | —CH₂—CH(CH₂—O-n-C₄H₉)—O—C(O)—CH=CH₂ |
| (203) | —(CH₂)₁₁—O—C(O)—CH=CH₂ |
| (204) | —(CH₂)₁₁—O—C(O)—C(CH₃)=CH₂ |
| (205) | —CH₂—CH(n-C₄H₉)—O—C(O)—C(CH₃)=CH₂ |
| (206) | —CH₂—CH(n-C₄H₉)—O—C(O)—CH=CH₂ |
| (207) | L₁ = n-C₆H₁₃, L₃ = —(CH₂)₁₁—O—C(O)—C(CH₃)=CH₂ |
| (208) | L₁ = —(CH₂)₁₁—O—C(O)—CH₃, L₃ = —(CH₂)₁₁—O—C(O)—C(CH₃)=CH₂ |

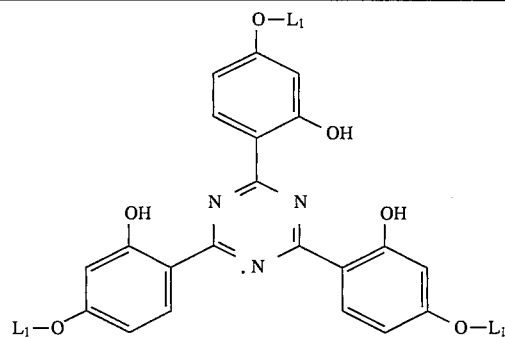

| No. | L₁ |
|---|---|
| (300) | —CH₂—CH(CH₂—O-n-C₄H₉)—O—C(O)—CH=CH₂  (n-C₄H₉: n-butyl) |
| (301) | —(CH₂)₁₁—O—C(=O)—CH=CH₂ |
| (302) | —(CH₂)₁₁—O—C(=O)—C(CH₃)=CH₂ |

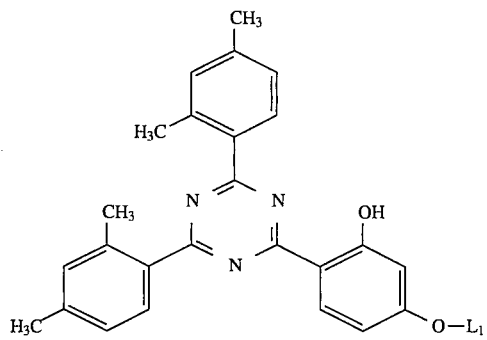

| No. | L₁ |
|---|---|
| (400) | —CH₂—CH(CH₂—O-n-C₄H₉)—O—C(O)—C(CH₃)=CH₂ |
| (401) | —(CH₂)₁₁—O—C(O)—CH=CH₂ |
| (402) | —(CH₂)₁₁—O—C(O)—C(CH₃)=CH₂ |
| (403) | —CH₂—CH(n-C₄H₉)—O—C(O)—C(CH₃)=CH₂ |
| (404) | —CH₂—CH₂—O—C(O)—C(CH₃)=CH₂ |
| (405) | 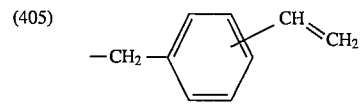 |

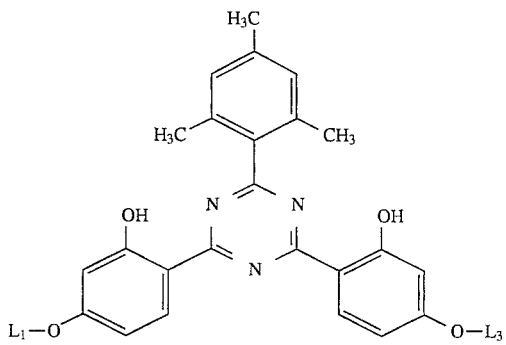

| No. | L₁, L₃ |
|---|---|
| (500) | $-CH_2-CH(CH_2-O\text{-}n\text{-}C_4H_9)-O-C(O)-CH=CH_2$ |
| (501) | $-CH_2-CH(CH_2-O\text{-}n\text{-}C_4H_9)-O-C(O)-C(CH_3)=CH_2$ |
| (502) | $-(CH_2)_{11}-O-C(O)-C(CH_3)=CH_2$ |
| (503) | $-CH_2-CH(n\text{-}C_4H_9)-O-C(O)-C(CH_3)=CH_2$ |
| (504) | $L_1 = n\text{-}C_6H_{13}$, $L_3 = -(CH_2)_{11}-O-C(O)-C(CH_3)=CH_2$ |

(505) 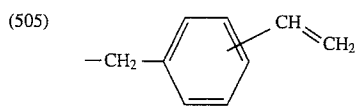

(506)    $L_1 = n\text{-}C_6H_{13}$, $L_3 = -(CH_2)_{11}-O-C(O)-CH=CH_2$

Examples of polymeric compounds are the following:
(600) homopolymer of compound (204)
(601) copolymer of compound (204) and n-butyl acrylate in the molar ratio 1:4
(602) homopolymer of compound (207)
(603) copolymer of compound (207) and n-butyl acrylate in the molar ratio 1:4
(604) homopolymer of compound (504)
(605) copolymer of compound (504) and n-butyl acrylate in the molar ratio 1:4
(606) copolymer of compound (504) and n-dodecyl methacrylate in the molar ratio 1:4
(607) homopolymer of compound (102)
(608) copolymer of compound (102) and n-butyl acrylate in the molar ratio 1:4
(609) homopolymer of compound (402)
(610) copolymer of compound (402) and n-butyl acrylate in the molar ratio 1:2
(611) homopolymer of compound (103)
(612) copolymer of compound (103) and n-butyl acrylate in the molar ratio 1:2
(613) homopolymer of compound (400)
(614) copolymer of compound (400) and n-butyl acrylate in the molar ratio 1:2
(615) copolymer of compound (105) and n-butyl acrylate in the molar ratio 1:2
(616) copolymer of compound (405) and n-butyl acrylate in the molar ratio 1:2.

The novel photographic recording material can be a black/white or colour material, preferably a colour material.

Examples of colour-photographic materials are colour negative films, colour reversal films, colour positive films, colour-photographic paper, colour reversal photographic paper, colour-sensitive materials for the dye diffusion transfer process or the silver dye bleach process.

Examples of suitable bases for the production of colour-photographic materials are films of semisynthetic and synthetic polymers, such as cellulose nitrate, cellulose acetate, cellulose butyrate, polystyrene, polyvinyl chloride, polyethylene terephthalate and polycarbonate, and paper laminated with a barytes layer or an α-olefin polymer layer (for example polyethylene). These bases can have been coloured with dyes or pigments, for example titanium dioxide. They can also have been coloured black for the purposes of light screening. The surface of the base is generally subjected to a treatment for improving the adhesion of the photographic emulsion layer, for example corona discharge with subsequent application of a substrate layer.

The colour-photographic materials usually contain at least one each of red-sensitive, green-sensitive and blue-sensitive silver halide emulsion layers and, if desired, interlayers and protective layers. The novel material preferably contains the silver-halide emulsion layers from the base in the sequence: blue-sensitive, green-sensitive and red-sensitive layers. The UV absorber in the novel colour-photographic material is preferably in a layer above the green-sensitive layer, particularly preferably in a layer above the silver-halide emulsion layer(s).

The novel UV absorber is preferably present in the photographic material in an amount of from 0.05 to 10 g/m², in particular from 0.1 to 8 g/m², especially from 0.2 to 5 g/m².

An example of a novel colour-photographic recording material is a material having the following layer sequence:

| | |
|---|---|
| a | a: Protection layer |
| b | b: Interlayer |
| c | c: Red-sensitive layer |
| d | d: Interlayer |
| e | e: Green-sensitive layer |
| f | f: Interlayer |
| g | g: Blue-sensitive layer |
| h | h: Base |

Another example is a material having a similar layer structure, but in which layer a is absent. The novel UV absorber of the formula (I) or the corresponding homopolymer or copolymer is, in the layer sequence shown, expediently, for example, in layer b, c and/or d, in particular in b and/or c, especially in b.

Preference is generally given to a photographic recording material containing a compound of the formula (I) or a corresponding homopolymer or copolymer in a layer above the silver-halide emulsion layer(s). Preference is furthermore given to a photographic recording material containing at least one each of red-sensitive and green-sensitive silver-halide emulsion layers and an interlayer in between, where at least one compound of the formula (I) or a corresponding homopolymer or copolymer is present in the interlayer between the red-sensitive and green-sensitive silver-halide emulsion layers. Very particular preference is given to a photographic recording material containing at least one each of red-sensitive, green-sensitive and blue-sensitive silver-halide emulsion layers and at least two interlayers between said layers and a protection layer, or at least one compound of the formula (I) or a corresponding homopolymer or copolymer is in the layer above the green-sensitive silver-halide emulsion layer, and the silver-halide emulsion layers contain dark-storage and/or light stabilizers.

Essential constituents of the photographic emulsion layers are binders, silver-halide grains and colour couplers.

The binder used is preferably gelatin. However, all or some of this can be replaced by other synthetic, semisynthetic or naturally occurring polymers. Examples of synthetic gelatin replacements are polyvinyl alcohol, poly-N-vinylpyrrolidone, polyacrylamides, polyacrylic acid or derivatives thereof, in particular copolymers thereof. Examples of naturally occurring gelatin replacements are other proteins, such as albumin or casein, cellulose, sugar, starch or alginates. Semisynthetic gelatin replacements are generally modified natural products. Cellulose derivatives, such as hydroxyalkylcellulose, and gelatin derivatives obtained by reaction with alkylating or acylating agents or by grafting-on polymerizable monomers, are examples thereof.

The binders should contain a sufficient amount of functional groups so that sufficiently resistant layers can be produced by reaction with suitable curing agents. Such functional groups are, in particular, amino groups, but also carboxyl groups, hydroxyl groups and active methylene groups.

The gelatin preferably used can be obtained by acidic or alkaline digestion. Oxidized gelatin can also be used. The preparation of such gelatins is described, for example, in The Science and Technology of Gelatin, edited by A. G. Ward and A. Courts, Academic Press 1977, pages 295 ff. The particular gelatin employed should contain the lowest possible content of photographically active impurities (inert gelatin). Gelatins having high viscosity and low swelling are particularly advantageous.

The halide in the silver-halide present in the photographic material as photosensitive constituent can be chloride, bromide or iodide, or a mixture thereof. The halide content of at least one layer can be, for example, from 0 to 15 mol % of iodide, from 0 to 100 mol % of chloride and from 0 to 100 mol % of bromide. The silver bromide iodide emulsions are usually used in the case of colour negative and colour reversal films, and silver chloride bromide emulsions having a high chloride content, for example at least 90 mol % of silver chloride, up to pure silver chloride emulsions are usually used in the case of colour negative and colour reversal paper. The crystals can be predominantly compact, having, for example, regular cubic or octahedral or intermediate forms, but can preferably be platelet-shaped crystals whose mean diameter:thickness ratio is preferably at least 5:1, where the diameter of a grain is defined as the diameter of a circle having an area corresponding to the projected area of the grain. However, the layers can also contain plate-shaped silver-halide crystals in which the diameter:thickness ratio is significantly greater than 5:1, for example from 12:1 to 30:1.

The silver-halide grains can also have a multilayered structure, in the simplest case if inner and outer grain regions (core/shell), the halide composition and/or other modifications, for example doping, differing in the individual grain regions. The mean grain size of the emulsions is preferably from 0.2 µm to 2.0 µm, and the grain size distribution can be either homodisperse or heterodisperse. Homodisperse grain-size distribution means that 95% of the grains have a grain size differing in the mean grain size by not more than ±30%. In addition to the silver halide, the emulsions can also contain organic silver salts, for example silver benzotriazolate or silver behenate.

It is also possible for two or more types of silver-halide emulsion, prepared separately, to be used as a mixture.

The photographic emulsions can be prepared by various methods (for example P. Glafkides, Chimie et Physique, Paul Montel, Paris (1967), G. F. Duffin, Photographic Emulsion Chemistry, The Focal Press, London (1966), V. L. Zelikman et al., Making and Coating Photographic Emulsions, The Focal Press, London (1966), from soluble silver salts and soluble halides.

Precipitation of the silver halide is preferably carried out in the presence of the binder, for example the gelatin, and can be carried out in the acidic, neutral or alkaline pH region, where silver halide complexing agents are preferably used in addition. The latter include, for example, ammonia, thioethers, imidazole, ammonium thiocyanate and excess halide. The water-soluble silver salts and the halides are combined either successively by the single-jet process or simultaneously by the double-jet process or by any combination of the two. Metering with an increasing feed rate is preferred, in which case the "critical" feed rate, at which new nuclei just fail to form, should not be exceeded. The $p_{Ag}$ region can varied within broad limits during the precipitation; the $p_{Ag}$-controlled process is preferably used, in which a certain $p_{Ag}$ value is kept constant or a defined $p_{Ag}$ profile is passed through during the precipitation. In addition to the preferred precipitation in the presence of an excess of halide, however, so-called inverse precipitation in the presence of an excess of silver halide is also possible. Besides by precipitation, the silver-halide crystals can also grow by physical ripening (Ostwald ripening) in the presence of excess halide and/or silver halide complexing agents. The growth of the emulsion nuclei can even take place predominantly by Ostwald ripening, in which case a fine-grained, so-called Lippmann emulsion is preferably mixed with a less-soluble emulsion and redissolved in the latter.

During the precipitation and/or the physical ripening of the silver halide grains, salts or complexes of metals, such as Cd, Zn, Pb, Tl, Bi, Ir, Rh or Fe, can also be present.

Furthermore, the precipitation can also be carried out in the presence of sensitizing dyes. Complexing agents and/or dyes can be deactivated at any desired point in time, for example by changing the pH or by oxidative treatment.

When the crystal formation is complete or at any earlier point, the soluble salts are removed from the emulsion, for example by concentration and washing, by flocculation and washing, by ultra filtration or by ion exchangers.

The silver halide emulsion is generally subjected to chemical sensitization under defined conditions—pH, $p_{Ag}$, temperature, and concentration of gelatin, silver halide and sensitizer—until the sensitivity and fogging optimum has been reached. The procedure is described, for example, in H. Frieser, "Die Grundlagen der Photographischen Prozesse mit Silberhalogeniden" [The Principles of Photographic Processes using Silver Halides], pages 675–734, Akademische Verlagsgesellschaft (1968).

The chemical sensitization can be carried out with addition of compounds of sulfur, selenium, tellurium and/or compounds of metals from sub-group VIII of the Periodic Table (for example gold, palladium and iridium), and furthermore thiocyanate compounds, surface-active compounds, such as thioethers, heterocyclic nitrogen compounds (for example imidazoles and azaindenes) or spectral sensitizers (described, for example, in F. Hamer "The Cyanine Dyes and Related Compounds", 1964, and Ullmanns Encyclopädie der technischen Chemie [Ullmann's Encyclopaedia of Industrial Chemistry], 4th Edition, Vol. 18, pp. 431 ff, and Research Disclosure 17643 (December 1978), Chapter III). Instead of or in addition to the above, reduction sensitization but with addition of reducing agents (tin(II) salts, amines, hydrazine derivatives, aminoboranes, silanes or formamidinesulfinic acid), can be carried out by hydrogen, a low $p_{Ag}$ (for example less than 5) and/or high pH (above 8).

The photographic emulsions can contain compounds for inhibiting fogging or for stabilizing the photographic function during production, storage or photographic processing.

Particularly suitable are azaindenes, preferably tetra- and pentaazaindenes, in particular those substituted by hydroxyl or amino groups. Such compounds have been described, for example, by Birr, Z. Wiss, Phot. 47 (1952), pp. 2–58. It is also possible to use, as antifogging agent, salts of metals such as mercury or cadmium, aromatic sulfonic or sulfinic acids, such as benzenesulfinic acid, or nitrogen-containing heterocyclic compounds, such as nitrobenzimidazole, nitroindazole, substituted or unsubstituted benzotriazoles or benzothiazolium salts. Particularly suitable are heterocyclic compounds containing mercapto groups, for example mercaptobenzothiazoles, mercaptobenzimidazoles, mercaptotetrazoles, mercaptothiadiazoles and mercaptopyrimidines, where these mercaptoazoles also contain a water-solubilizing group, for example a carboxyl group or sulfo group. Other suitable compounds are disclosed in Research Disclosure 17643 (December 1978), Chapter VI.

The stabilizers can be added to the silver-halide emulsions before, during or after their ripening. It is of course also possible to add the compounds to other photographic layers assigned to a silver-halide layer.

It is also possible to use mixtures of two or more of said compounds.

The photographic emulsion layers or other hydrophilic colloid layers of the photosensitive material produced in accordance with the invention can contain surfactants for various purposes, such as coating auxiliaries, for preventing electrical charging, for improving the sliding properties, for emulsification of the dispersion, for preventing adhesion and for improving the photographic characteristics (for example development acceleration, contrast increase, sensitization, etc.). Besides natural surface-active compounds, for example saponin, use is principally made of synthetic surface-active compounds (surfactants); nonionic surfactants, for example alkylene oxide compounds, glycerol compounds or glycidol compounds, cationic surfactants, for example higher alkylamines, quaternary ammonium salts, pyridine compounds and other heterocyclic compounds, sulfonium compounds or phosphonium compounds, anionic surfactants containing an acid group, for example a carboxyl, sulfo, phosphoric acid, sulfate or phosphate group, ampholytic surfactants, for example amino acid and aminosulfonic acid compounds and sulfates or phosphates of an amino alcohol.

The photographic emulsions can be spectrally sensitized using methine or other dyes. Particularly suitable dyes are cyanine dyes, merocyanine dyes and complex merocyanine dyes.

A review of polymethine dyes which are suitable as spectral sensitizers, suitable combinations thereof and supersensitizing combinations is given in Research Disclosure 17643 (December 1978), Chapter IV.

In particular, the following dyes—arranged by spectral region—are suitable:

1. As red sensitizers: 9-ethylcarbocyanines containing benzothiazole, benzoselenazole or naphthothiazole as basic terminal groups, which can be substituted in the 5- and/or 6-position by halogen, methyl, methoxy, carbalkoxy or aryl, and 9-ethylnaphthoxathia- and -selenocarbocyanines and 9-ethylnaphthothiazoxa- and -benzimidazocarbocyanines, provided that the dyes carry at least one sulfoalkyl group of the heterocyclic nitrogen.
2. As green sensitizers 9-ethylcarbocyanines containing benzoxazole, naphthoxazole or a benzoxazole and a benzothiazole as basic terminal groups, and benzimidazocarbocyanines, which can likewise be further substituted and likewise contain at least one sulfoalkyl group on the heterocyclic nitrogen.

3. As blue sensitizers symmetrical or asymmetrical benzimidazo- -oxa-, -thia- or -selenacyanines containing at least one sulfoalkyl group on the heterocyclic nitrogen and, if desired, further substituents on the aromatic ring, and apomerocyanines containing a rhodanine group.

Examples which may be mentioned, in particular for negative and reversal film, are the red sensitizers (RS), green sensitizers (GS) and blue sensitizers (BS) listed below, each of which may be employed individually or in combination with one another, for example RS-1 and RS-2, and GS-1 and GS-2.

RS-1: $R_1$, $R_3$, $R_7$ and $R_9$=H; $R_2$, $R_8$=Cl;
$R_4$=—$SO_3^{\ominus}\oplus NH(C_2H_5)_3$; $R_5$=—$C_2H_5$; $R_6$=—$SO_3^{\ominus}$;
m and n=3; X and Y=S;

RS-2: $R_1$, $R_3$ and $R_9$=H; $R_2$=phenyl; $R_4$=

$$-\underset{\underset{CH_3}{|}}{CH}-SO_3^{\ominus}K^{\oplus};$$

$R_5$=$C_2H_5$; $R_6$=—$SO_3^{\ominus}$; $R_7$, $R_8$=—$OCH_3$; m=2; n=3; X=O; Y=S;

RS-3: $R_1$ and $R_9$=H; $R_2$ and $R_3$ together —CH=CH—CH=CH—;
$R_4$=—$SO_3^{\ominus}Na^{\oplus}$; $R_5$=—$C_2H_5$; $R_6$=—$SO_3^{\ominus}$; $R_7$, $R_8$=Cl;
m and n=3; X=S; Y=N—$C_2H_5$;

RS-4: $R_1$=—$OCH_3$; $R_2$ and $R_8$=—$CH_3$; $R_3$, $R_4$, $R_7$ and $R_9$=H;
$R_5$=—$C_2H_5$; $R_6$=—$SO_3^{\ominus}$; m=2; n=4; X=S; Y=Se;

RS-5: $R_1$ and $R_7$=H; $R_2$ and $R_3$, and $R_8$ and $R_9$ together —CH=CH—CH=CH—; $R_4$=—$SO_3^{\ominus}\oplus NH(C_2H_5)_3$;
$R_5$=$C_2H_5$;
$R_6$=$SO_3^{\ominus}$; m=2; n=3; X and Y=S;

GS-1: $R_1$, $R_3$, $R_7$ and $R_9$=H; $R_2$=phenyl;
$R_4$=

$$-\underset{\underset{CH_3}{|}}{CH}-SO_3^{\ominus}\oplus NH(C_2H_5)_3;$$

$R_5$=—$C_2H_5$; $R_6$=—$SO_3^{\ominus}$;
$R_8$=Cl; m=2; m=3; X and Y=O;

GS-2: $R_1$, $R_2$, $R_7$ and $R_8$=Cl; $R_3$, $R_5$, $R_6$ and $R_9$=H;
$R_4$=

$$-\underset{\underset{CH_3}{|}}{CH}-SO_3^{\ominus};$$

m and n=2; X and Y=N—$C_2H_5$;

GS-3: $R_1$ and $R_7$=H; $R_2$ and $R_3$, and $R_8$ and $R_9$ together —CH=CH—CH=CH—; $R_4$=$SO_3^{\ominus}Na^{\oplus}$; $R_5$=$C_2H_5$;
$R_6$=$SO_3^{\ominus}$; m and n=3; X and Y=O;

GS-4: $R_1$, $R_3$, $R_4$, $R_7$, $R_8$ and $R_9$=H; $R_2$=—$OCH_3$; $R_5$=—$C_2H_5$;
$R_6$=$SO_3^{\ominus}$; m=2; n=4; X=O; Y=S;

BS-1:

BS-2:

wherein in
BS-3: $R_{10}$=

$R_{11}$=—$CH_2COOH$;
BS-4: $R_{10}$=

$R_{11}$=—$C_2H_5$;

Sensitizers can be omitted if the inherent sensitivity of the silver halide is sufficient for a certain spectral region, for example the blue sensitivity of silver bromides.

Non-diffusing monomeric or polymeric colour couplers are assigned to the emulsion layers of various sensitization; these couplers can be in the same layer or in an adjacent layer. Cyan couplers are usually assigned to the red-sensitive layers, magenta couplers to the green-sensitive layers and yellow couplers to the blue-sensitive layers.

Yellow couplers which can be used in the material according to the invention are preferably compounds of the formula A

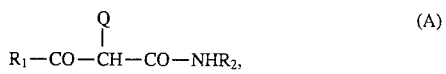

in which $R_1$ is alkyl or aryl, $R_2$ is aryl and Q is hydrogen or a group which can be eliminated by reaction with the oxidised developer.

A group of yellow couplers comprises the compounds of the formula A in which $R_1$ is t-butyl and $R_2$ is a group of the formula

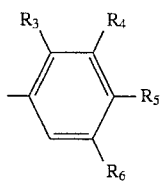

in which $R_3$ is hydrogen, halogen, alkyl or alkoxy, and $R_4$, $R_5$ and $R_6$ are hydrogen, halogen, alkyl, alkenyl, alkoxy, aryl, carboxyl, alkoxycarbonyl, carbamoyl, sulfonyl, sulfamoyl, alkoxysulfonylamino, acylamino, ureido or amino.

Preferably, $R_3$ is chlorine or methoxy, $R_4$ and $R_5$ are hydrogen and $R_6$ is an acylamino group. This group also includes the compounds of the formula

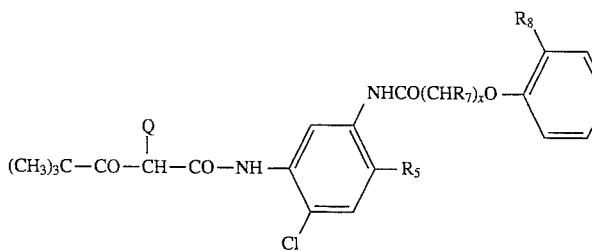

in which x is 0–4, $R_7$ is hydrogen or alkyl, $R_8$ and $R_9$ are alkyl.

Another group of yellow couplers conforms to the formula B

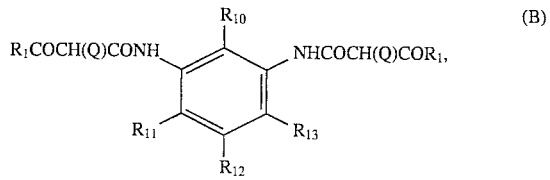

in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, carbamoyl, sulfonyl, sulfamoyl, sulfonamido, acylamino, ureido or amino, and $R_1$ and Q are as defined above.

This group includes compounds of the formula B in which $R_1$ is t-butyl, $R_{10}$ is chlorine, $R_{11}$ and $R_{13}$ are hydrogen, and $R_{12}$ is alkoxycarbonyl.

In the compounds of the formulae A and B, leaving group Q may be hydrogen (tetraequivalent couplers) or a heterocyclic group (diequivalent couplers)

in which $R_{14}$ is a divalent organic group which supplements the ring to make up a 4–7-membered ring, or Q is an —$OR_{15}$ group in which $R_{15}$ is alkyl, aryl, acyl or a heterocyclic radical.

Typical examples of customary yellow couplers are the compounds of the formulae below:

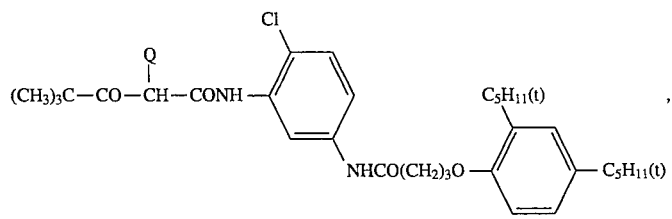
wherein
a) 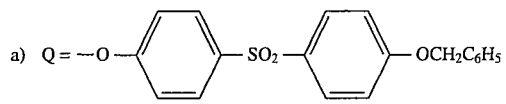
b) 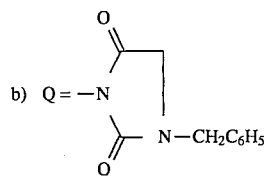
c) 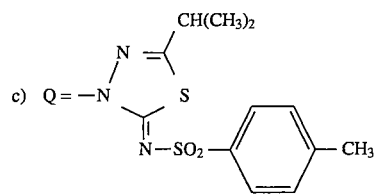
d) 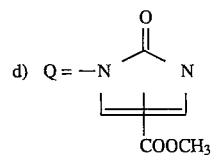
e) 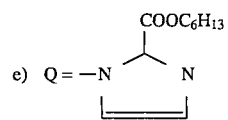
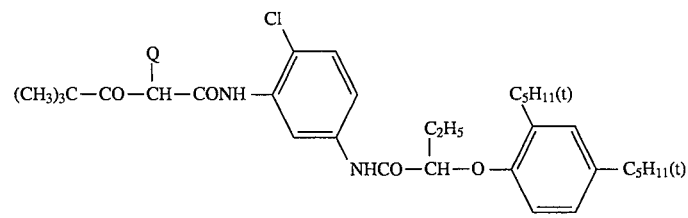
f) 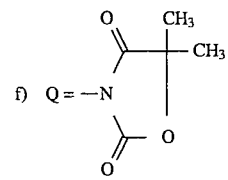
g) 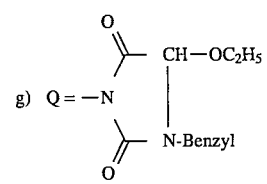

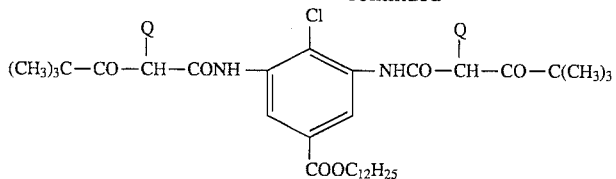
h) 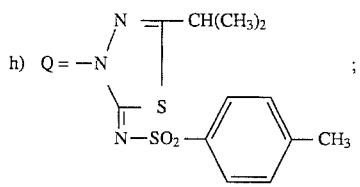
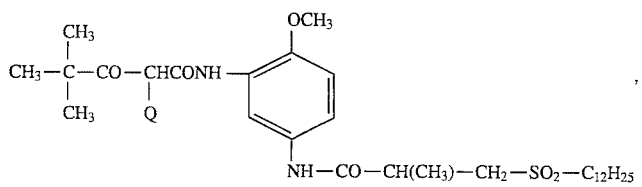
wherein
i) 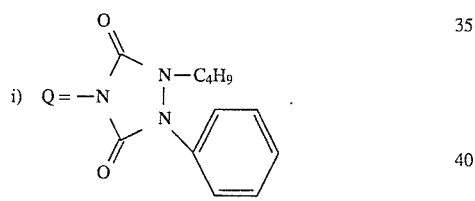
Further examples of yellow couplers are given in U.S. Pat. Nos. 2,407,210, 2,778,658, 2,875,057, 2,908,573, 3,227,155, 3,227,550, 3,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752, 4,022,620, 5,118,599, 5,215,878, 5,260,182, 5,294,527, 5,298,383, 5,300,412, 5,306,609, 5,314,797 and 5,336,591 in DE-A 1,547,868, 2,057,941, 2,162,899, 2,163,813, 2,213,461, 2,219,917, 2,261,361, 2,261,362, 2,263,875, 2,329,587, 2,414,006 and 2,422,812, in GB-A 1,425,020 and 1,077,874 and in JP-A-88/123 047, U.S. Pat. Nos. 4 133 052, 5 080 469 and 5 313 323, and in EP-A 447 969, 447,969, 508 398, 510 535, 542 463 and 568 198.
The yellow couplers are usually used in an amount of 0.05–2 mol and preferably 0.1–1 mol per mol of silver halide.
Typical and preferred yellow couplers conform to the formulae:

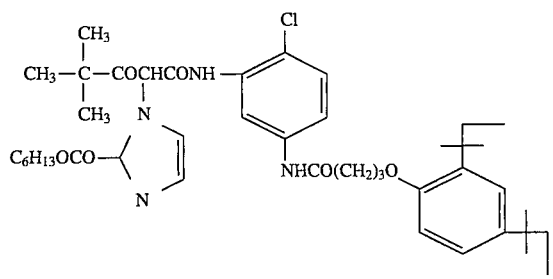
(Y-1)
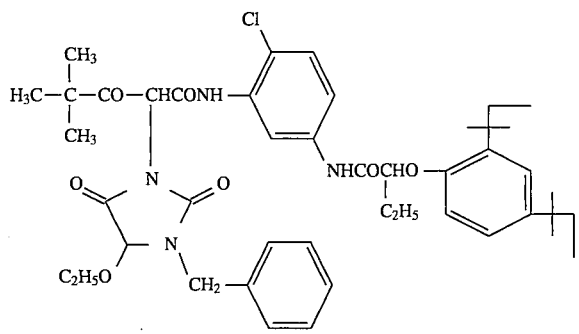
(Y-2)
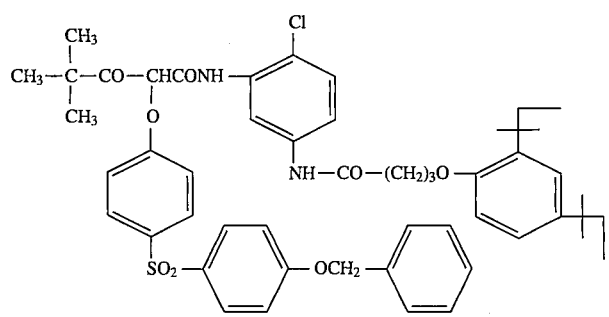
(Y-3)
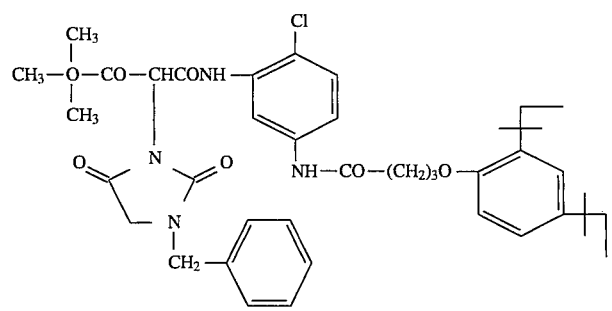
(Y-4)
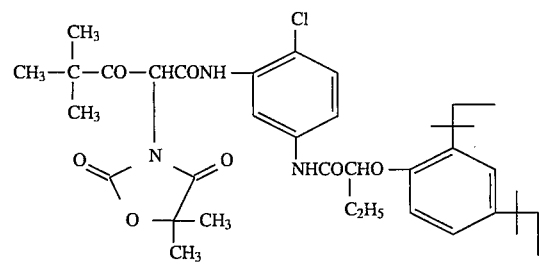
(Y-5)
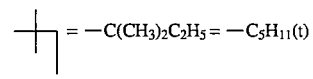

(Y-6)
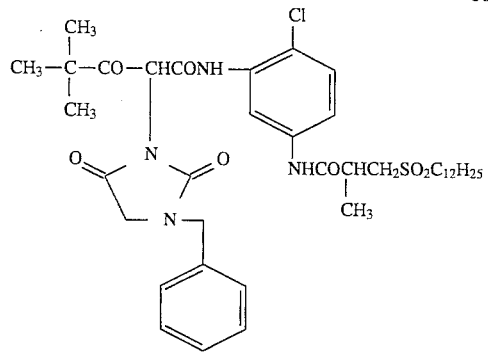
(Y-7)
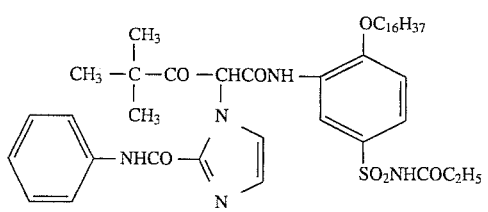
(Y-8)
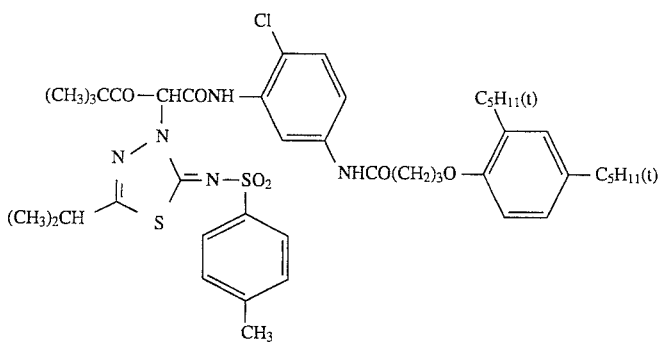
(Y-9)
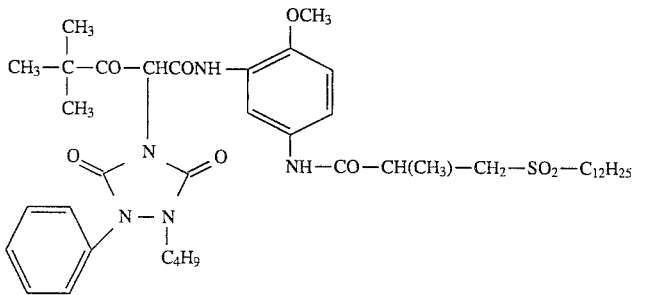
(Y-10)
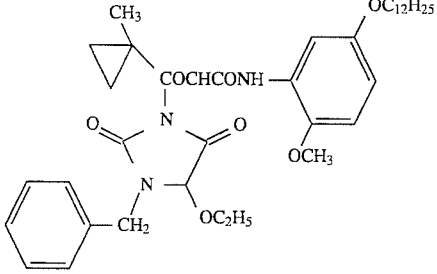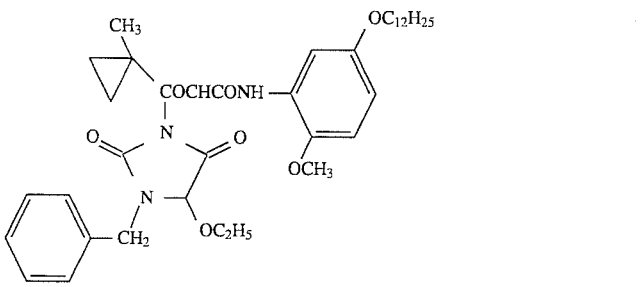

-continued
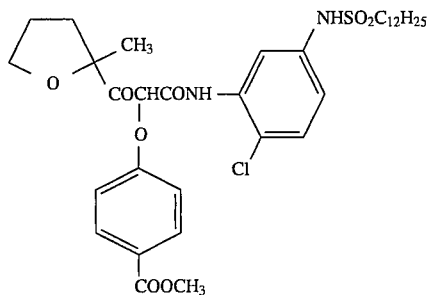
(Y-11)
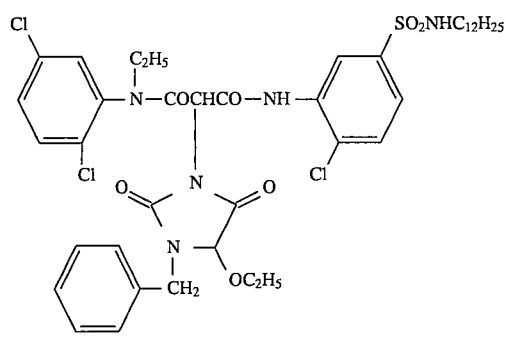
(Y-12)
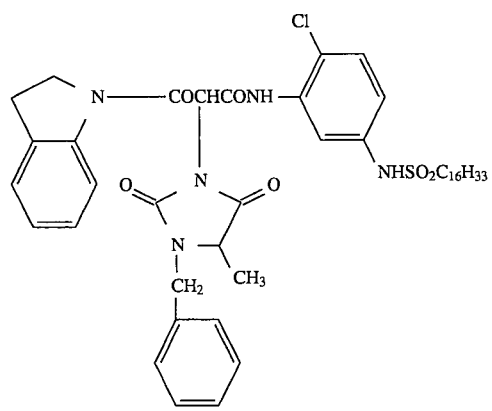
(Y-13)
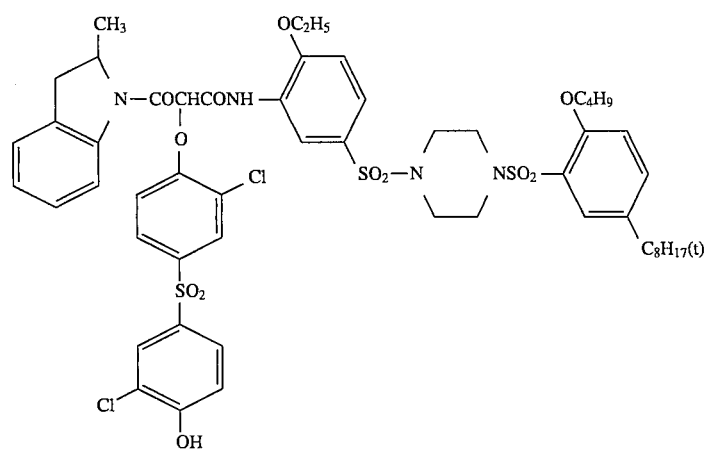
(Y-14)

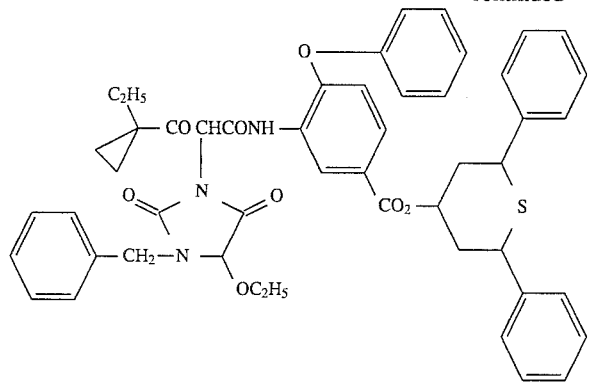
(Y-15)
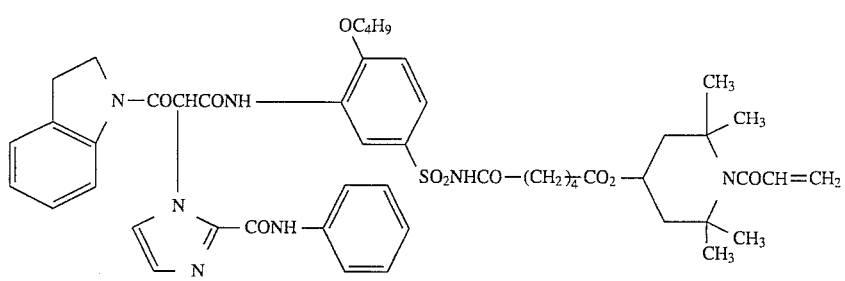
(Y-16)
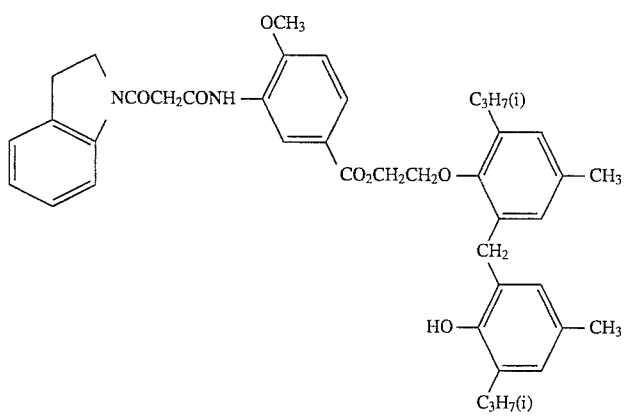
(Y-17)
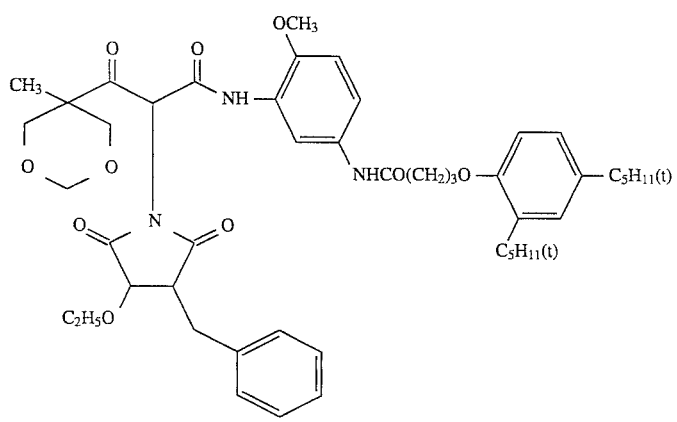
(Y-18)

-continued (Y-19)

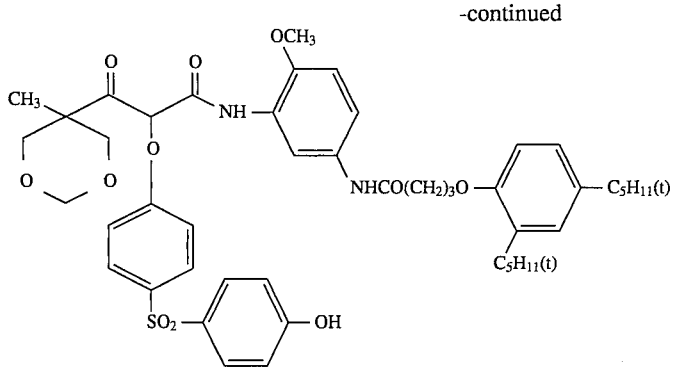

Examples of magenta couplers are simple 1-aryl-5-pyrazolones or pyrazole derivatives which have been condensed with 5-membered hetero rings, e.g. imidazopyrazoles, pyrazolopyrazoles, pyrazolotriazoles and pyrazolotetrazoles.

One group of magenta couplers comprises 5-pyrazolones of the formula C

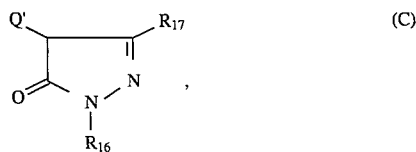

(C)

as described in British Patent 2 003 473. In this formula, $R_{16}$ is hydrogen, alkyl, aryl, alkenyl or a heterocyclic group and $R_{17}$ is hydrogen, alkyl, aryl, a heterocyclic group, an ester group, an alkoxy group, an alkylthio group, a carboxyl group, an arylamino group, an acylamino group, a (thio)urea group, a (thio)carbamoyl group, a guanidino group or a sulfonamido group.

$R_{17}$ is preferably an

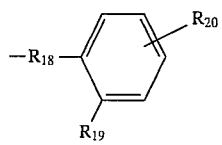

group, in which $R_{18}$ is imino, acylamino or ureido, $R_{19}$ is hydrogen, halogen, alkyl or alkoxy and $R_{20}$ is hydrogen, alkyl, acylamino, carbamoyl, sulfamoyl, sulfonamido, alkoxycarbonyl, acyloxy or a urethane group.

If Q' is hydrogen, the magenta coupler is tetraequivalent with respect to the silver halide.

Typical examples of magenta couplers of this type are compounds of the formula

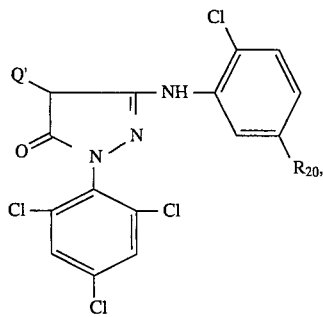

in which $R_{20}$ is as defined above, and Q', as described above, is a leaving group. These compounds are preferably present in the material according to the invention.

Further examples of tetraequivalent magenta couplers of this type are given in U.S. Pat. Nos. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500 and JP-A-89/309 058.

If Q' in the formula C is not hydrogen, but instead a group which is eliminated during the reaction with the oxidised developer, the magenta coupler is diequivalent. In this case, Q can be, for example, halogen or a group bonded to the pyrazole ring via O, S or N. Diequivalent couplers of this type give greater colour density and are more reactive towards the oxidised developer than are the corresponding tetraequivalent magenta couplers.

Examples of diequivalent magenta couplers are described in U.S. Pat. Nos. 3,006,579, 3,419 391, 3,311,476, 3,432, 521, 3,214,437, 4,032,346, 3,701,783, 4,351,897, 3,227,554, 3,262,292. in EP-A-133 503, 529 784, 530 039, DE-A-2 944 601, JP-A-78/34 044, 74/53 435, 74/53 436, 75/53 372 and 75/122 935, 3 323 851, 4 018 547 and 5 150 429 and WO 93/02 392.

Typical and preferred magenta couplers conform to the formulae:

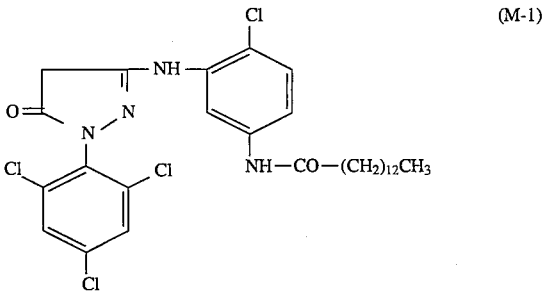

(M-1)

-continued

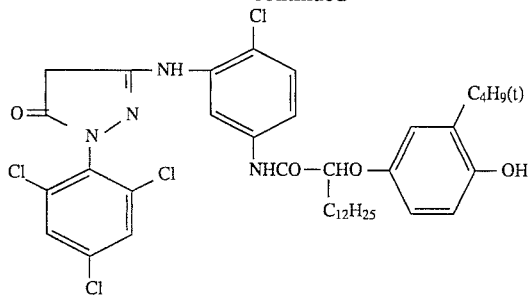 (M-2)

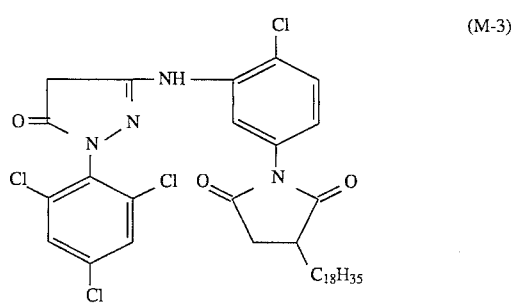 (M-3)

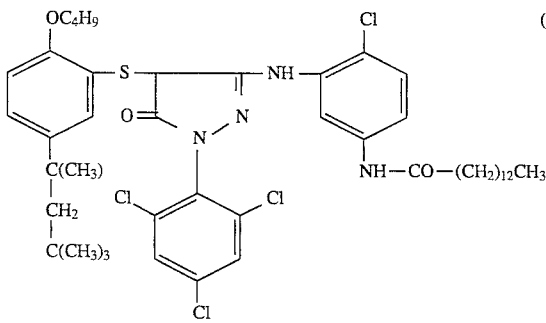 (M-4)

It is possible for 2 pyrazolone rings to be linked via a divalent Q', giving so-called bis-couplers. These are described, for example, in U.S. Pat. Nos. 2,632,702, 2,618, 864, GB-A-968 461, GB-A-786 859, JP-A-76/37 646, 59/4 086, 69/16 110, 69/26 589, 74/37 854 and 74/29 638. Y is preferably an O-alkoxyarylthio group.

As mentioned above, the magenta couplers used can also be pyrazoles condensed with 5-membered heterocyclic rings, known as pyrazoloazoles. Their advantages over simple pyrazoles is that they have colours of greater formalin resistance and have purer absorption spectra.

Magenta couplers of the pyrazoloazole type, which are likewise preferred, may be represented by the formula D

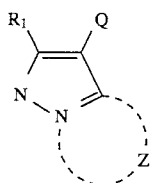 D in which $R_1$ is hydrogen or a substituent, Z represents the non-metallic atoms necessary to complete a 5-membered ring containing 2 or 3 nitrogen atoms, it being possible for this ring to be substituted, and Q is hydrogen (tetraequivalent couplers) or a leaving group (diequivalent couplers).

Of these compounds, preference is given to magenta couplers of the formulae

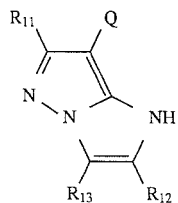 (D-1)

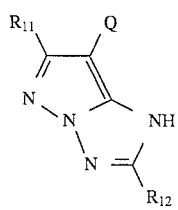 (D-2)

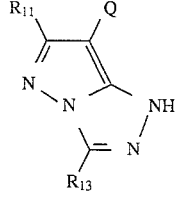 (D-3)

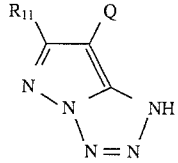 (D-4)

$R_{11}$, $R_{12}$ and $R_{13}$, independently of one another, are, for example, hydrogen; halogen (for example chlorine or bromine), —$CR_3$ in which the radicals $R_3$ are, independently of one another, hydrogen or alkyl, aralkyl, alkenyl, alkynyl, cycloalkyl or cycloalkenyl, particularly preferably methyl, ethyl, propyl, isopropyl, t-butyl, tridecyl, 2-methanesulfonylethyl, 3-(3-pentadecylphenoxy)propyl, 3-(4-(2-(4-(4-hydroxyphenylsulfonyl)phenoxy) dodecanamido) phenyl)propyl, 2-ethoxytridecyl, trifluoromethyl, cyclopentyl, 3-(2,4-di-t-amylphenoxy)propyl; aryl (for example phenyl, 4-butylphenyl, 2,4-di-t-amylphenyl or 4-tetradecaneamidophenyl); heterocyclyl (for example 2-furyl, 2-thienyl, 2-pyrimidinyl or 2-benzothiazolyl); cyano; hydroxyl, nitro; carboxyl; amino; alkoxy (for example methoxy, ethoxy, 2-methoxyethoxy; 2-dodecylethoxy, 2-methanesulfonylethoxy); aryloxy (for example phenoxy, 2-methylphenoxy, 4-t-butylphenoxy, 3-nitrophenoxy, 3-t-butyloxycarbamoylphenoxy or 3-methoxycarbamoyl); acylamino (for example acetoamido, benzamido, tetradecaneamido, 2-(2,4-di-t-amylphenoxy)butaneamido, 4-(3-t-butyl-4-hydroxyphenoxy)butaneamido or 2-(4-(4-hydroxyphenylsulfonyl)phenoxy)decanamido); methylbutylamino; anilino (for example phenylamino, 2-chloroanilino, 2-chloro-5-tetradecaneaminoanilino, 2-chloro-5-dodecyloxycarbonylanilino, N-acetylanilino or 2-chloro-5-(alpha-(3-t-butyl-4-hydroxyphenoxy)dodecaneamidoanilino)); ureido (for example phenylureido, methylureido or N,N-dibutylureido); sulfamoylamino (for example N,N-dipropylsulfamoylamino or N-methyl-N-decylsulfamoylamino); alkylthio (for example methylthio, octylthio, tetradecylthio, 2-phenoxyethylthio, 3-phenoxypropylthio or 3-(4-t-butylphenoxy)propylthio); arylthio (for example phenylthio, 2-butoxy-5-t-octylphenylthio, 3-pentadecylphenylthio, 2-carboxyphenylthio or 4-tetradecaneamidophenylthio); alkoxycarbonylamino (for example methoxycarbonylamino or tetradecyloxycarbonylamino); sulfonamido (for example methanesulfonamido, hexadecanesulfonamido, benzenesulfonamido, p-toluenesulfonamido, octadecanesulfonamido or 2-methoxy-5-t-butylbenzenesulfonamido); carbamoyl (for example N-ethylcarbamoyl, N,N-dibutylcarbamoyl, N-(2-dodecyloxyethyl)carbamoyl, N-methyl-N-dodecylcarbamoyl or N-(3-(2,4-di-t-amylphenoxy)propyl)carbamoyl); sulfamoyl (for example N-ethylsulfamoyl, N,N-dipropylsulfamoyl, N-2-(dodecyloxyethyl)sulfamoyl, N-ethyl-N-dodecylsulfamoyl or N,N-diethylsulfamoyl); sulfonyl (for example methanesulfonyl, octanesulfonyl, benzenesulfonyl or toluenesulfonyl); alkoxycarbonyl (for example methoxycarbonyl, butoxycarbonyl, dodecyloxycarbonyl or octadecyloxycarbonyl); heterocyclyloxy (for example 1-phenyltetrazol-5-oxy or 2-tetrahydropyranyloxy); azo (for example phenylazo, 4-methoxyphenylazo, 4-pivaloylaminophenylazo or 2-hydroxy-4-propanoylphenylazo); acyloxy (for example acetoxy); carbamoyloxy (for example N-methylcarbamoyloxy or N-phenylcarbamoyloxy); silyloxy (for example trimethylsilyloxy or dibutylmethylsilyloxy); aryloxycarbonylamino (for example phenoxycarbonylamino); imido (for example N-succinimido, N-phthalimido or 3-octadecenylsuccinimido); heterocyclylthio (for example 2-benzothiazolylthio, 2,4-diphenyloxy-1,3,5-triazole-6-thio or 2-pyridylthio); sulfinyl (for example dodecanesulfinyl, 3-pentadecylphenylsulfinyl or 3-phenoxypropylsulfinyl); phosphonyl (for example phenoxyphosphonyl, octyloxyphosphonyl or phenylphosphonyl); aryloxycarbonyl (for example phenoxycarbonyl); acyl (for example acetyl, 3-phenylpropanoyl, benzoyl or 4-dodecyloxybenzoyl); or azolyl (for example imidazolyl, pyrazolyl or 3-chloro-pyrazol-1-yl).

These substituents may be further substituted, for example by halogen or by an organic radical bonded via a C, O, N or S atom.

Preferred groups $R_{11}$ are alkyl, aryl, alkoxy, aryloxy, alkylthio, ureido, urethane and acylamino groups.

$R_{12}$ may be as defined for $R_{11}$ and is preferably hydrogen, alkyl, aryl, a heterocyclic ring, alkoxycarbonyl, carbamoyl, sulfamoyl, sulfinyl, acyl or cyano.

$R_{13}$ may be as defined for $R_{11}$ and is preferably hydrogen, alkyl, aryl, a heterocyclic ring, alkoxy, aryloxy, alkylthio, arylthio, alkoxycarbonyl, carbamoyl or acyl, in particular alkyl, aryl, a heterocyclic ring, alkylthio or arylthio.

Q is hydrogen or a leaving group, such as halogen, alkoxy, aryloxy, acyloxy, alkyl- or arylsulfonyloxy, acylamino, alkyl- or arylsulfonamido, alkoxycarbonyloxy, aryloxy-carbonyloxy, alkyl-, aryl- or heterocyclyl-S-carbamoylamino, a 5- or 6-membered, nitrogen-containing heterocyclic radical, imido or arylazo. These groups may be further substituted as indicated for $R_{11}$.

Q is preferably halogen (for example fluorine, chlorine or bromine); alkoxy (for example ethoxy, dodecyloxy, methoxyethylcarbamoylmethoxy, carboxypropoxy, methylsulfonylethoxy or ethoxycarbonylmethoxy); aryloxy (for example 4-methylphenoxy, 4-chlorophenoxy, 4-methoxyphenoxy, 4-carboxyphenoxy, 3-ethoxycarboxyphenoxy, 3-acetylaminophenoxy or 2-carboxyphenoxy); acyloxy (for example acetoxy, tetradecanoyloxy or benzoyloxy); alkyl- or arylsulfonyloxy (for example methanesulfonyloxy or toluenesulfonyloxy); acylamino (for example dichloroacetylamino or heptafluorobutyrylamino); alkyl- or arylsulfonamido (for example methanesulfonamido, trifluoromethanesulfonamido or p-toluenesulfonamido); alkoxycarbonyloxy (for example ethoxycarbonyloxy or benzyloxycarbonyloxy); aryloxycarbonyloxy (for example phenoxycarbonyloxy); alkyl-, aryl- or heterocyclyl-S- (for example dodecylthio, 1-carboxydodecylthio, phenylthio, 2-butoxy-5-t-octylphenylthio or tetrazolylthio); carbamoylamino (for example N-methylcarbamoylamino or N-phenylcarbamoylamino); a 5- or 6-membered, nitrogen-containing ring (for example imidazolyl, pyrazolyl, triazolyl, tetrazolyl or 1,2-dihydro-2-oxo-1-pyridyl); imido (for example succinimido or hydantoinyl); or arylazo (for example phenylazo or 4-methoxyphenylazo).

Q may alternatively form corresponding bis-compounds by condensation of tetraequivalent couplers with an aldehyde or ketone. Furthermore, Q may contain photographically active groups, such as development inhibitors or development accelerators. Q is preferably halogen, alkoxy, aryloxy, alkyl- or arylthio, or a 5- or 6-membered, nitrogen-containing, heterocyclic group which is bonded to the coupling site via a nitrogen atom.

Pyrazolotetrazoles are described in JP-A-85/33 552; pyrazolopyrazoles in JP-A-85/43 695; pyrazoloimidazoles in JP-A-85/35 732, JP-A-86/18 949 and U.S. Pat. No. 4,500, 630; pyrazolotriazoles in JP-A-85/186 567, JP-A-86/47 957, JP-A-85/215 687, JP-A-85/197 688, JP-A-85/172 982, EP-A-119 860, EP-A-173 256, EP-A-178 789, EP-A-178 788 and in Research Disclosure 84/24 624.

Further pyrazoloazole magenta couplers are described in: JP-A-86/28 947, JP-A-85/140 241, JP-A-85/262 160, JP-A-85/213 937, JP-A-87/278 552, JP-A-87/279 340, JP-A-88/100 457, JP-A-5 027 391, JP-A-5 053 271, JP-A-5 053 272, JP-A-232 646, JP-A-5 241 286, JP-A-5 241 287, JP-A-5 241 288, JP-A-5 241 289, JP-A-5 241 290, JP-A-5 249 633, JP-A-5 3033181, JP-A-5 323 530, EP-A-177 765, EP-A-176 804, EP-A-170 164, EP-A-164 130, EP-A-178 794, EP-A-0 487 081, EP-A-0 489 333, EP-A-0 558 145, EP-A-0 568 894, DE-A-3 516 996, DE-A-3 508 766, DE-A-4 240 000, WO 92/10 788, WO 92/12 464, U.S. Pat. Nos. 5,100,772, 5,254,451, 5,300,407, 5,336,593 and Research Disclosure 81/20 919, 84/24 531 and 85/25 758.

Examples of suitable couplers of this type are:

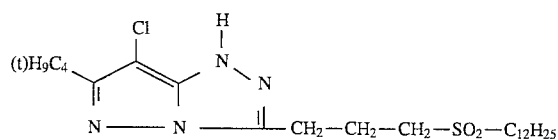 (M-5)
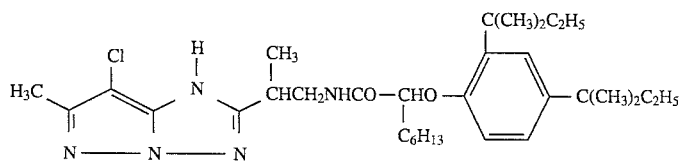 (M-6)
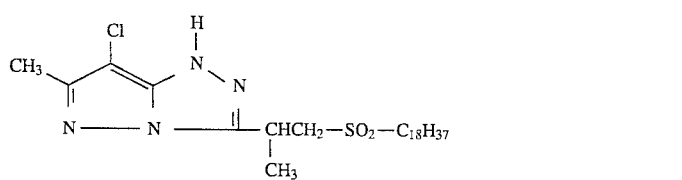 (M-7)
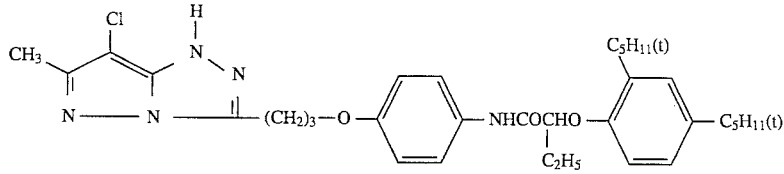 (M-8)
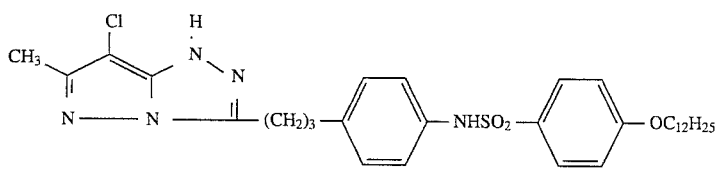
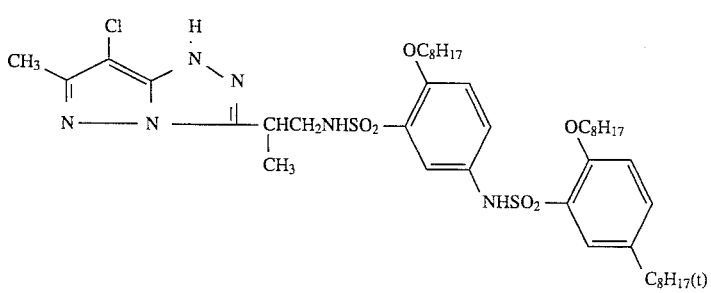
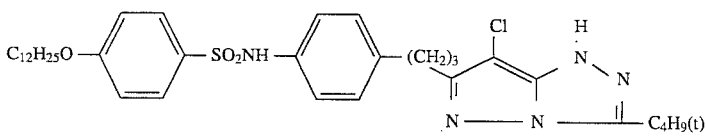
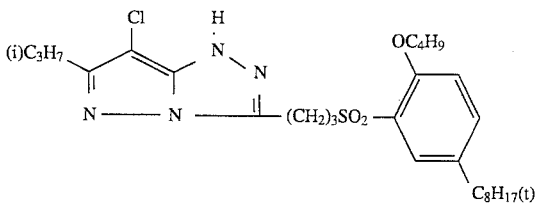

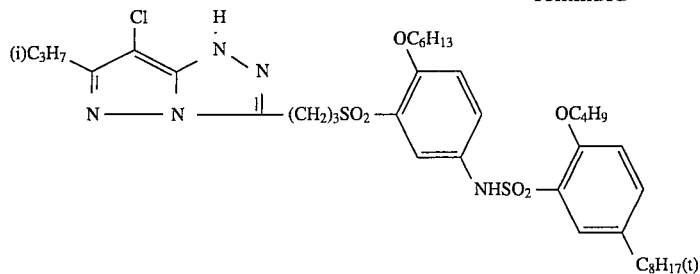
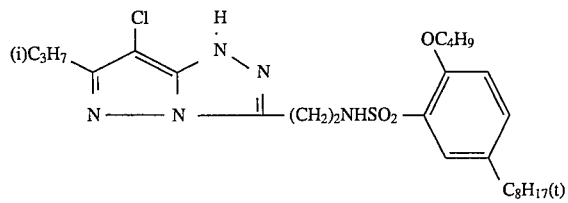
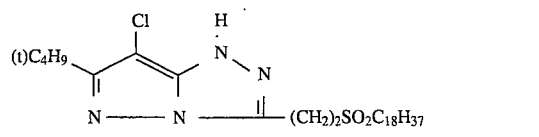
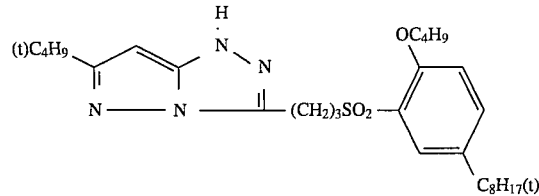
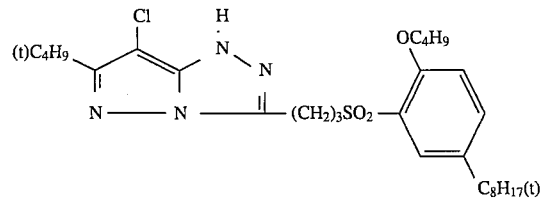
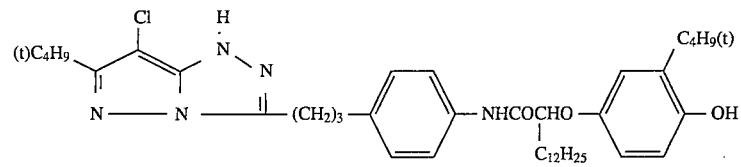
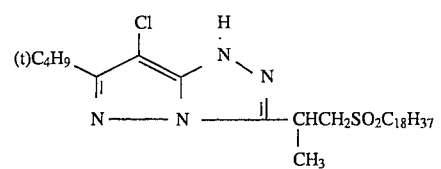
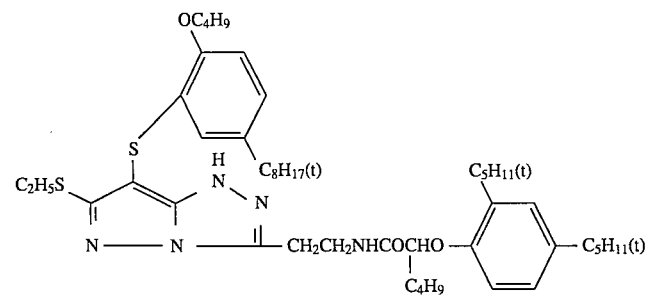

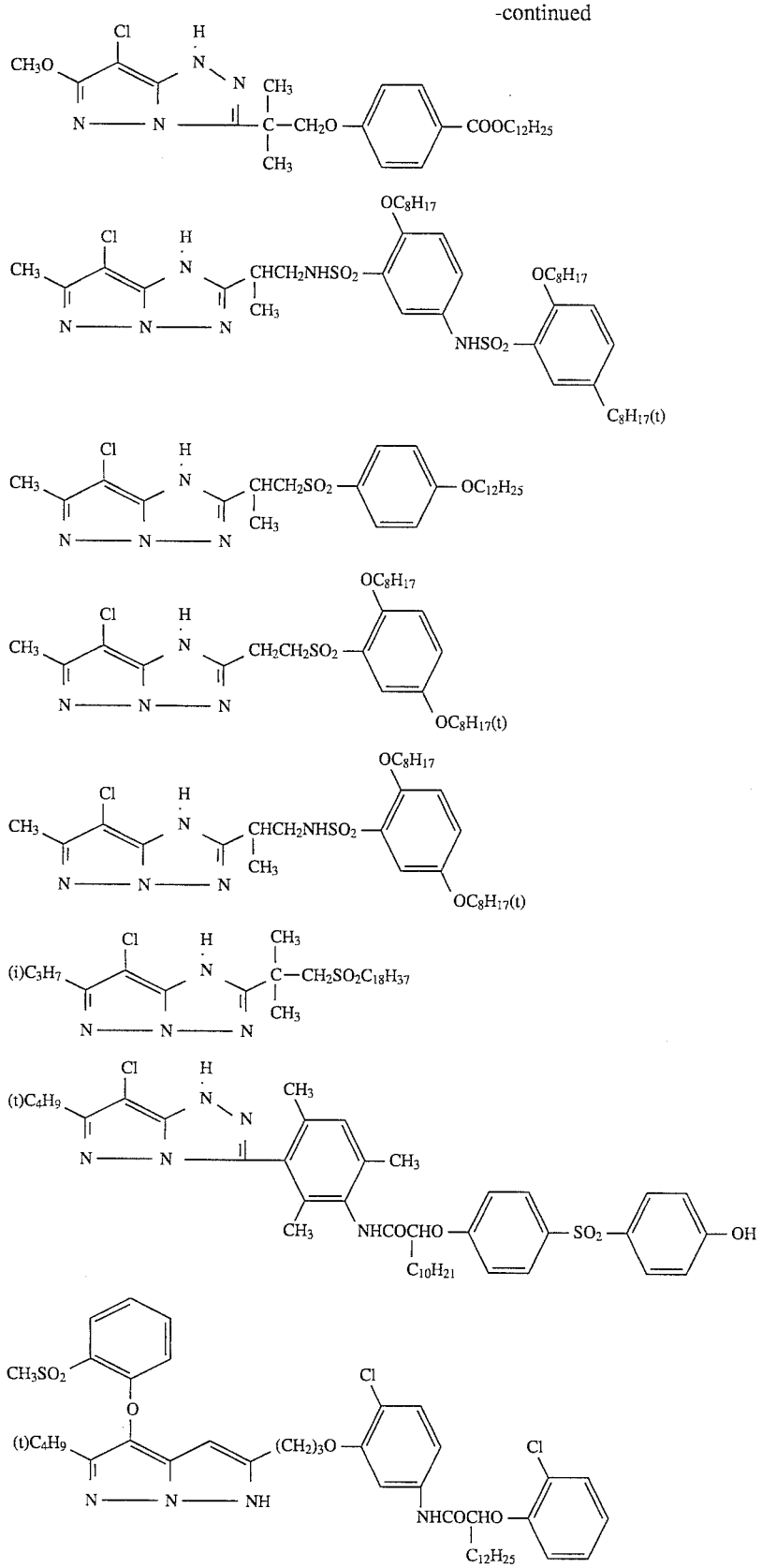

-continued
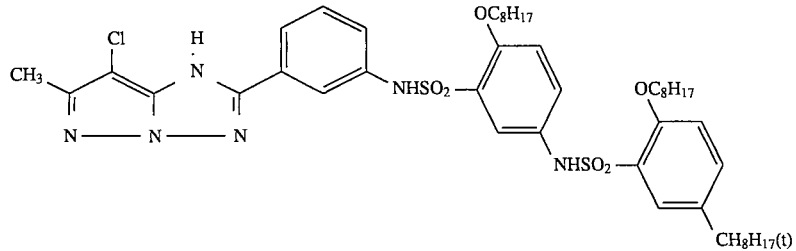
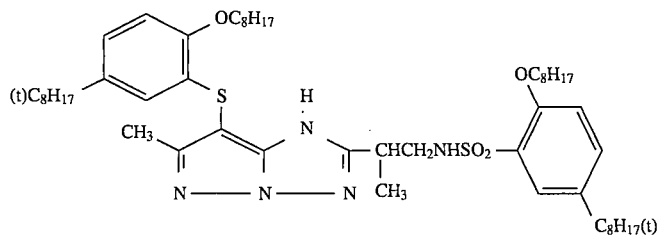
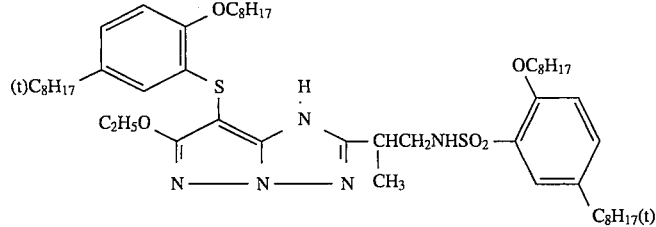
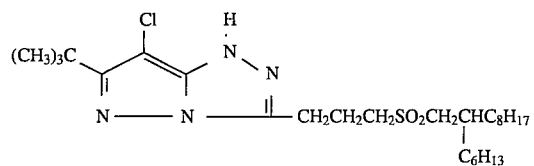
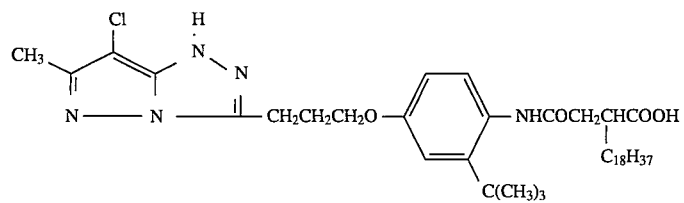
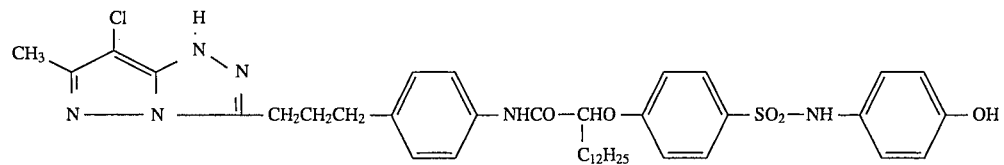
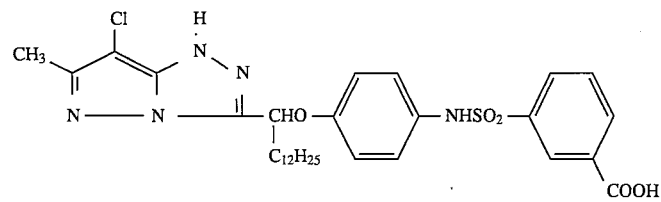

-continued
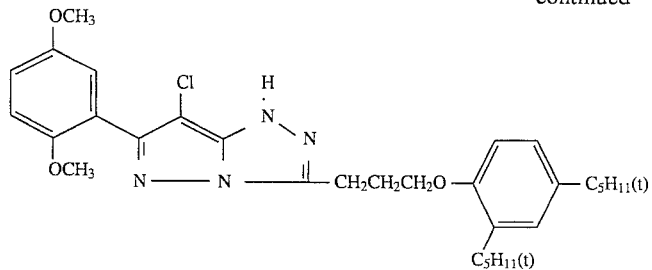
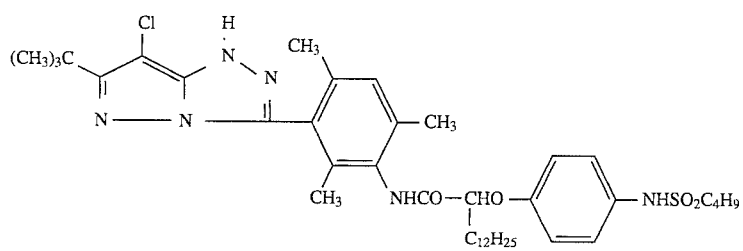
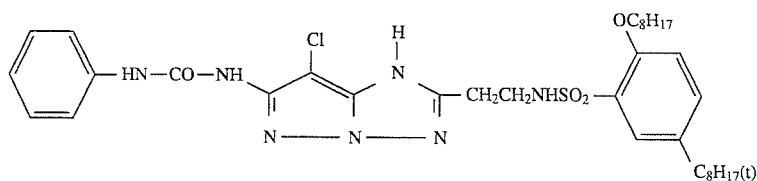
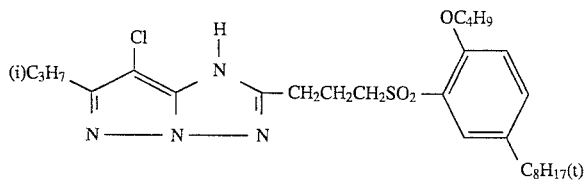
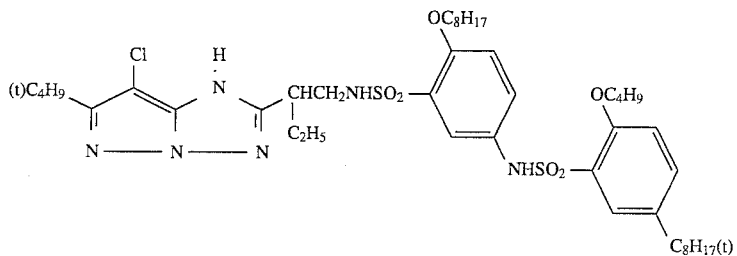
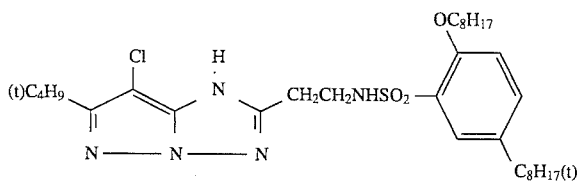
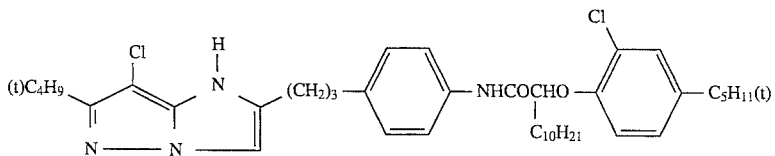
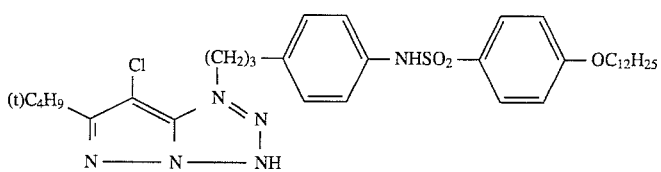

-continued
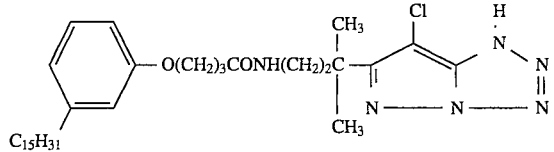
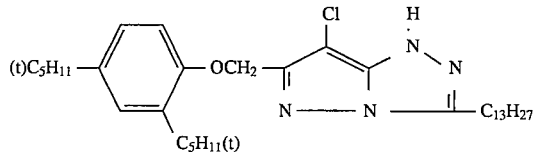
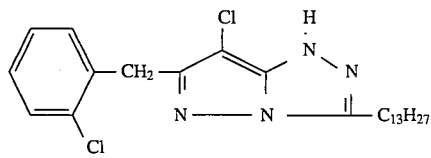
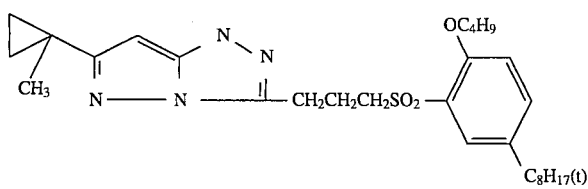
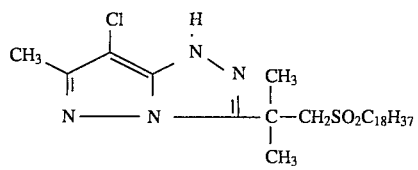
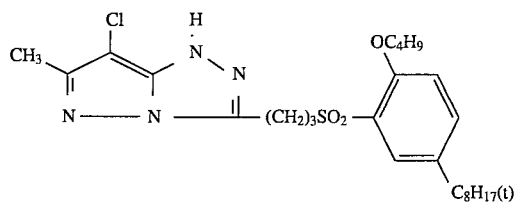
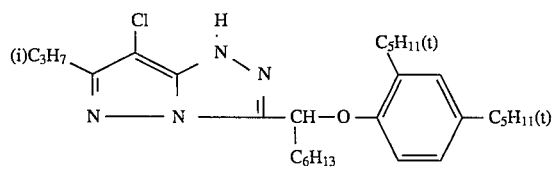
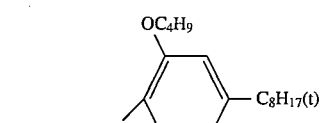
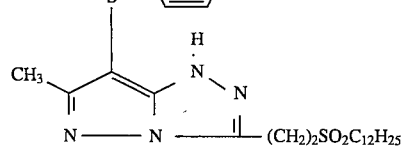
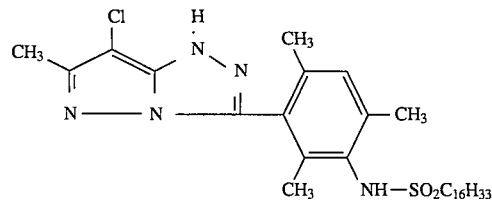

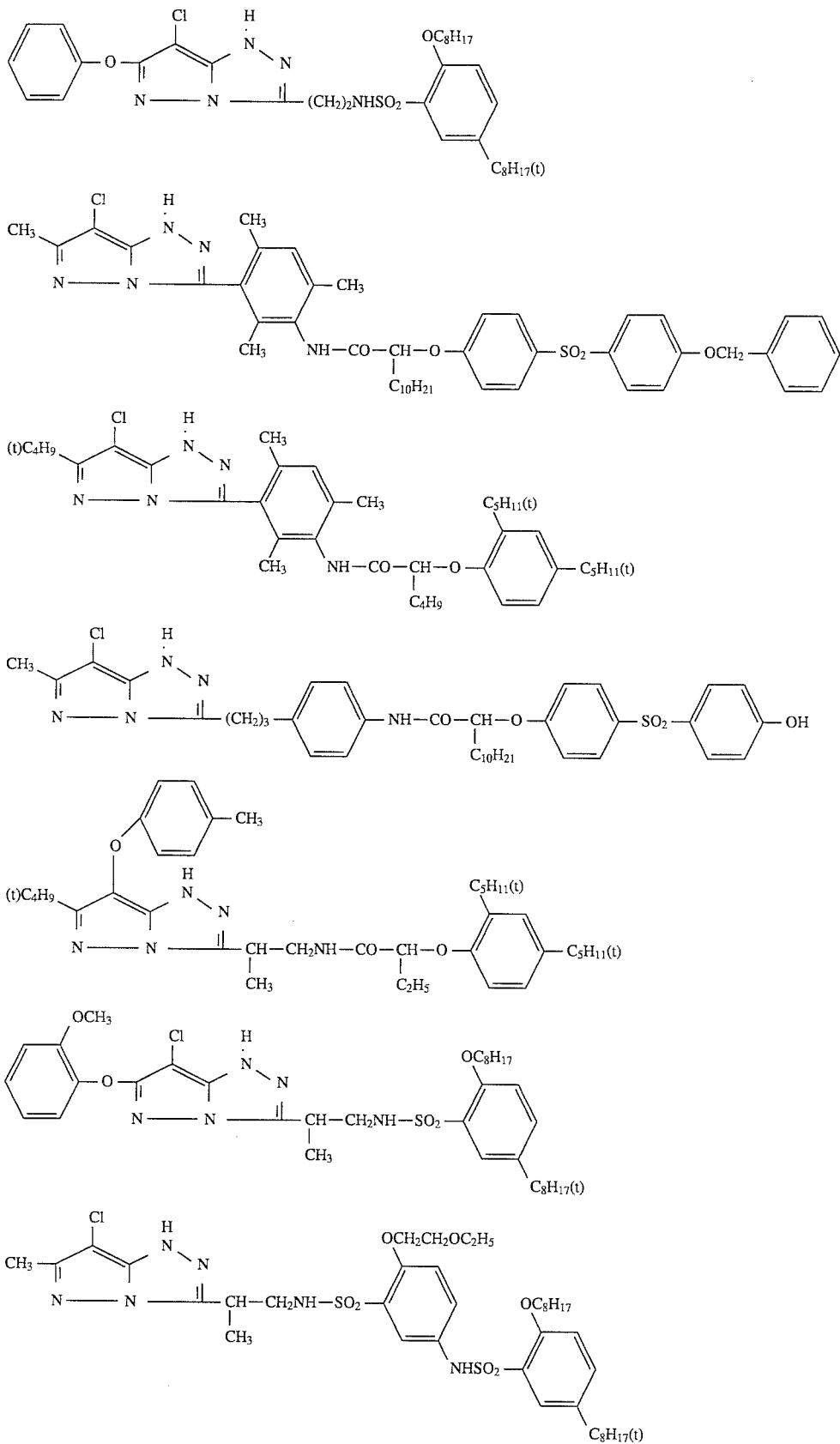

-continued
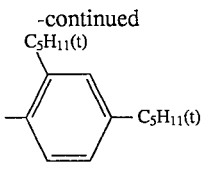
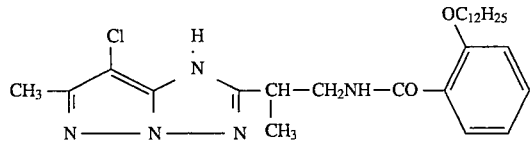
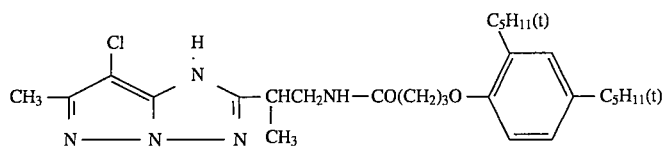
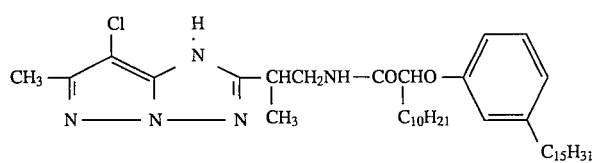
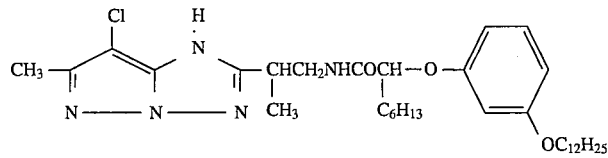
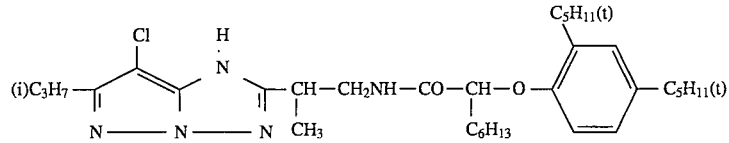
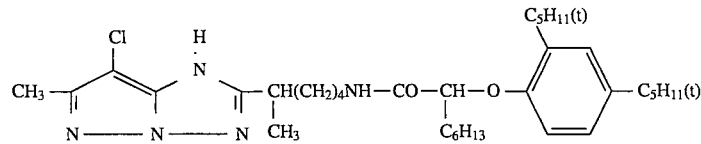
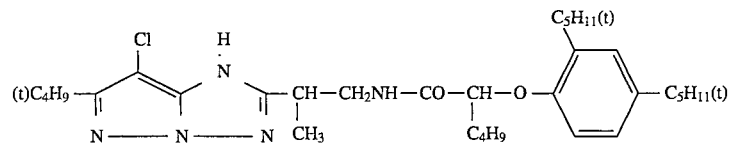
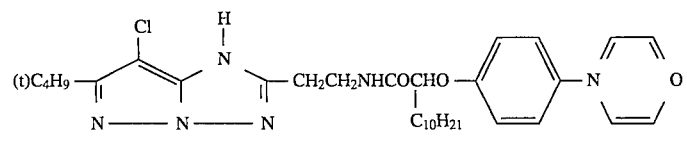
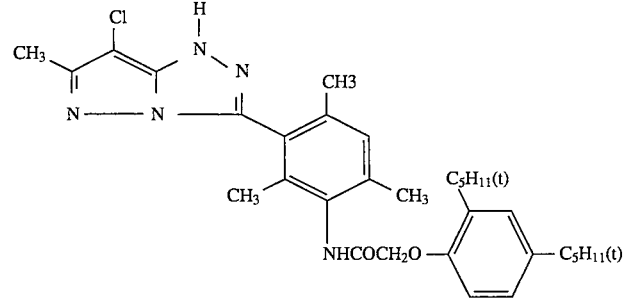

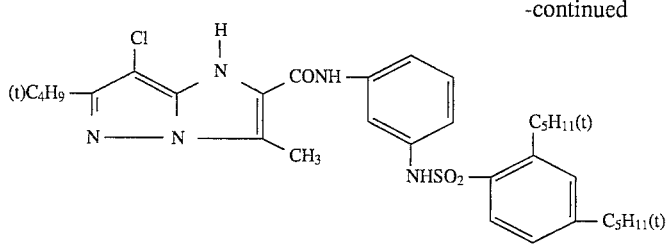

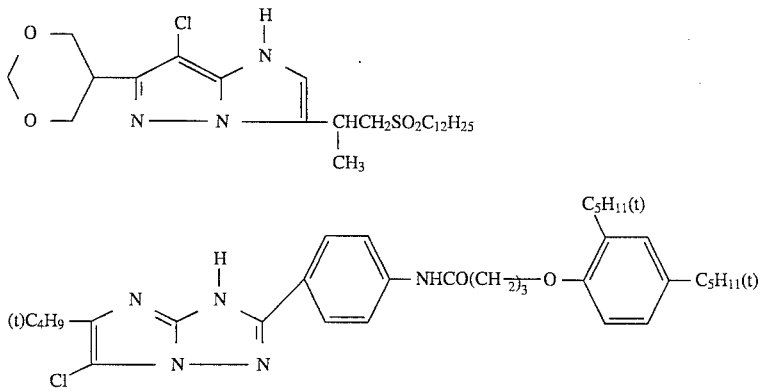

Cyan couplers may be, for example, derivatives of phenol, of 1-naphthol or of pyrazoloquinazolone. Preference is given to structures of the formula E

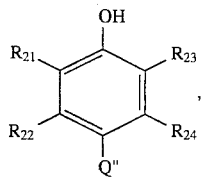

in which $R_{21}$, $R_{22}$, $R_{23}$ and $R_{24}$ are hydrogen, halogen, alkyl, carbamoyl, amino, sulfonamido, phosphoramido or ureido. $R_{21}$ is preferably H or Cl, $R_{22}$ is preferably an alkyl or amino group, $R_{23}$ is preferably an amino group and $R_{24}$ is preferably hydrogen. Q" is hydrogen (tetraequivalent couplers) or a leaving group (diequivalent couplers) which can be eliminated during the reaction with the oxidised developer. A detailed list of cyan couplers is given in U.S. Pat. No. 4,456,681.

The red-sensitive silver-halide emulsion layer of the material according to the invention preferably contains a cyan coupler of the formula

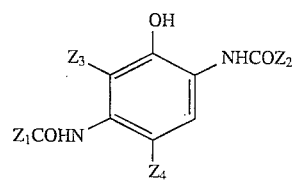

and/or of the formula

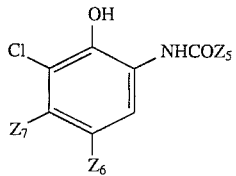

in which $Z_1$ is alkyl or aryl, $Z_2$ is alkyl, cycloalkyl, aryl, a heterocyclic group or a ballast group, $Z_3$ is hydrogen or halogen, $Z_1$ and $Z_3$ together can form a ring, and $Z_4$ is hydrogen or a leaving group, and $Z_5$ is a ballast group, $Z_6$ is hydrogen or a leaving group and $Z_7$ is alkyl.

Examples of customary cyan couplers are the following:

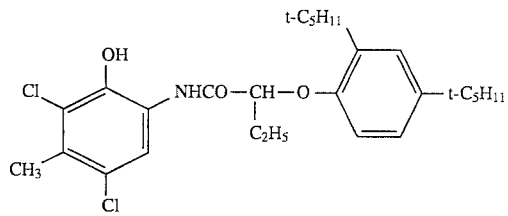

-continued
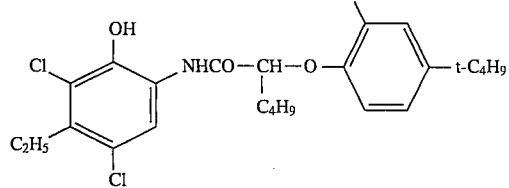 (E-2)
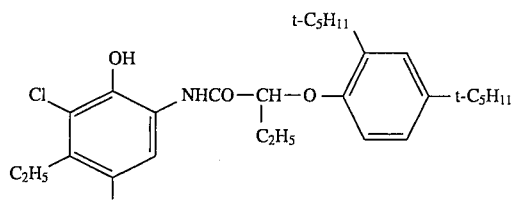 (E-3)
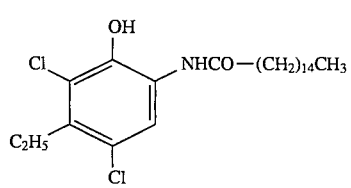 (E-4)
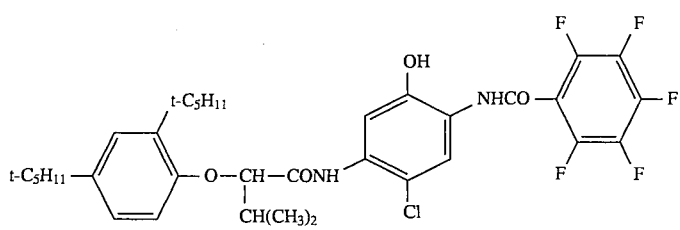 (E-5)
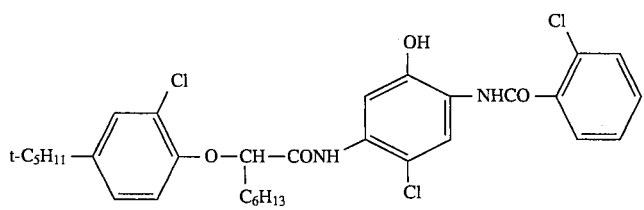 (E-6)
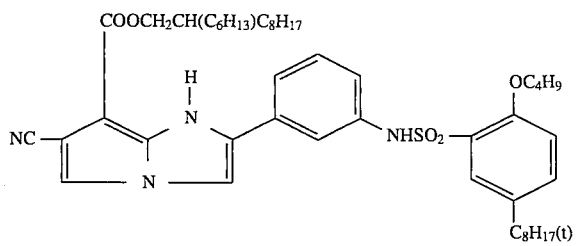 (E-7)
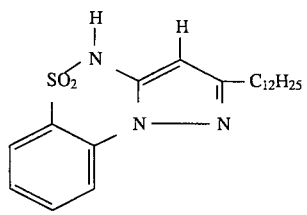 (E-8)
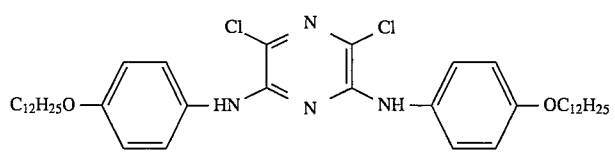 (E-9)

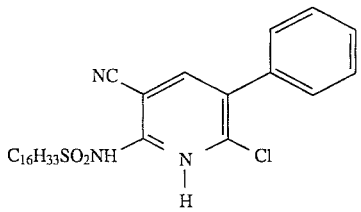
(E-10)

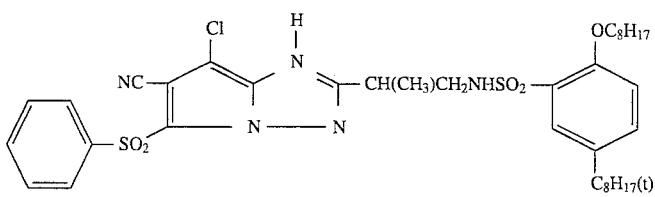
(E-11)

Further examples of cyan couplers are given in the following: U.S. Pat. Nos. 2,369,929, 2,423,730, 2,434,272, 2,474 293, 2,521,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086, 4,456,681, 4,873,183, 4,923,791, 5,143,824, 5,256,526, 5,269,181, 5,262,293, 5,270,153 and 5,306,610 and in EP-A-354 549 and EP-A-398 664, EP-A-0 456 226, EP-A-0 484 909, EP-A-0 487 111, EP-A-0 488 248, EP-A-0 491 197, EP-A-0 544 316, EP-A-0 545 300, EP-A-0 545 305, EP-A-0 556 777, EP-A-0 578 248 and EP-A-0 608 133 and JP-A-3 240 053, 3 284 746, 4 009 050, 4 043 346, 4 125 557, 5 262 293, 5 306 610, 6 083 000 and 6 083 001.

The diequivalent couplers include those which are colourless and those which have an intense inherent colour which, on colour coupling, disappears or is replaced by the colour of the image dye formed (mask couplers), and white couplers which form essentially colourless products on reaction with colour developer oxidation products. The diequivalent couplers furthermore include couplers which contain, at the coupling point, a leaving group which is liberated on reaction with colour developer oxidation products and exhibits a certain desired photographic activity, for example as a development inhibitor or accelerator, either directly or after one or more further groups have been cleaved off from the radical cleaved off first (for example DE-A-2 703 145, DE-A-2 855 697, DE-A-3 105 026 and DE-A-3 319 428). Examples of such diequivalent couplers are known DIR couplers and DAR and FAR couplers.

Examples of white couplers are:

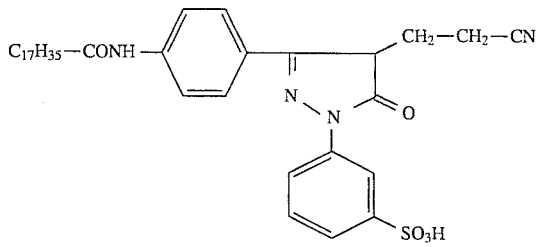
W-1

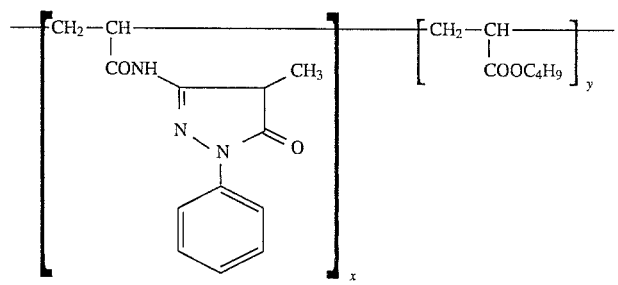
W-2

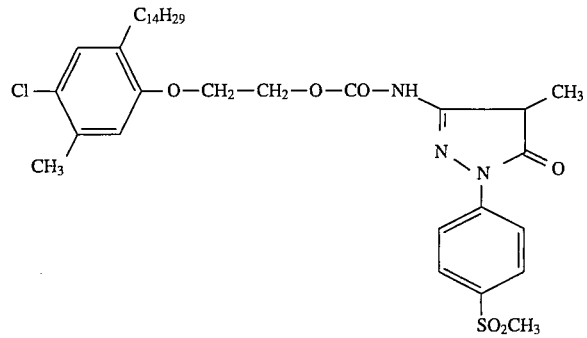
W-3
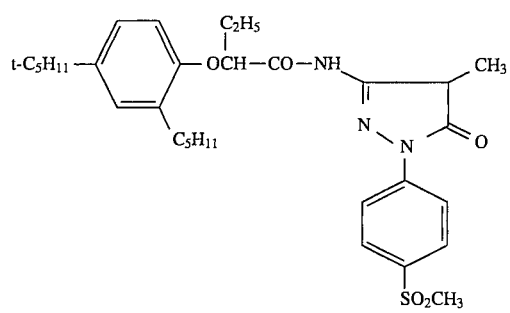
W-4
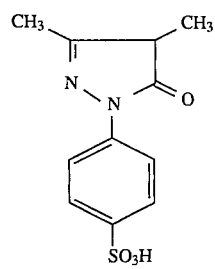
W-5
Examples of mask couplers are:
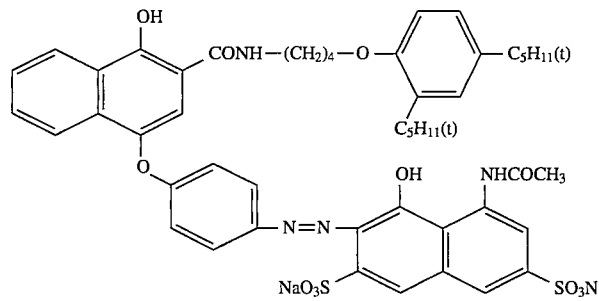
RM-1
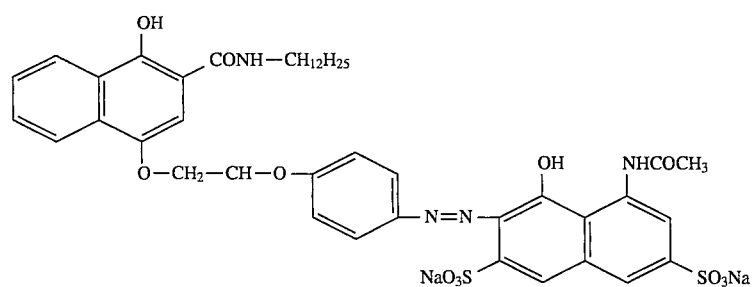
RM-2

-continued
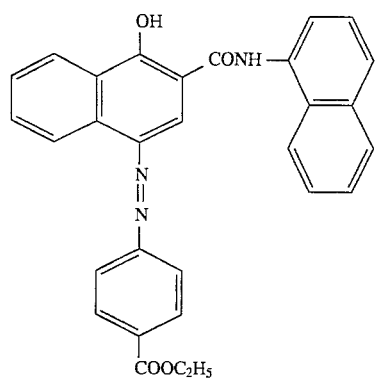
RM-3
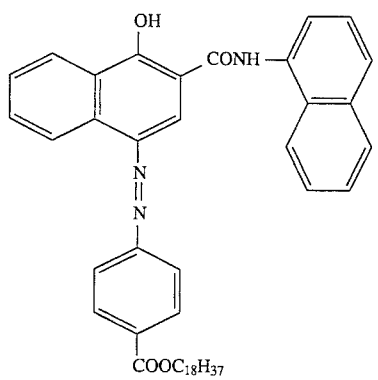
RM-4
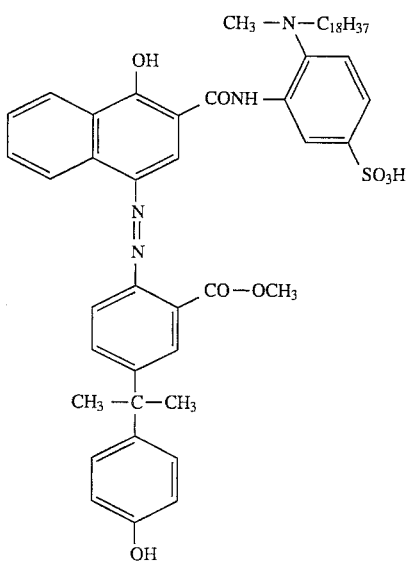
RM-5
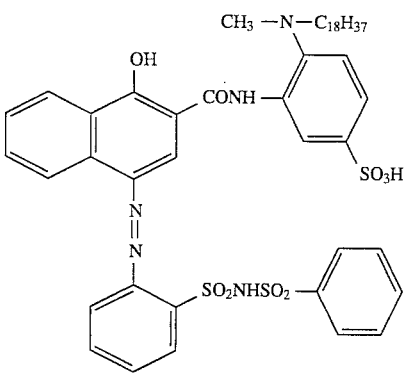
RM-6

-continued
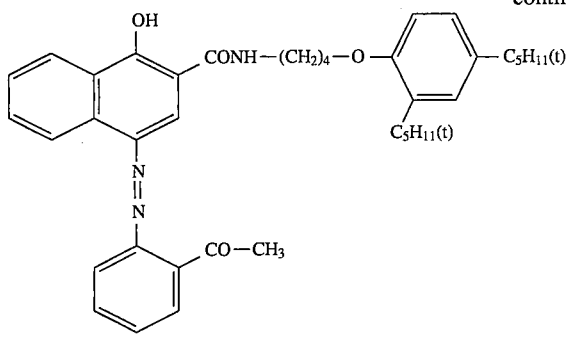
RM-7
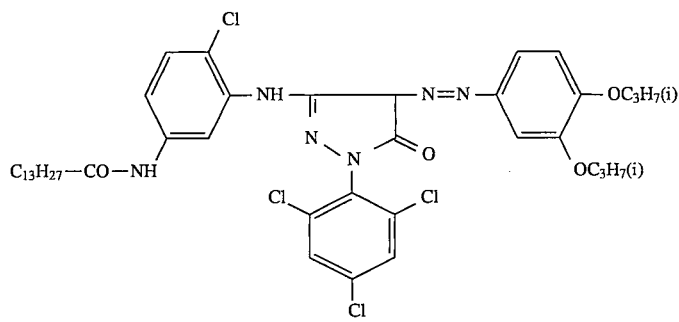
YM-1
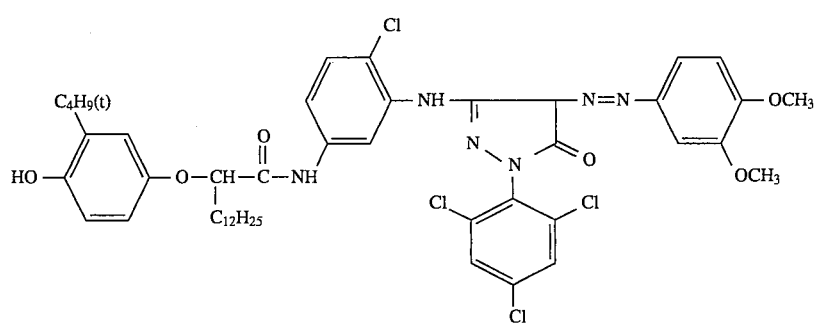
YM-2
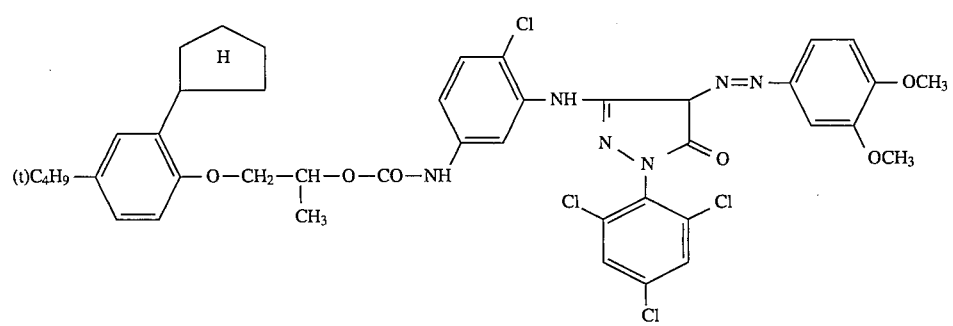
YM-3
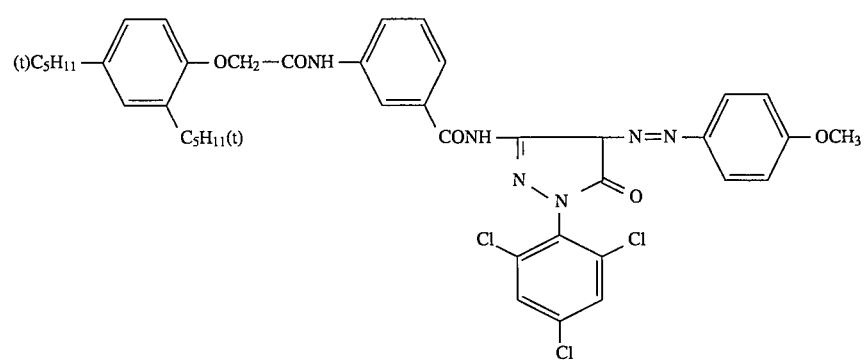
YM-4

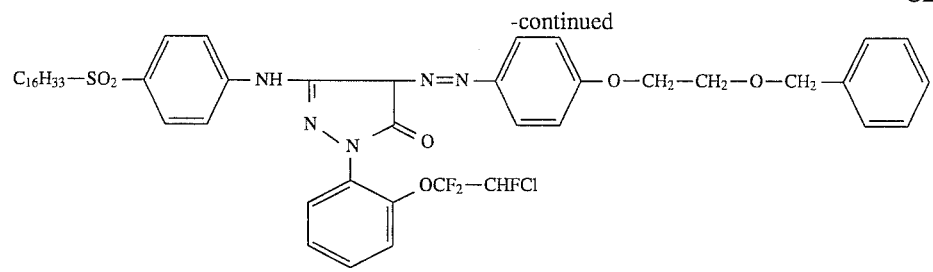 YM-5
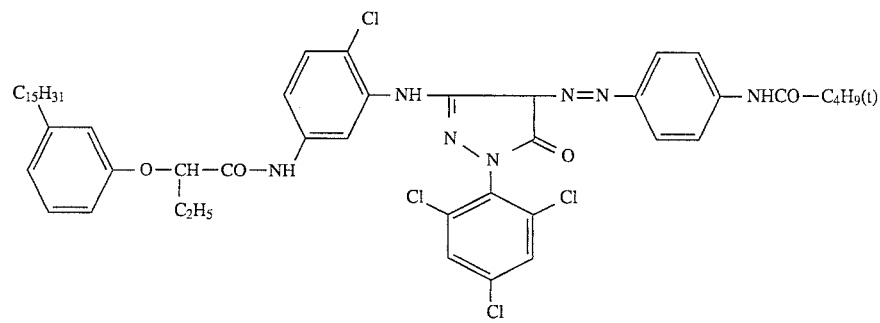 YM-6
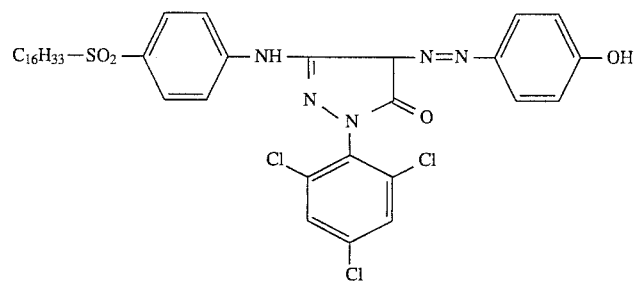 YM-7
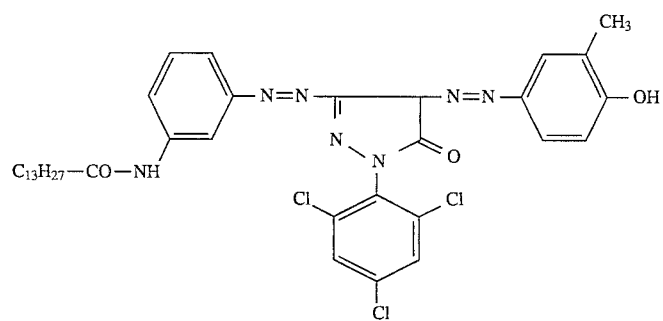 YM-8
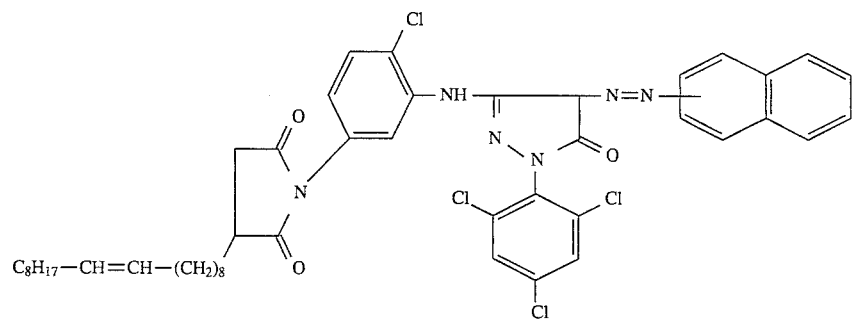 YM-9

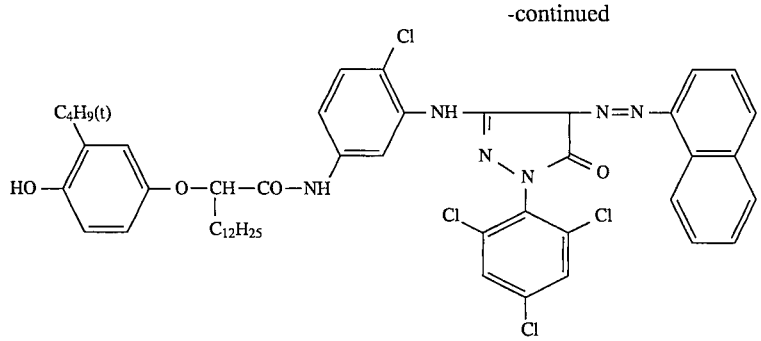

YM-10

DIR couplers, which liberate development inhibitors of the azole type, for example triazoles and benzotriazoles, are described in DE-A-2 414 006, 2 610 546, 2 659 417, 2 754 281, 2 842 063, 3 626 219, 3 630 564, 3 636 824 and 3 644 416. Further advantages for colour reproduction, i.e. colour separation and colour purity, and for detail reproduction, i.e. sharpness and granularity, can be achieved using DIR couplers which, for example, do not liberate the development inhibitor directly as a consequence of coupling with the oxidized colour developer, but instead only do so after a further reaction, which is achieved, for example, with a time-control group. Examples thereof are described in DE-A-2 855 697, 3 299 671, 3 818 231 and 3 518 797, in EP-A-0 157 146 and 0 204 175, in U.S. Pat. Nos. 4,146,396 and 4,438,393, and in GB-A-2 072 363.

DIR couplers which release a development inhibitor which is decomposed in the developer bath to give products which are essentially inactive in photographic terms are described, for example, in DE-A-3 209 486 and EP-A-0 167 168 and 0 219 713. This measure achieves flawless development and processing constancy.

On the use of DIR couplers, in particular those which eliminate a readily diffusable development inhibitor, suitable measures during optical sensitization allow improvements to be achieved in colour reproduction, for example differentiated colour reproduction, as described, for example, in EP-A-0 115 304, and 0 167 173, GB-A-2 165 058, DE-A-3 700 419 and U.S. Pat. No. 4,707,436.

In a multilayer photographic material, the DIR couplers can be added to a wide variety of layers, including, for example, light-insensitive layers or interlayers. However, they are preferably added to the photosensitive silver-halide emulsion layers, the characteristic properties of the silver-halide emulsions, for example their iodide content, the structure of the silver-halide grains or their grain-size distribution, affecting the photographic properties achieved. The effect of the inhibitors liberated can be limited, for example, by incorporating an inhibitor scavenger layer as described in DE-A-2 431 223. For reactivity or stability reasons, it may be advantageous to employ a DIR coupler which, in the particular layer containing it, forms, on coupling, a colour different from the colour to be generated in this layer.

In order to increase the sensitivity, the contrast and the maximum density, use can be made, in particular, of DAR or FAR couplers which release a development accelerator or a fogging agent. Compounds of this type are described, for example, in DE-A-2 534 466, 3 209 110, 3 333 355, 3 410 616, 3 429 545, 3 441 823, in EP-A-0 089 834, 0 110 511, 0 118 087 and 0 147 765, and in U.S. Pat. Nos. 4,618,572 and 4,656,123.

For an example of use in BAR (bleach accelerator releasing) couplers, reference is made to EP-A-193 389.

It may be advantageous to modify the effect of a photographically active group released from a coupler so that an intermolecular reaction of this group with another group occurs after its release, as described in DE-A-3 506 805.

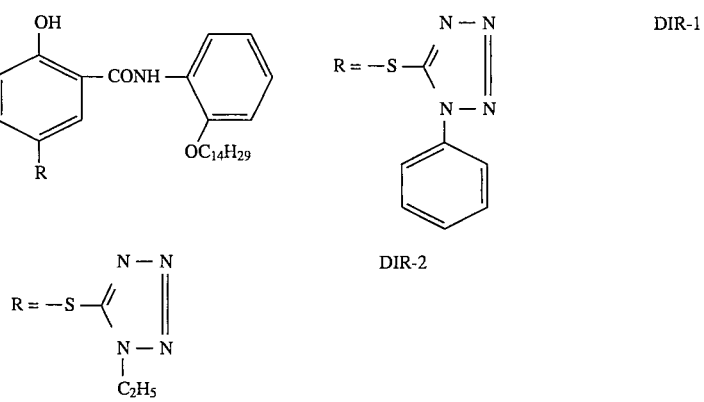

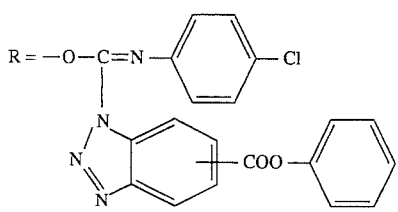
DIR-3
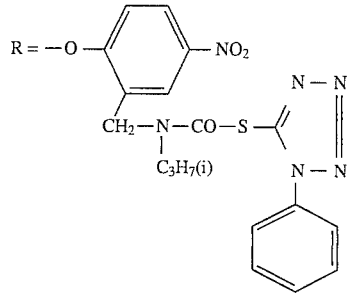
DIR-4
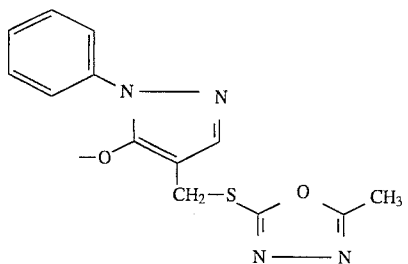
DIR-5
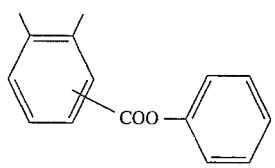
DIR-6
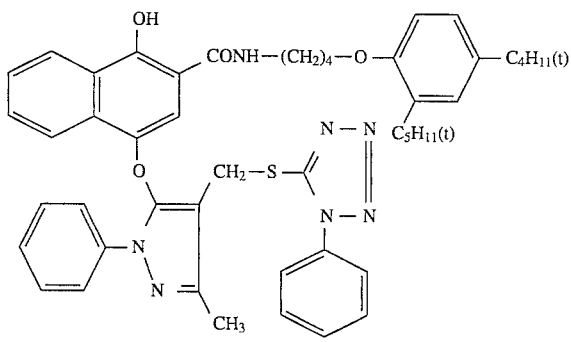
DIR-7
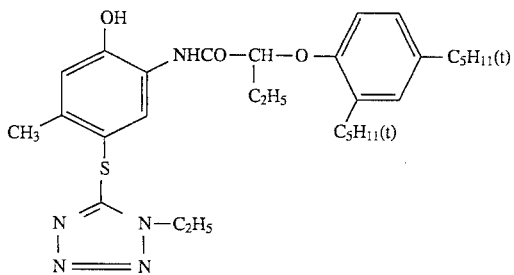
DIR-8
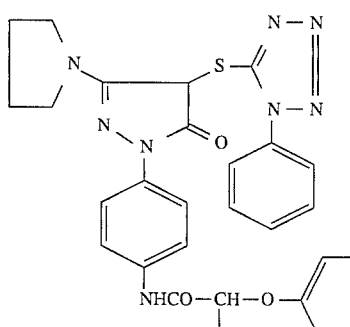
DIR-9
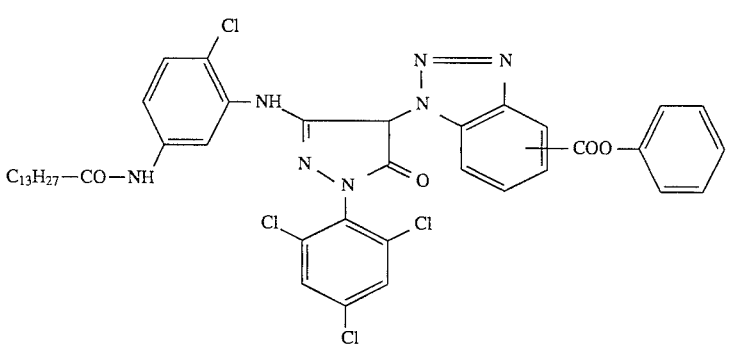
DIR-10

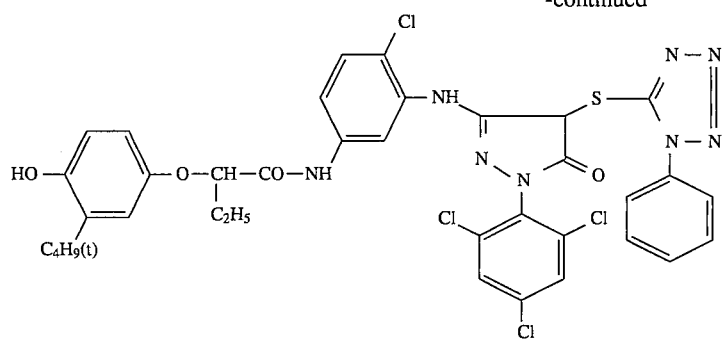
DIR-11
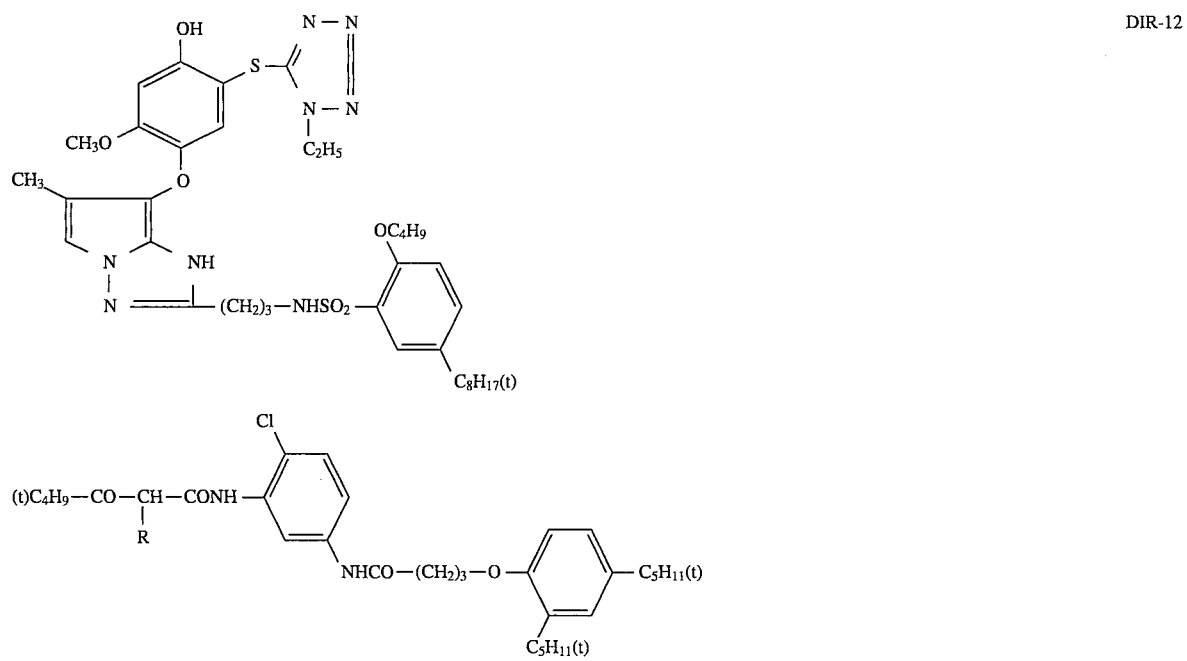
DIR-12
DIR-13
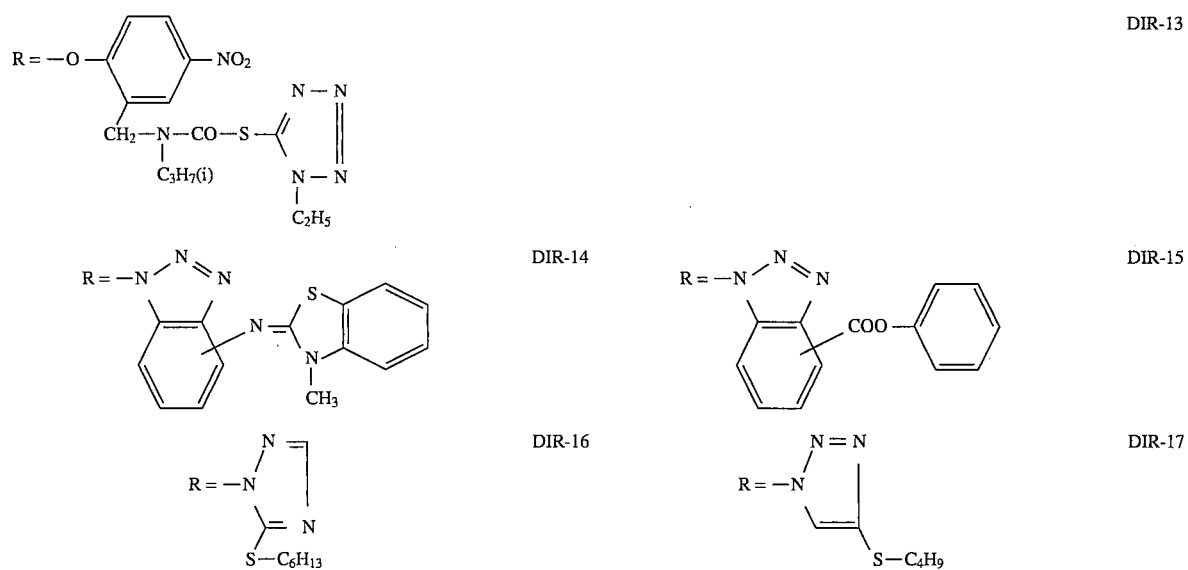
DIR-14
DIR-15
DIR-16
DIR-17

-continued
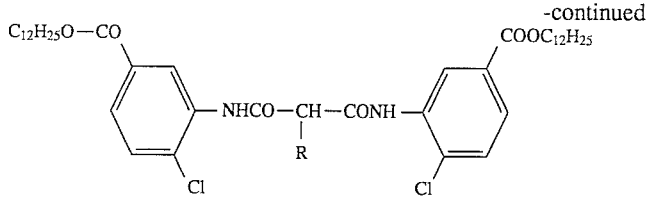
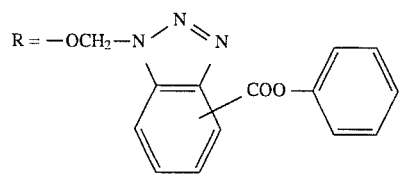 DIR-18
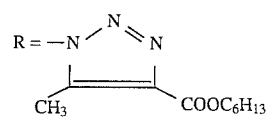 DIR-19
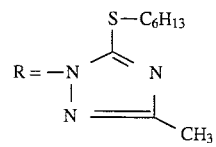 DIR-20
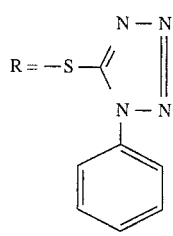 DIR-21
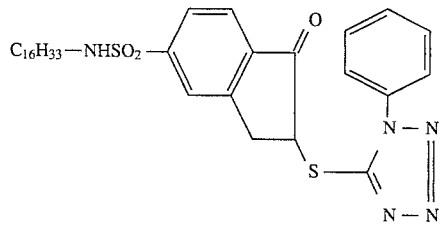 DIR-22
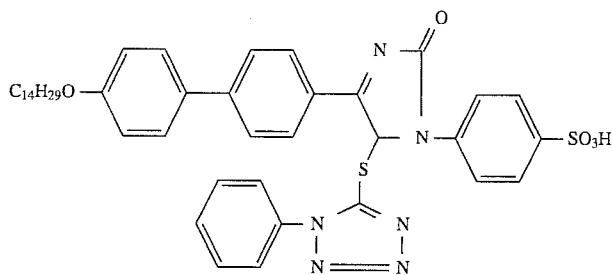 DIR-23
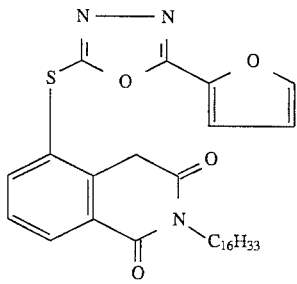 DIR-24
Examples of DAR couplers are the following:

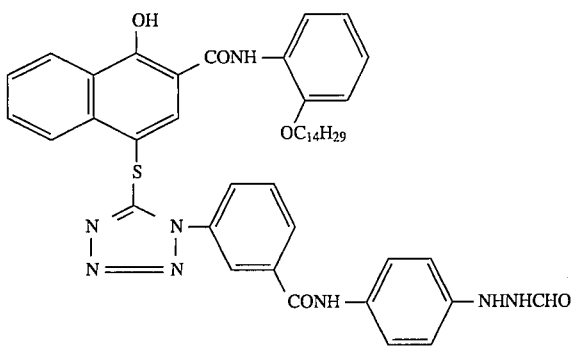

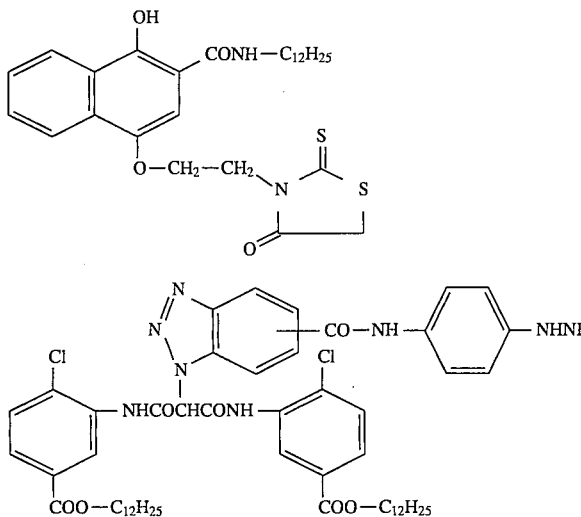

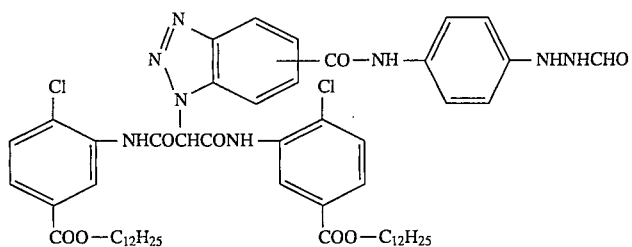

DAR-1

DAR-2

DAR-3

Since, in DIR, DAR and FAR couplers, it is principally the activity of the radical released on coupling that is desired and the colour-forming properties of these couplers are less important, suitable DIR, DAR and FAR couplers include those which give essentially colourless products on coupling (DE-A-1 547 640).

The radical which can be released may also be a balanced radical, so that reaction with colour developer oxidation products gives coupling products which are diffusable or at least have low or restricted mobility (U.S. Pat. No. 4,420,556).

The material may furthermore contain compounds other than couplers, which can release, for example, a development inhibitor, a development accelerator, a bleach accelerator, a developer, a silver-halide solvent, a fogging agent or an antifogging agent, for example DIR hydroquinones or other compounds, as described, for example, in U.S. Pat. Nos. 4,636,546, 4,345,024 and 4,684,604, and in DE-A-3 145 640, 2 515 213, 2 447 079 and in EP-A-198 438. These compounds fulfill the same function as the DIR, DAR or FAR couplers, but do not form coupling products.

High-molecular-weight colour couplers are described, for example in DE-A-1 297 417, DE-A-2 407 569, DE-A-3 148 125, DE-A-3 2 17 200, DE-A-3 320 079, DE-A-3 324 932, DE-A-3 331 743, DE-A-3 340 376, EP-A-27 284 and U.S. Pat. No. 4,080,211. The high-molecular-weight colour couplers are generally prepared by polymerization of ethylenically unsaturated, monomeric colour couplers. However, they can also be obtained by polyaddition or polycondensation. The couplers or other compounds can be incorporated into silver-halide emulsion layers by first preparing a solution, dispersion or emulsion of the compound in question and then adding this to the casting solution for the layer in question. The choice of suitable solvent or dispersion medium depends on the particular solubility of the compound.

Methods for incorporating compounds which are essentially insoluble in water by grinding processes are described, for example, in DE-A-2 609 741 and DE-A-2 609 742.

Hydrophobic compounds can also be introduced into the casting solution using high-boiling solvents, known as oil formers. Corresponding methods are described, for example, in U.S. Pat. Nos. 2,322,027, 2,801,170, 2,801,171 and EP-A-0 043 037.

The high-boiling solvents can also be replaced by oligomers or polymers, known as polymeric oil formers.

The compounds can also be introduced into casting solution in the form of loaded lattices. Reference is made, for example, to DE-A-2 541 230, DE-A-2 541 274, DE-A-2 835 856, EP-A-0 014 921, EP-A-0 069 671, EP-A-0 130 115 and U.S. Pat. No 4,291,113.

The diffusion-resistant incorporation of anionic, water-soluble compounds (for example dyes) can also be effected with the aid of cationic polymers, known as mordant polymers.

The UV absorbers of the formula I according to the invention or corresponding homopolymers or copolymers can be incorporated into the colour-photographic material alone or together with the colour coupler and any further additives by pre-dissolving them in high-boiling organic solvents.

Examples of suitable high-boiling solvents are alkyl phthalate, phosphonates, phosphates, citrates, benzoates, amides, fatty acid esters, trimesates, alcohols, phenols, anilin derivatives and hydrocarbons.

Examples of suitable high-boiling solvents are dibutyl phthalate, dicyclohexyl phthalate, di-2-ethylhexyl phthalate, decyl phthalate, triphenyl phosphate, tricresyl phosphate, 2-ethylhexyl diphenyl phosphate, tridecyl phosphate, tributoxyethyl phosphate, trichloropropyl phosphate, di-2-ethylhexyl phenyl phosphate, 2-ethylhexyl benzoate, dodecyl benzoate, 2-ethylhexyl p-hydroxybenzoate, diethyldodecanamide, N-tetradecylpyrrolidone, isostearyl alcohol, 2,4-di-t-amylphenol, dioctyl acetate, glycerol tributyrate, isostearyl lactate, trioctyl citrate, N,N-dibutyl-2-butoxy-5-t-octylanilin, paraffin, didecylbenzene and diisopropylnaphthalene.

Further details on high-boiling solvents which can be used are given in the publications below:

Phosphates: GB-A-791 219, BE-A-755 248, JP-A-76/76 739, 78/27 449, 78/218 252, 78/97 573, 79/148 133, 82/216 177, 82/93 323 and 83/216 177 and EP-A-265 296. Phthalates: GB-A-791 219, JP-A-77/98 050, 82/93 322, 82/216 176, 82/218 251, 83/24 321, 83/45 699 and 84/79 888. Amides: GB-A-791 129, JP-A-76/105 043, 77/13 600, 77/61 089, 84/189 556, 87/239 149, U.S. Pat. No. 928,741, EP-A-270 341 and WO 88/00 723. Phenols: GB-A-820 329, FR-A-1 220 657, JP-A-69/69 946, 70/3 818, 75/123 026, 75/82 078, 78/17 914, 78/21 166, 82/212 114 and 83/45 699.

Other oxygen-containing compounds: U.S. Pat. Nos. 3,748,141, 3,779,765, JP-A-73/75 126, 74/101 114, 74/10 115, 75/101 625, 76/76 740, 77/61 089, EP-A-304 810 and BE-A-826 039.

Other compounds: JP-A-72/115 369, 72/130 258, 73/127 521, 73/76 592, 77/13 193, 77/36 294, 79/95 233, 91/2 748, 83/105 147 and Research Disclosure 82/21 918.

The amount of high-boiling solvent is, for example, in the range from 50 mg to 2 g per m$^2$ of base, preferably from 200 mg to 1 g per m$^2$.

If desired, the UV absorbers can also be dispersed in the gelatin layer without oil; Research Disclosure 88/296 017 and 89/303 070.

Furthermore, the UV absorber or a mixture of UV absorbers can be introduced into at least one of the photographic layers in such a way that a latex containing small lipophilic particles (typical diameter 0.02 to 2 μm) is produced which contains both the UV absorber and a hydrophobic polymer. A corresponding method is described, for example, in column 17 of U.S. Pat. No. 5,200,307 for benzotriazoles. UV absorbers of the formula I or corresponding homopolymers or copolymers can, in accordance with the invention, be dissolved, alone or in combination with another UV absorber of the same or a different class, for example from the class of the 2-hydroxyphenylbenzotriazoles, be dissolved together with a hydrophobic polymer in a suitable organic solvent, for example ethyl acetate; this solution can subsequently be emulsified and dispersed to give a latex in water or aqueous gelatin. After removal of the organic solvent, the latex can be introduced into the photographic system. Examples of suitable hydrophobic polymers are homopolymers or copolymers as can be obtained by polymerization of ethylenically unsaturated monomers of the formulae II to VII described above. In certain cases, the hydrophobic polymer can be a condensation polymer, for example a polyester such as 1,4-butanediol/adipic acid polyester or polycaprolactone. A high-boiling organic solvent can also be used in addition if, for example, the UV absorber employed is not liquid. Mixtures of suitable organic solvents can also expediently be employed.

The invention therefore also relates to a photographic recording material which, in at least one of the layers, contains a hydrophobic polymer in addition to the polymeric UV absorber. This polymer can be, for example, a hydrophobic homopolymer or copolymer of monomers of the formulae II to VII described above. This polymer preferably contains no polyoxyalkylene, no hydroxyl groups and no sulfone groups.

Another method, described analogously, for example, in GB-A-2 016 017 and U.S. Pat. No. 5,372,922, comprises adding the novel UV absorber to a latex prepared by emulsion polymerization as described above and comprising small, water-insoluble, solvent-containing particles; the UV absorber is then taken up by the particles. The loaded latex can subsequently be introduced into the photographic system.

The invention therefore furthermore relates to a photographic recording material comprising the copolymeric UV absorber and the hydrophobic polymer in at least one of the layers, which material is obtainable by dissolving the UV absorber and the hydrophobic polymer in an organic solvent and then emulsifying and dispersing the solution in an aqueous medium and introducing the latex into the photographic system, and to a corresponding process for the production of a photographic recording material.

Each of the photosensitive layers of different sensitization can comprise a single layer or alternatively two or more silver-halide emulsion part-layers (DE-C-1 121 470).

Red-sensitive silver-halide emulsion layers are frequently arranged closer to the layer base than are green-sensitive silver-halide emulsion layers, which are in turn arranged closer to the layer base than are blue-sensitive layers; in general, a non-photosensitive yellow filter layer is positioned between green-sensitive layers and blue-sensitive layers.

If the inherent sensitivity of the green- and red-sensitive layers is suitably low, other layer arrangements omitting the yellow filter layer can be chosen in which, for example, the blue-sensitive, then the red-sensitive and finally the green-sensitive layers are arranged on the base.

The non-photosensitive interlayers generally arranged between layers of different spectral sensitivity can contain agents which prevent undesired fusion of developer oxidation products from a photosensitive layer into another photosensitive layer of different spectral sensitization.

Suitable agents, also known as EOP scavengers, are described in Research Disclosure 17 643 (December 1978), Chapter VII, 17 842 (February 1979) and 18 716 (November 2979), page 650, and in EP-A-0 069 070, 0 098 072, 0 124 877 and 0 125 522.

Examples of particularly suitable compounds are:

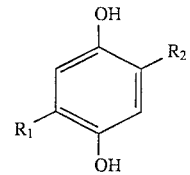

$R_1$ and $R_2$=$C_8H_{17}(t)$ $C_{12}H_{25}(s)$ $C_6H_{13}(t)$

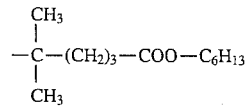

$C_8H_{17}(s)$  $C_{15}H_{31}(t)$

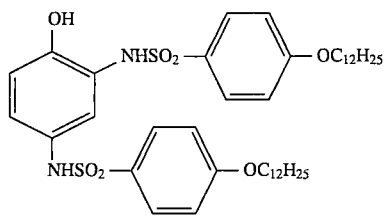

If the material contains a plurality of sub-layers of identical spectral sensitization, these can differ in composition, in particular regarding the type and amount of silver-halide grains. In general, the sub-layer of higher sensitivity will be arranged further from the base than will the sub-layer of lower sensitivity. Sub-layers of identical spectral sensitization can be adjacent to one another or separated by other layers, for example by layers of different spectral sensitization. For example, all high-sensitivity layers and all low-sensitivity layers can in each case be combined to form a layer packet (DE-A-1 958 709, DE-A-2 530 645 and DE-A-2 622 922).

The photographic material may furthermore contain UV absorbing compounds, white toners, spacers, filter dyes, formalin scavengers, light stabilizers, antioxidants, $D_{min}$ dyes, additives for improving the dye, coupler and white destabilization and for reducing colour casts, plasticizers (lattices), biocides, inter alia.

The photographic layers in the novel material, in particular layers b, c and/or d in the colour-photographic material described above by way of example, may also contain other UV absorbers. Examples of such UV absorbers are benzotriazoles, 2-hydroxybenzophenones, oxanilides, cyanoacrylates, salicylates, acrylonitrile derivatives and thiazolines.

Such UV absorbers are described in greater detail, for example, in the following publications: U.S. Pat. Nos. 3,314,794, 3,352,681, 3,705,805, 3,707,375, 4,045,229, 3,700,455, 3,700,458, 3,533,794, 3,698,907, 3,705,805, 3,738,837, 3,762,272, 4,163,671, 4,195,999, 4,309,500, 4,431,726, 4,443,543, 4,576,908 and 4,749,643, GB-A-1 564 089, EP-A-190 003 and JP-A-71/2784, 81/111 826, 81/27 146, 88/53 543 and 88/55 542. Preferred UV absorbers are benzotriazoles, in particular 2-(2-hydroxyphenyl) benzotriazoles.

Preference is also given to a photographic recording material additionally comprising a UV absorber from the hydroxyphenyltriazine series which does not conform to the formula (I), as described, for example, in U.S. Pat. Nos. 5,300,414 and 5,364,749.

Examples of particularly suitable compounds are: Benzotriazole compounds of the formula AII

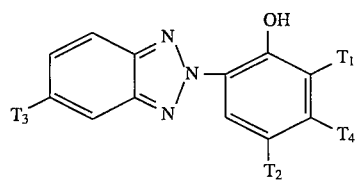

in which $T_1$, $T_2$ and $T_3$, independently of one another, are hydrogen, halogen, alkyl, carboxylate-substituted alkyl, alkoxy, aryloxy, hydroxyl or acyloxy, and $T_4$ is hydrogen, alkoxy, aryloxy or acyloxy.

Examples of HBT compounds of the formula AII are:

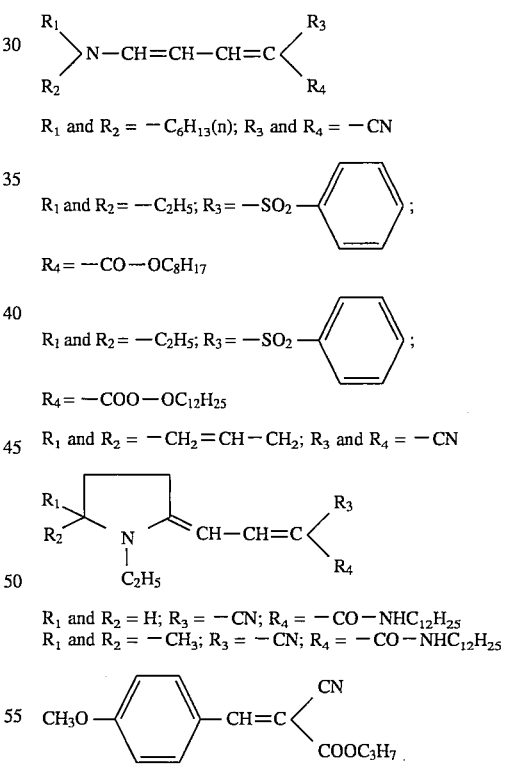

| HBT No. | $T_1$ | $T_2$ | $T_3$ |
|---|---|---|---|
| HBT-1 | H | $CH_3$ | H |
| HBT-2 | H | $C(CH_3)_3$ | H |
| HBT-3 | $C(CH_3)_3$ | $CH_3$ | Cl |
| HBT-4 | $C(CH_3)_3$ | $C(CH_3)_3$ | Cl |
| HBT-5 | $C(CH_3)_2C_2H_5$ | $C(CH_3)_2C_2H_5$ | H |
| HBT-6 | $CH(CH_3)C_2H_5$ | $C(CH_3)_3$ | H |
| HBT-7 | $C(CH_3)_2$—Ph | $C(CH_3)_2$—Ph | H |
| HBT-8 | $C(CH_3)_3$ | $CH_2CH_2COOC_8H_{17}$ (Isomers)* | Cl |
| HBT-9 | $C(CH_3)_3$ | $CH_2CH_2COOC_8H_{17}$ (Isomers)* | H |
| HBT-10 | $C_{12}H_{25}$ (Isomers)* | $CH_3$ | H |

*Principal product $$\begin{matrix} R_1 \\ R_2 \end{matrix} \!\!\!> N\!-\!CH\!=\!CH\!-\!CH\!=\!C\!<\!\!\! \begin{matrix} R_3 \\ R_4 \end{matrix}$$

$R_1$ and $R_2 = -C_6H_{13}(n)$; $R_3$ and $R_4 = -CN$ $R_1$ and $R_2 = -C_2H_5$; $R_3 = -SO_2$—Ph;

$R_4 = -CO-OC_8H_{17}$ $R_1$ and $R_2 = -C_2H_5$; $R_3 = -SO_2$—Ph;

$R_4 = -COO-OC_{12}H_{25}$ $R_1$ and $R_2 = -CH_2=CH-CH_2$; $R_3$ and $R_4 = -CN$ $$\begin{matrix} R_1 \\ R_2 \end{matrix}\!\!\!>\!\!\!\overset{\displaystyle\frown}{\underset{\underset{C_2H_5}{|}}{N}}\!\!\!\!=\!CH\!-\!CH\!=\!C\!<\!\!\!\begin{matrix} R_3 \\ R_4 \end{matrix}$$

$R_1$ and $R_2 = H$; $R_3 = -CN$; $R_4 = -CO-NHC_{12}H_{25}$
$R_1$ and $R_2 = -CH_3$; $R_3 = -CN$; $R_4 = -CO-NHC_{12}H_{25}$ $CH_3O$—Ph—$CH=C<\begin{matrix}CN\\COOC_3H_7\end{matrix}$ It is also possible to use UV-absorbing couplers (such as cyan couplers of the α-naphthol type) and UV-absorbing polymers. These UV absorbers can be fixed in a specific layer by mordants.

Filter dyes which are suitable for visible light include oxonol dyes, hemioxonol dyes, styryl dyes, merocyanine dyes, cyanine dyes and azo dyes. Of these dyes, oxonol dyes, hemioxonol dyes and merocyanine dyes are particularly advantageous.

Examples of suitable white toners are described in Research Disclosure 17 643 (December 1978), Chapter V, in U.S. Pat. Nos. 2,632,701 and 3,269,840, and in GB-A-852 075 and 1 319 763.

Certain binder layers, in particular the layer furthest removed from the base, but also occasionally interlayers, in particular if they form the layer furthest removed from the base during production, may contain photographically inert particles of an inorganic or organic nature, for example as matting agents or as spacers (DE-A-3 331 542; DE-A-3 424 893 and Research Disclosure 17 643 (December 1978), Chapter XVI).

The mean particle diameter of the spacers is, in particular, in the range from 0.2 to 2 μm. The spacers are water-insoluble and can be alkali-insoluble or alkali-soluble, the alkali-soluble spacers generally being removed from the photographic material in the alkaline development bath. Examples of suitable polymers are polymethyl acrylate, copolymers of acrylic acid and methyl methacrylate, and hydroxypropylmethylcellulose hexahydrophthalate.

Suitable formalin scavengers are, for example:

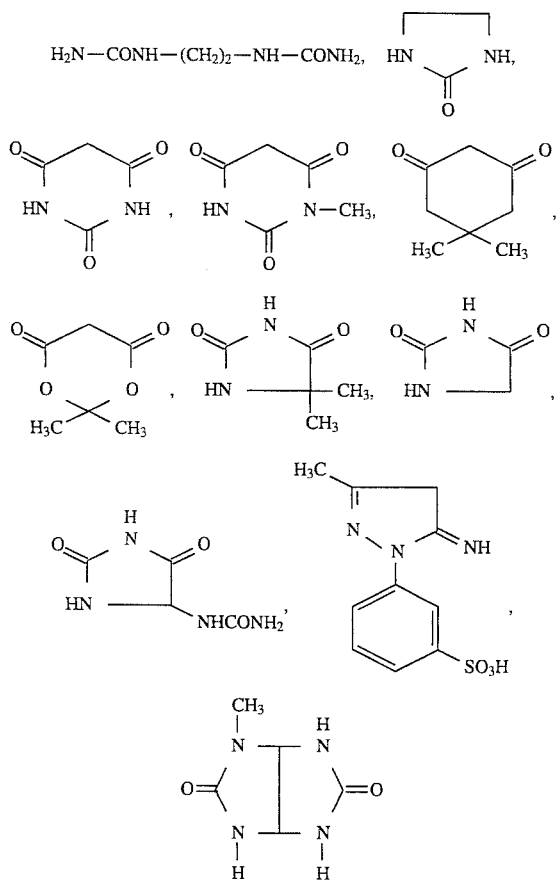

The photographic layers may also contain phenolic compounds which act as light stabilisers for the colour image and as colour cast inhibitors. They may be present in a photosensitive layer (colour layer) or in an interlayer, alone or together with other additives. Such compounds are described in greater detail, for example, in the publications below: U.S. Pat. Nos. 3,700,455, 3,591,381, 3,573,052, 4,030,931, 4,174,220, 4,178,184, 4,228,235, 4,268,593, 4,279,990, 4,346,165, 4,366,226, 4,447,523, 4,528,264, 4,581,326, 4,562,146 and 4,559,297, GB-A-1 309 277, 1 547 302, 2 023 862, 2 135 788, 2 139 370 and 2 156 091; DE-A-2 301 060, 2 347 708, 2 526 468, 2 621 203 and 3 323 448; DD-A-200 691 and 214 468; EP-A-106 799, 113 124, 125 522, 159 912, 161 577, 164 030, 167 762, 176 845, 246 766, and 320 776; JP-A-74/134 326, 76/127 730, 76/30 462, 77/3 822, 77/154 632, 78/10 842, 79/48 535, 79/70 830, 79/73 032, 79/147 038, 79/154 325, 79/155 836, 82/142 638, 83/224 353, 84/5 246, 84/72 443, 84/87 456, 84/192 246, 84/192 247, 84/204 039, 84/204 040, 84/212 837, 84/220 733, 84/222 836, 84/228 249, 86/2 540, 86/8 843, 86/18 835, 86/18 836, 87/11 456, 87/42 245, 87/62 157, 86/6 652 and 89/137 258 and in Research Disclosure 79/17 804.

The photographic layers may also contain certain phosphorus(III) compounds, in particular phosphites and phosphonites. These act as light stabilisers for the colour images and as dark-storage stabilisers for magenta couplers. They are preferably added to the high-boiling solvents together with the coupler. Phosphorus(III) compounds of this type are described in greater detail, for example, in the publications below: U.S. Pat. Nos. 4,407,935, 4,436,811, 4,956,406, EP-A-181 289, JP-A-73/32 728, JP-A-76/1 420 and JP-A-55/66 741.

The photographic layers may also contain organometallic complexes which are light stabilisers for the colour images, in particular for the magenta dyes. Such compounds and combinations thereof with other additives are described in greater detail, for example, in the publications below: U.S. Pat. Nos. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165 and 4,590,153; JP-A-81/167 138, 81/168 652, 82/30 834 and 82/161 744; EP-A-137 271, 161 577 and 185 506; DE-A-2 853 865.

The photographic layers may also contain hydroquinone compounds. These act as light stabilisers for the colour couplers and for the colour images and as scavengers of oxidized developer in interlayers. They are used in particular in the magenta layer. Hydroquinone compounds of this type and combinations thereof with other additives are described in greater detail, for example, in the publications below: U.S. Pat. Nos. 2,360,290, 2,336,327, 2,403,721, 2,418,613, 2,675,314, 2,701,197, 2,710,801, 2,732,300, 2,728,659, 2,735,765, 2,704,713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 4,416,978, 4,430,425, 4,277,558, 4,489,155, 4,504,572 and 4,559,297, FR-A-885 982; GB-A-891 158, 1 156 167, 1 363 921, 2 022 274, 2 066 975, 2 071 348, 2 081 463, 2 117 526 and 2 156 091; DE-A-2 408 168, 2 726 283, 2 639 930, 2 901 520, 3 308 766, 3 320 483 and 3 323 699; DD-A-216 476, 214 468,214 469, EP-A-84 290, 110 214, 115 305, 124 915, 124 877, 144 288, 147 747, 178 165 and 161 577; JP-A-75/33 733, 75/21 249, 77/128 130, 77/146 234, 79/70 036, 79/133 131, 81/83 742, 81/87 040, 81/109 345, 83/134 628, 82/22 237, 82/112 749, 83/17 431, 83/21 249, 84/75 249, 84/149 348, 84/182 785, 84/180 557, 84/189 342, 84/228 249, 84/101 650, 79/24 019, 79/25 823, 86/48 856, 86/48 857, 86/27 539, 86/6 652, 86/72 040, 87/11 455 and 87/62 157, and in Research Disclosure 79/17 901, 79/17 905, 79/18 813, 83/22 827 and 84/24 014.

The photographic layers may also contain derivatives of hydroquinone ethers. These compounds act as light stabilisers and are particularly suitable for stabilising magenta dyes. Such compounds and combinations thereof with other additives are described in greater detail, for example, in the publications below: U.S. Pat. Nos. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990,. 4,113,495, 4,120,723, 4,155,765, 4,159,910, 4,178,184, 4,138,259, 4,174,220, 4,148,656, 4,207,111, 4,254,216, 4,134,011, 4,273,864, 4,264,720, 4,279,990, 4,332,886, 4,436,165, 4,360,589, 4,416,978, 4,385,111, 4,459,015 and 4,559,297; GB-A 1 347 556, 1 366 441, 1 547 392, 1 557 237 and 2 135 788; DE-A 3 214 567; DD-214 469, EP-A 161 577, 167 762, 164 130 and 176 845; JP-A 76/123 642, 77/35 633, 77/147 433, 78/126, 78/10 430, 78/53 321, 79/24 019, 79/25 823, 79/48 537, 79/44 521, 79/56 833, 79/70 036, 79/70 830, 79/73 032, 79/95 233, 79/145 530, 80/21 004, 80/50 244, 80/52 057, 80/70 840, 80/139 383, 81/30 125, 81/151 936, 82/34 552, 82/68 833, 82/204 306, 82/204 037, 83/134 634, 83/207 039, 84/60 434, 84/101 650, 84/87 450, 84/149 348, 84/182 785, 86/72 040, 87/11 455, 87/62 157, 87/63 149, 86/2 151, 86/6 652, 86/48 855 and 89/309 058 and in Research Disclosure 78/17 051.

The photographic layers, and especially the layers containing the UV absorber of the invention, may also contain sterically hindered amine light stabilizers (HALS). Preferably, these stabilizers are derivatives of 2,2,6,6-tetraalkylpiperidine, which compounds are characterized in that they carry at least one group having the formula

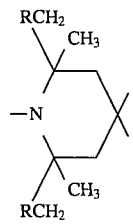

wherein R is hydrogen or methyl, especially hydrogen. Examples are inter alia the following compounds: bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy and 4-stearyloxy-2,2,6,6-tetramethylpiperidine, a condensation product of N,N'-bis(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin.

Examples of particularly suitable compounds are:

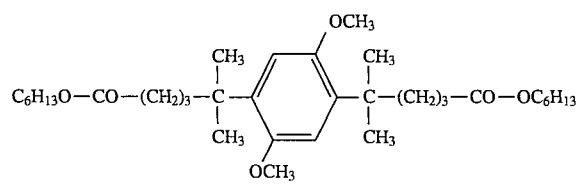

(ST-1)

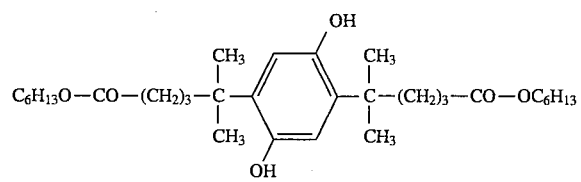

(ST-2)

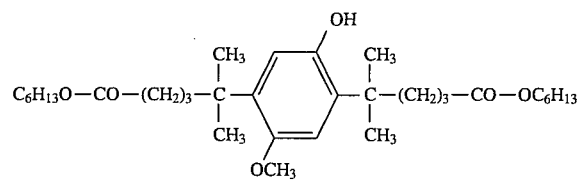

(ST-3)

-continued
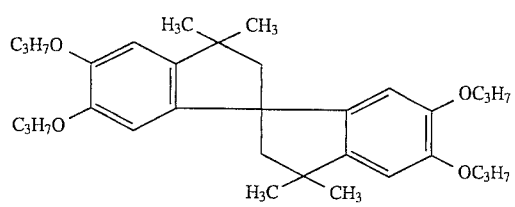 (ST-4)
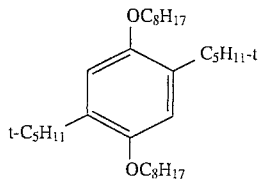 (ST-5)
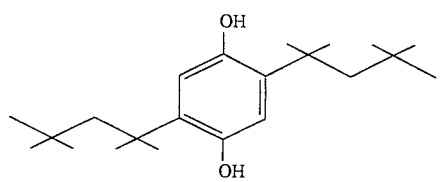 (ST-6)
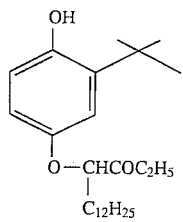 (ST-7)
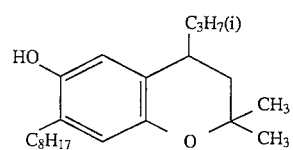 (ST-8)
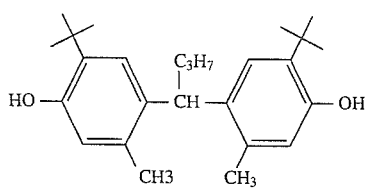 (ST-9)
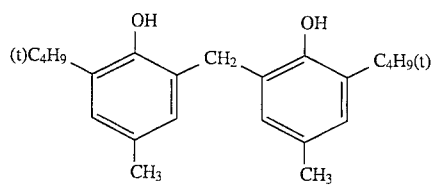 (ST-10)
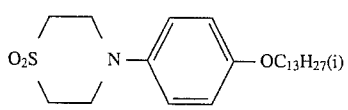 (ST-11)
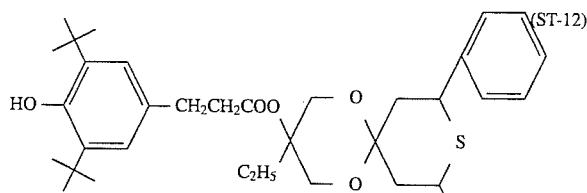 (ST-12)
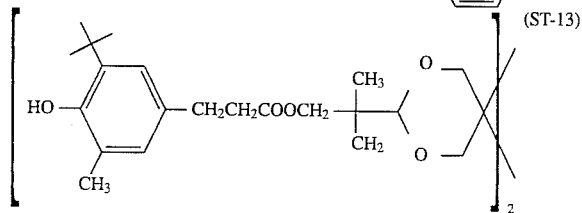 (ST-13)
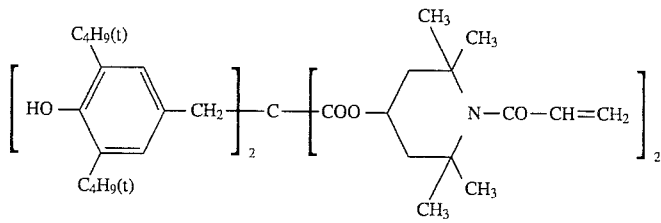 (ST-14)
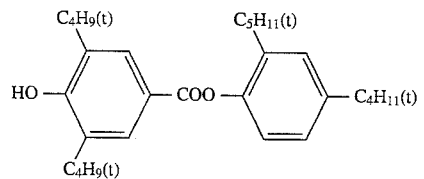 (ST-15)

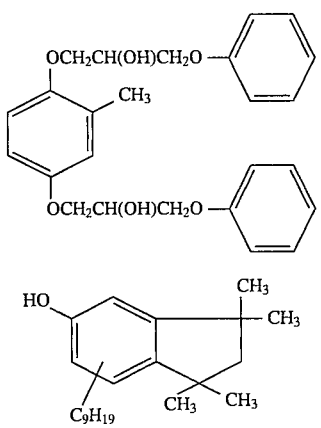 (ST-16)

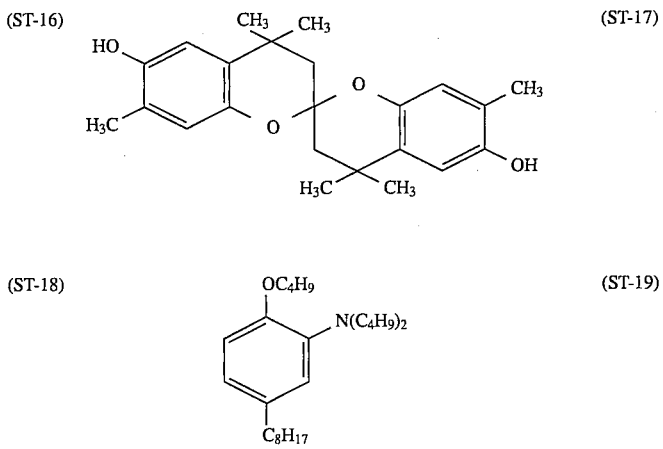 (ST-17)

(ST-18)

(ST-19)

and the compounds mentioned as EOP scavengers.

The layers of the photographic material can be cured using conventional curing agents. Examples of suitable curing agents are formaldehyde, glutaraldehyde and similar aldehyde compounds, diacetyl, cyclopentadione and similar ketone compounds, bis(2-chloroethylurea), 2-hydroxy-4,6-dichloro-1,3,5-triazine and similar compounds containing reactive halogen (U.S. Pat. Nos. 3,288,775, 2,732,303, GB-A-974 723 and GB-A-1167 207), divinyl sulfone compounds, 5-acetyl-1,3-diacryloylhexahydro-1,3,5-triazine and other compounds containing a reactive olefin bond (U.S. Pat. Nos. 3,635,718, 3,232,763 and GB-A-994 869); N-hydroxymethylphthalimide and other N-methylol compounds (U.S. Pat. Nos. 2,732,316 and 2,586,168); isocyanates (U.S. Pat. Nos. 3,103,437); aziridine compounds (U.S. Pat. Nos. 3,017,280 and 2,983,611); acid derivatives (U.S. Pat. Nos. 2,725,294 and 2,725,295); compounds of the carbodiimide type (U.S. Pat. No. 3,100,704); carbamoylpyridinium salts (DE-A-2 225 230 and U.S. Pat. No. 2,439,511); carbamoylpyridinium compounds (DE-A-2 408 814); compounds containing a phosphorus-halogen bond (JP-A-113 929/83); N-carbonyloximide compounds (JP-A-43 353/81); N-sulfonyloximido compound (U.S. Pat. No. 4,111,926), dihydroquinoline compounds (U.S. Pat. No. 4,013,468), 2-sulfonyloxypyridinium salts (JP-A-110 762/81), formamidinium salts (EP-A-0 162 308), compounds containing two or more N-acyloximino groups (U.S. Pat. No. 4,052,373), epoxy compounds (U.S. Pat. No. 3,091,537), compounds of the isoxazole type (U.S. Pat. No. 3,321,313 and 3,543,292); halocarboxaldehydes, such as mucochloric acid; dioxane derivatives, such as dihydroxydioxane and dichlorodioxane; and inorganic curing agents, such as chromiumalum and zirconium sulfate.

The curing can be accomplished in a known manner by adding the curing agent to the casting solution for the layer to be cured or by coating the layer to be cured with a layer comprising a diffusable curing agent.

The classes mentioned include slow-acting and fast-acting curing agents and so-called instant curing agents, which are particularly advantageous. The term "instant curing agents" is taken to mean compounds which crosslink suitable binders in such a way that, immediately after casting, at the latest after 24 hours, preferably at the latest after 8 hours, the curing is complete to such an extent that no further change in sensitometry caused by the crosslinking reaction or swelling of the layer system occurs. The term "swelling" is taken to mean the difference between the wet-layer thickness and the dry-layer thickness in the case of aqueous processing of the film (Photogr. Sci., Eng. 8 (1964), 275; Photogr. Sci., Eng. (1972), 449).

These curing agents which react very quickly with gelatin are, for example, carbamoylpyridinium salts which are capable of reacting with free carboxyl groups of the gelatin so that the latter react with free amino groups of the gelatin to form peptide bonds and crosslinking of the gelatin.

Suitable examples of instant curing agents are compounds of the formula

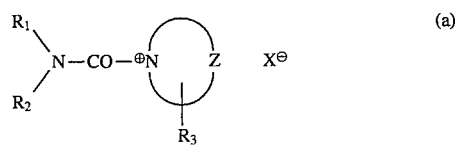 (a)

in which $R_1$ is alkyl, aryl or aralkyl, $R_2$ is as defined for $R_1$ or is alkylene, arylene, aralkylene or alkarylene, where the second bond is linked to a group of the formula,

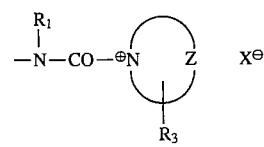

or $R_1$ and $R_2$ together are the atoms necessary to complete a substituted or unsubstituted heterocyclic ring, for example a piperidine, piperazine or morpholine ring, where the ring may be substituted, for example, by example, by $C_1$–$C_3$ alkyl or halogen, $R_3$ is hydrogen, alkyl, aryl, alkoxy, —$NR_4$—$COR_5$, —$(CH_2)_m$—$NR_8R_9$, —$(CH_2)_n$—$CONR_{13}R_{14}$ or

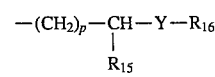

or a bridge or a direct bond to a polymer chain, where $R_4$, $R_6$, $R_7$, $R_9$, $R_{14}$, $R_{15}$, $R_{17}$, $R_{18}$, and $R_{19}$ are hydrogen or $C_1$–$C_4$alkyl, $R_5$ is hydrogen, $C_1$–$C_4$alkyl or $NR_6R_7$, $R_8$ is —$COR_{10}$ $R_{10}$ is $NR_{11}R_{12}$ $R_{11}$ is $C_1$–$C_4$alkyl or aryl, in particular phenyl, $R_{12}$ is hydrogen, $C_1$–$C_4$alkyl or aryl, in particular phenyl, $R_{13}$ is hydrogen, $C_1$–$C_4$alkyl or aryl, in particular phenyl, $R_{16}$ is hydrogen, $C_1$–$C_4$alkyl, —$COR_{18}$ or $CONHR_{19}$, m is a number from 1 to 3 n is a number from 0 to 3 p is a number from 2 to 3,

Y is O or $NR_{17}$, or $R_{13}$ and $R_{14}$ together are the atoms necessary to complete a substituted or unsubstituted heterocyclic ring, for example a piperidine, piperazine or morpholine ring, where the ring may be substituted, for example, by $C_1$–$C_3$alkyl or halogen, Z is the atoms necessary to complete a 5- or 6-membered aromatic heterocyclic ring, with or without a fused benzene ring, and $X^\ominus$ is an anion, which is absent if an anionic group is already linked to the remainder of the molecule;

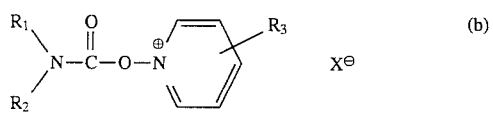

(b)

in which $R_1$, $R_2$, $R_3$ and $X^\ominus$ are as defined for the formula (a).

There are diffusable curing agents which have a curing action in the same manner on all layers within a layer system. However, there are also non-diffusing, low-molecular weight and high-molecular weight curing agents whose action is restricted to certain layers. They can be used to effect particularly strong crosslinking of individual layers, for example the protective layer. This is important if the silver-halide layer cures to a low extent owing to the increase in silver covering power and the mechanical properties must be improved with the protective layer (EP-A-0 114 699).

Colour-photographic negative materials are usually processed by development, bleaching, fixing and washing or by development, bleaching, fixing and stabilization without subsequent washing, it being possible for bleaching and fixing to be combined in a single processing step. The colour developer compound can be any developer compound which is capable of reacting, in the form of its oxidation product, with colour couplers to form azomethine or indophenol dyes. Suitable colour developers are aromatic compounds of the p-phenylenediamine type containing at least one primary amino group, for example N,N-dialkyl-p-phenylenediamine, such as N,N-diethyl-p-phenylenediamine, 1-(N-ethyl-N-methanesulfonamidoethyl)-3-methyl-p-phenylenediamine and 1-(N-ethyl-N-methoxyethyl)-3-methyl-p-phenylenediamine. Other colour developers which can be used are described, for example, in J. Amer. Chem. Soc. 73, 3106 (1951) and G. Haist, Modern Photographic Processing, 1979, John Wiley & Sons, New York 545 ff.

The colour development can be followed by an acidic stop bath or washing.

The material is usually bleached and fixed immediately after colour development. Examples of bleaches which can be used are Fe(III) salts and Fe(III) complex salts such as ferricyanides, dichromates and water-soluble cobalt complexes. Particular preference is given to iron(III) complexes of aminopolycarboxylic acids, in particular, for example, of ethylenediaminetetraacetic acid, propylenediaminetetraacetic acid, diethylenetriaminepentaacetic acid, nitrilotriacetic acid, iminodiacetic acid, N-hydroxyethylethylenediaminetriacetic acid, alkyliminodicarboxylic acids and of corresponding phosphonic acids. Other suitable bleaches are persulfates and peroxides, for example hydrogen peroxide.

The bleaching/fixing bath or fixing bath is usually followed by washing, either in countercurrent or in a plurality of tanks with their own water supply.

Favourable results can be obtained if a subsequent final bath is used which contains no or only little formaldehyde.

However, the washing can also be replaced in its entirety by a stabilizing bath, which is usually carried out in countercurrent. If formaldehyde is added, this stabilizing bath also takes on the function of a final bath.

In colour reversal materials, the first step is development with a black/white developer whose oxidation product is not capable of reacting with the colour couplers. This is followed by diffuse second exposure and then development with a colour developer, bleaching and fixing.

The present invention furthermore relates to a process for stabilizing photographic recording material comprising, on a base, at least one silver-halide emulsion layer and, if desired, at least one interlayer and/or protection layer, which comprises adding a UV absorber of the formula (I) or a corresponding homopolymer or copolymer as described above in greater detail or as defined in claim 1 to at least one of said layers.

The present invention furthermore relates to the use of compounds of the formula (I) or a corresponding homopolymer or copolymer as described in greater detail above or as defined in claim 1, for stabilizing photographic recording material comprising, on a base, at least one silver-halide emulsion layer and, if desired, at least one interlayer and/or protection layer.

The preferences described in greater detail above for the novel photographic recording material apply analogously to the novel process, the novel use and the novel compounds of the formula (I).

The examples below illustrate the invention in greater detail. In the examples, parts are parts by weight and % are % by weight. If room temperature is mentioned in an example, this is taken to mean a temperature in the range from 20°–25° C. These definitions apply in each case unless otherwise stated. Numbers directly following chemical symbols denote indices of the chemical formula, even when not subscripted.

The following abbreviations apply:

| | |
|---|---|
| THF | tetrahydrofuran |
| AIBN | α,α'-azoisobutyronitrile |
| abs. | absolute (anhydrous) |
| m.p. | melting point or melting range |
| mmHg | Torr (1 mmHg = 133,322 Pa) |
| MALDI | Matrix Assisted Laser Desorption Ionization |
| MS | mass spectrometry |
| NMR | nuclear magnetic resonance |
| GC | gas chromatography |
| GPC | gel permeation chromatography |
| DSC | differential scanning calorimetry |
| $M_n$ | number average molecular weight (unit g/mol) |
| $M_w$ | weight average molecular weight (unit g/Mol) |
| $T_g$ | glass transition temperature. |

EXAMPLE 1

Under nitrogen, a mixture of 14.2 g (30 mmol) of 2,4-diphenyl-6-[2-hydroxy-4-(3-n-butoxy-2-hydroxypropoxy)phenyl]-1,3,5-triazine, 3.5 g (38 mmol) of acryloyl chloride and 0.4 g (5 mmol) of pyridine in 100 ml of toluene is heated at 70° C. for 24 hours. 4.5 g (44 mmol) of triethylamine are added, and the mixture is heated at 70° C. for a further 6 hours. The mixture is allowed to cool, and the solid residue ((CH₃CH₂)₃N·HCl) is filtered off. The filtrate is evaporated, giving 17.5 g of the resin-like crude product. Column chromatography (silica gel 60; 230–400 mesh; eluent CH₂Cl₂/CH₃OH95/5) gives 12.5 g (79% yield) of 2,4-diphenyl-6-[2-hydroxy-4-(3-n-butoxy-2-acryloyloxypropoxy)phenyl]-1,3,5-triazine (compound 100) as a yellowish resin.

The ¹H-NMR spectrum (CDCl₃, 300 MHz) is in agreement with the desired product.

Elemental analysis for C₃₁H₃₁N₃O₅ (525.60): Theory: C: 70.84 H: 5.94 N: 7.99% Found: C: 70.80 H: 5.85 N: 8.02%

EXAMPLE 2

Under nitrogen, a mixture of 14.2 g (30 mmol) of 2,4-diphenyl-6-[2-hydroxy-4-(3-n-butoxy-2-hydroxypropoxy)phenyl]1,3,5-triazine, 8.0 g (76 mmol) of methacryloyl chloride and 0.4 g (5 mmol) of pyridine in 100 ml of toluene is heated at 80° C. for 48 hours. The excess methacryloyl chloride and the toluene are removed on a rotary evaporator. 100 ml of toluene and 4.5 g (44 mmol) of triethylamine are added, and the mixture is heated at 75° C. for 5 hours. The mixture is allowed to cool, and the solid residue ((CH₃Cl₂)₃·HCl) is filtered off. The filtrate is evaporated, giving 18.4 g of the crude product. Column chromatography (silica gel 60; 230–400 mesh; diameter 8 cm, h=30 cm; eluent CH₂Cl₂) gives 8.5 g of 2,4-diphenyl-6-[2-hydroxy-4-(3-n-butoxy-2-methacryloyloxypropoxy)phenyl]-1,3,5-triazine (compound 101) as a yellowish resin.

The ¹H-NMR spectrum (CDCl₃, 300 MHz) is in agreement with the desired product.

Elemental analysis for C₃₂H₃₃N₃O₅ (539.63): Theory: C: 71.22 H: 6.16 N: 7.79% Found: C: 70.42 H: 6.28 N: 7.57%

Intermediate for Example 3

2-[2-Hydroxy-4-(11-hydroxy-undecyloxy)-phenyl]-4,6-diphenyl- 1,3,5-triazine.

The reaction is carried out under nitrogen protection.

A mixture of 170.7 g (0.5 mol) of 2-(2,4-dihydroxyphenyl)-4,6-diphenyl-1,3,5-triazine, 28.1 g (0.5 mol) of powdered potassium hydroxide (Fluka, >85%) in 1000 ml of diglyme (Fluka, 99%) is heated at 80° C. To this yellow solution are added 155.4 g (0.6 mol) of 11-bromo-1-undecanol (Fluka, 97%). The mixture is heated at 100° C. for 40 hours. The solid is filtered hot and the filtrate is cooled to 0° C. The cristallised solid is filtered, washed with hexane and dried at 50° C./70 mmHg. There is obtained 219.5 g (85.84% yield) of 2-[2-hydroxy-4-(11-hydroxy-undecyl-oxy-phenyl-]-4,6-diphenyl-1,3,5-triazine, as a pale yellow solid. F. 131°–132° C. Analysis: C₃₂H₃₇N₃O₃ Calc. C 76.12 H 7.29 N 8.21 (511.67) Found C 75.06 H 7.46 N 8.13

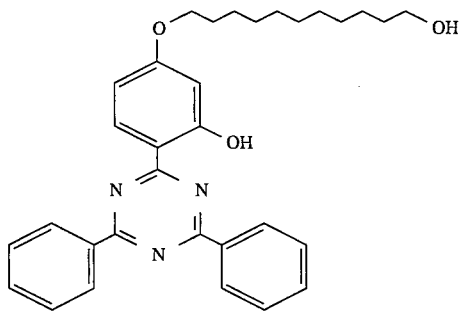

EXAMPLE 3

2-[2-Hydroxy-4-(11-acryloyl-oxy-undecyl-oxy)-phenyl-]-4,6-diphenyl-1,3,5-triazine.

The reaction is carried out under nitrogen protection.

To a mixture of 51.2 g (0.1 mol) of 2-[2-hydroxy-4-(11-hydroxy-undecyloxy-)-phenyl]-4,6-diphenyl)-1,3,5-triazine, 22.2 g (0.22 mol) of triethylamine, 500 ml of toluene (Merck, 99.5%), there is added dropwise 13.3 g (0.105 mol) of 3-chloropropionic acid chloride. Addition time:20 min. at 15° to 20° C. The mixture becomes a white suspension. The solid is filtered. Solvent is washed with water, dried with Na₂SO₄, and evaporated. The solid is filtered through a Kieselgel 60 pad, and eluted with toluene. There are obtained 44.8 g (79.2% yield) of 2-[2-hydroxy-4-(11-acryloyloxy-undecyloxy)phenyl]-4,6-diphenyl-1,3,5-triazine (compound No. 102) as a white solid. F. 123°–125° C.

Analysis: C35H39N3O4 Calc. C 74.31 H 6.95 N 7.43 (565.71) Found C 74.22 H 7.08 N 7.45

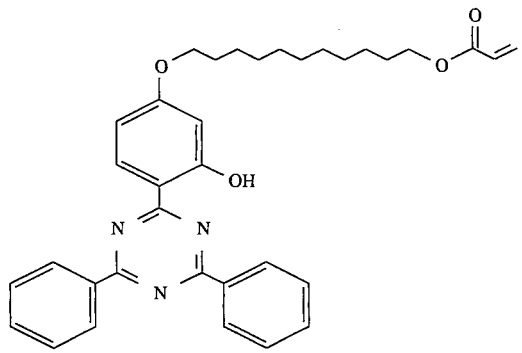

EXAMPLE 4

2-[2-Hydroxy-4-(11-methacryloyloxyundecyloxy)phenyl]-4,6-diphenyl-1,3,5-triazine The title compound (compound 103) is prepared by the method indicated in Example 3; melting point 94°–96° C.

EXAMPLE 4b

Mixture of 2-[2-Hydroxy-4-(3-vinylbenzoxy)phenyl-]-4,6-bis(2,4-dimethylphenyl-1,3,5-triazine and 2-[2-Hydroxy-4-(4-vinylbenzoxy)phenyl-]-4,6-bis(2,4-dimethylphenyl)-1,3,5-triazine The title compound (compound 105) is prepared by the method indicated in Example 8b; melting point 158°–160° C.

EXAMPLE 4c

2-[2-Hydroxy-4-(2-methacryloyloxyethoxy)phenyl]-4,6-diphenyl-1,3,5-triazine

The title compound (compound 106) is obtained as a white solid by the method indicated in Example 3.

Analysis: C₂₇H₂₃N₃O₄ (453.50) Calculated: C 71.57 H 5.11 N 9.27% Found: C 70.70 H 5.38 N 9.00%

EXAMPLE 4d

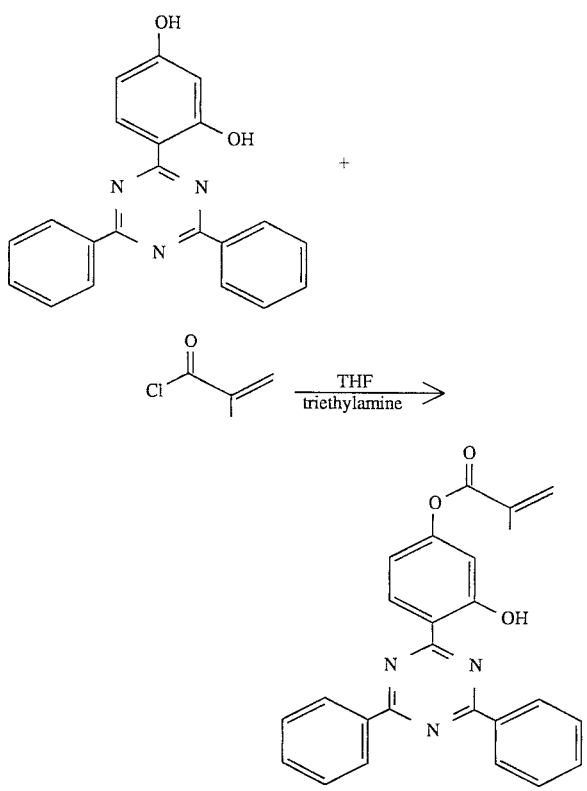

68.3g (0.2 mol) of 2-(2,4-dihydroxyphenyl)-4,6-diphenyl-1,3,5-triazine are suspended in 500 ml of THF under nitrogen. 22.3 g (0.22 mol) of triethylamine are then added. 22.9 g (0.22 mol) of methacryloyl chloride are then added dropwise at a temperature not exceeding 20° C. After a reaction time of 2.5 hours, the reaction mixture is filtered, and the filtrate is evaporated. The product is taken up in dichloromethane, and the organic phase is washed with water, dried over MgSO$_4$, filtered through silica gel and evaporated to dryness. The crude product is recrystallized from Ethylcellosolve, giving 43.6 g (53.2%) of compound (107) as a pale yellow powder of melting point 158°–160° C.

Analysis: calculated: C: 73.34 H: 4.68 N: 10.26% found: C: 73.13 H: 4.79 N: 10.23

EXAMPLE 5

2,4-Bis(2,4-dimethylphenyl)-6-[2-hydroxy-4-(3-n-butoxy-2-methacryloyloxypropoxy)phenyl]-1,3,5-triazine The title compound (compound 400) of melting point 3° C. is obtained by the method indicated in Example 2.

Intermediate for Example 6

2-[2-Hydroxy-4-(11-hydroxy-undecyloxy)-phenyl-]-4,6-bis(2,4-dimethylphenyl)-1,3,5-triazine.

The reaction is carried out under nitrogen protection.

A mixture of 79.5 g (0.2 mol) of 2-(2,4-dihydroxyphenyl)-4,6-(2,4-dimethylphenyl)-1,3,5-triazine, 11.2 g (0.2 mol) of powdered potassium hydroxide (Fluka, >85%) in 500 ml of diglyme (Fluka, 99%) are heated at 80° C. To this yellow solution are added 59.6 g (0.23 mol) of 11-bromo-1-undecanol (Fluka, 97%). The mixture is heated at 100° C. for 46 hours. The solid is filtered hot and the filtrate is cooled to 0° C. The crystals are filtered, washed with hexane and dried at 50° C./70 mm.

There are obtained 81.0 g (71.4% yield) of 2-[2-hydroxy-4-(11-hydroxyundecyloxy)phenyl]-4,6-bis-(2,4-dimethylphenyl)-1,3,5-triazine, as a pale yellow solid. F. 95°–96° C.

Analysis: C$_{36}$H$_{45}$N$_3$O$_3$ Calc. C 76.16 H 7.99 N 7.40 (567.78) Found C 75.42 H 7.92 N 7.39

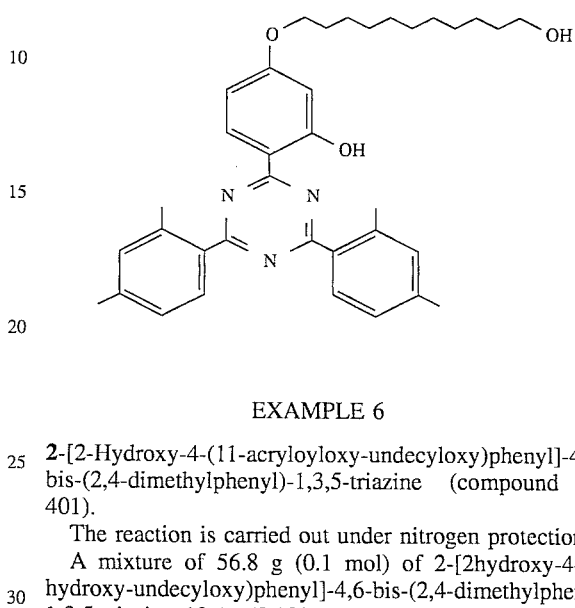

EXAMPLE 6

2-[2-Hydroxy-4-(11-acryloyloxy-undecyloxy)phenyl]-4,6-bis-(2,4-dimethylphenyl)-1,3,5-triazine (compound No. 401).

The reaction is carried out under nitrogen protection.

A mixture of 56.8 g (0.1 mol) of 2-[2hydroxy-4-(11-hydroxy-undecyloxy)phenyl]-4,6-bis-(2,4-dimethylphenyl)-1,3,5-triazine, 12.4 g (0.133mol) of acryloyl chloride (Fluka, 97%), 0.4 g of hydroquinone (Fluka, 98%), 2.0 ml of pyridine in 500 ml of toluene (Merck, 99.5%) are heated at 80° C. for 30 hours. The solution is cooled to 50° C., and 21.3 ml (0.154 mol) of triethylamine are added, followed by heating at 70° C. for 6 hours. The solid is filtered. Solvent is removed and the yellow solid is filtered through Kieselgel 60 pad, and eluted with toluene. The product is recrystallised in isopropanol. There are obtained 47.0 g (75.5% yield) of 2[2hydroxy-4-(11-acryloyloxyundecyloxy)phenyl]-2,4-bis-(2,4-dimethylphenyl)-1,3,5-triazine (compound No. 401) as a white solid; F. 81°–83° C.

Analysis: C39H47N304 Calc. C75.33 H 7.62 N 6.76 (621.82) Found C74.18 H 7.75 N 6.54

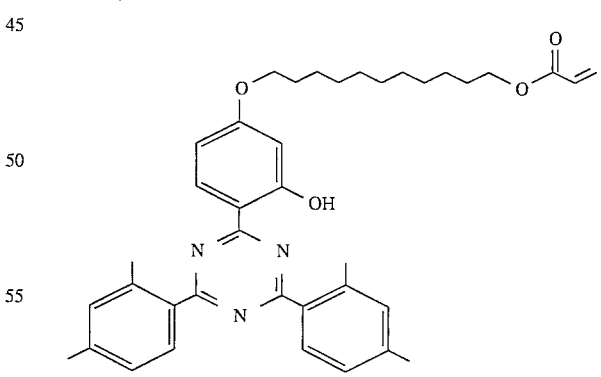

EXAMPLE 7

2,4-Bis(2,4-dimethylphenyl)-6-[2-hydroxy-4-(11-methacryloyloxyundecyloxy)phenyl]-1,3,5-triazine The title compound (compound 402) of melting point 71°–73° C. is obtained by the method indicated in Example 6.

EXAMPLE 8a 2,4-Bis(2,4-dimethylphenyl)-6-[2-hydroxy-4-(2-methacryloyloxyethoxy)phenyl]-1,3,5-triazine The title compound (compound 404) of melting point 132°–133° C. is obtained by the method indicated in Example 3.

EXAMPLE 8b

Mixture of 2-[2-hydroxy-4-(3-vinylbenzoxy)-phenyl-]-4,6-bis-(2,4-dimethylphenyl)-1,3,5-triazine and 2-[2-hydroxy-4-(4-vinylbenzoxy)-phenyl-]-4,6-bis-(2,4-dimethylphenyl)-1,3,5-triazine (compound No. 405).

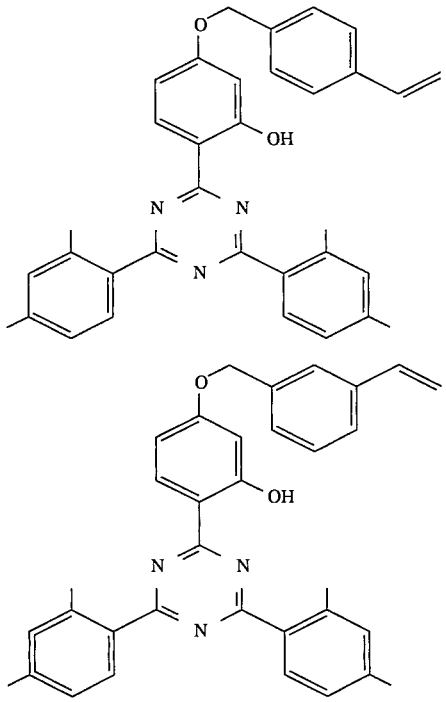

The reaction is carried out under nitrogen protection.

A mixture of 19.9 g (0.05 mol) of 2-[2,4-dihydroxyphenyl]-4,6-bis-(2,4-dimethylphenyl)-1,3,5-triazine, 8.4 g (0.055 mol) of vinylbenzyl chloride (Fluka, 98%; isomer mixture: 70% meta, 30% para), 3.1 g (0.055 mol) of potassium hydroxide and 100 ml of diglyme are heated at 110° C. for 3 hours. The suspension is cooled, 1 lt water is added, the solid is filtered and recrystallised in isopropanol. There are obtained 19.6 g (76.3% yield) of 2-[2-hydroxy-4-(3-/or 4-vinylbenzoxy)-phenyl-]-2,4-bis-(2,4-dimethylphenyl)-1,3,5-triazine (compound No. 405) as a pale yellow solid; F. 110°–114° C.

Analysis: $C_{34}H_{31}N_3O_2$ Calc. C79.51 H 6.08 N 8.18 (513.64) Found C79.53 H 5.98 N 7.98

EXAMPLE 9

Under nitrogen, a mixture of 5.0 g (11 mmol) of 2-phenyl-4,6-bis[2-hydroxy-4-(2hydroxyethoxy)phenyl]-1,3,5-triazine, 3.4 g (33 mmol) of methacryloyl chloride and 1.1 g (14 mmol) of pyridine in 35 ml of toluene is heated at 80° C. for 16 hours. The excess methacryloyl chloride and the toluene are removed at 60° C./60 mmHg. 30 ml of toluene and 3.8 g (38 mmol) of triethylamine are added, and the mixture is heated at 80° C. for 4 hours. The mixture is allowed to cool, and the solid residue is filtered off. Column chromatography (silica gel 60; 230–400 mesh; diameter 8 cm; h=30 cm; eluent toluene/ethyl acetate 1/1) gives 3.84 g of the crude product, which is recrystallized from 18-0 ml of ethyl acetate, giving 1.64 g of 2-phenyl-4,6-bis[2-hydroxy-4-(2-methacryloyloxyethoxy)phenyl]-1,3,5-triazine (compound 201) as a yellowish solid (melting point: 154°–159° C.).

The $^1$H-NMR spectrum (CDCl$_3$, 300 MHz) is in agreement with the desired product.

Elemental analysis for $C_{33}H_{31}N_3O_8$ (597.62): Theory: C: 66.32 H: 5.23 N: 7.03% Found: C: 66.04 H: 5.37 N: 7.03%

EXAMPLE 10

Under nitrogen, a mixture of 12.7 g (20 mmol) of 2-phenyl-4,6-bis[2-hydroxy-4-(3-n-butoxy-2-hydroxypropoxy)phenyl]-1,3,5-triazine, 4.3 g (46 mmol) of acryloyl chloride and 0.4 g (5 mmol) of pyridine in 80 ml of toluene is heated at 70° C. for 16 hours. After cooling to 50° C. and addition of 8.0 g (80 mmol) of triethylamine, the mixture is heated at 80° C. for 6 hours. The mixture is allowed to cool, and the solid residue ((CH$_3$CH$_2$)$_3$N.HCl) is filtered off. The filtrate is evaporated, and the residue is then taken up in 200 ml of methylene chloride. The solution is filtered through a layer of silica gel (silica gel 60; 230–400 mesh), and washed with 450 ml of methylene chloride. Removal of the solvent and drying at 80° C. give 8.8 g (59% of theory) of 2-phenyl-4,6-bis[2-hydroxy-4-(3-n-butoxy-2-acryloyloxypropoxy)phenyl]-1,3,5-triazine (compound 202) as an orange resin.

The $^1$H-NMR spectrum (CDCl$_3$, 300 MHz) is in agreement with the desired product.

Elemental analysis for $C_{41}H_{47}N_3O_{10}$ (741.84): Theory: C: 66.38 H: 6.39 N: 5.66% Found: C: 66.09 H: 6.50 N: 5.40%

Preparation of the starting compound for Examples 11 and 12

Under nitrogen, 32.4 g (128 mmol) of 11-bromo-1-undecanol are added at 80° C. to a solution of 20.0 g (54 mmol) of 2-phenyl-4,6-bis(2,4-dihydroxyphenyl)-1,3,5-triazine, 6.6 g (109 mmol) of potassium hydroxide and 150 ml of diglyne. The mixture is heated at 100° C. for 14 hours and filtered while hot, and the filtrate is cooled to 0° C. The solid which crystallizes therefrom is filtered off, pressed and dried for 24 hours under reduced pressure (60 mmHg, 60° C.), giving 27.6 g (72% yield) of 2-phenyl-4,6-bis[2-hydroxy-4-(11-hydroxyundecyloxy)phenyl]-1,3,5-triazine as a pale yellow solid of melting point 126°–135° C. The $^1$H-NMR spectrum (CDCl$_3$, 300 MHz) is in agreement with the desired product.

EXAMPLE 11

Under nitrogen, a mixture of 10.8 g (15 mmol)of 2-phenyl-4,6-bis[2-hydroxy-4-(11-hydroxyundecyloxy)phenyl]-1,3,5-triazine, 3.6 g (30 mmol) of acryloyl chloride, 0.82 g of hydroquinone and 0.3 g (3.8 mmol) of pyridine in 80 ml of toluene is heated at 78° C. for 16 hours. The excess acryloyl chloride and the toluene are removed on a rotary evaporator. The residue is dissolved in 100 ml of toluene, 16.2 g (160 mmol) of triethylamine are added, and the mixture is heated at 80° C. for 5 hours. The mixture is allowed to cool, and the solid residue ((CH$_3$CH$_2$)$_3$N.HCl) is filtered off. The filtrate is evaporated and then taken up in 50 ml of methylene chloride. The solution is filtered through silica gel (silica gel 60; 230–400 mesh) and washed with 400 ml of methylene chloride, giving, after the solvent has been stripped off, and the residue dried for 2 hours (80° C./0.1 mmHg), 10.7 g (86% yield) of 2-phenyl-4,6-bis[2-hydroxy-4-(11-acryloyloxyundecyloxy)phenyl]-1,3,5-triazine (compound 203) as a pale yellow solid (melting point 93.3° C., determined by DSC). The $^1$H-NMR spectrum (CDCl$_3$, 300 MHz) is in agreement with the desired product.

EXAMPLE 12

Under nitrogen, a mixture of 10.8 g (15 mmol) of 2-phenyl-4,6-bis[2-hydroxy-4-(11-hydroxyundecyloxy)phenyl]-1,3,5-triazine, 4.0 g (38 mmol) of methacryloyl chloride, 0.82 g of hydroquinone and 0.3 g (3.8 mmol) of pyridine in 80 ml of toluene is heated at 78° C. for 16 hours. The excess acryloyl chloride and the toluene are removed on a rotary evaporator. The residue is dissolved in 100 ml of toluene, 8.1 g (80 mmol) of triethylamine and 0.1 g of hydroquinone are added, and the mixture is heated at 70° C. for 4 hours. The mixture is allowed to cool, and the solid residue ((CH$_3$CH$_2$)$_3$N.HCl) is filtered off. The filtrate is evaporated and then taken up in 50 ml of methylene chloride. The solution is filtered through silica gel (silica gel 60; 230–400 mesh) and washed with 400 ml of methylene chloride, giving, after the solvent has been stripped off, and the residue dried for 2 hours (80 R C/0.1 mmHg), 10.9 g (85% yield) of 2-phenyl-4,6-bis[2-hydroxy-4-(11-methacryloyloxyundecyloxy)phenyl]-1,3,5-triazine (compound 204) as a pale yellow solid (melting point 68.3° C., determined by DSC). The $^1$H-NMR spectrum (CDCl$_3$, 300 MHz) is in agreement with the desired product.

EXAMPLE 13

Compound (205) is prepared according to the method described in example 11. Tg=17° C.

Analysis: C$_{41}$H$_{47}$N$_3$O$_8$ Calc. C 69.37 H 6.67 N 5.92% (709.84) Found C 68.53 H 6.67 N 6.03%

EXAMPLE 14

Compound (206) is prepared according to the method described in example 11. Tg=15° C.

Analysis: C$_{39}$H$_{43}$N$_3$O$_8$ Calc. C 68.71 H 6.36 N 6.16% (681.79) Found C 68.65 H 6.44 N 6.49

Intermediate for Example 15

2-Phenyl-4-(2-hydroxy-4-n-hexyloxy-phenyl)-6-[2-hydroxy-4-(11-hydroxy-undecyloxy)phenyl]-1,3,5-triazine.

The reaction is carried out under nitrogen protection.

A mixture of 37.3 g of 2-phenyl-4,6-bis-(2,4-dihydroxyphenyl)-1,3,5-triazine (0.100 moles), 6.6 g of powdered KOH (Fluka, >85%, 0.100 moles), 25.9 g of 11-bromo-1-undecanol(Fluka, 97%, 0.103 moles), and 0.6 g (3.6 mmoles) of Potassium iodide (Merck, 99.5%) in 160 mL of diethyleneglycol-dimethyl ether (Diglyme, Fluka, 99%) is heated under stirring at 110° C. for 4 hours 30 min. After cooling to 50° C., there are added 6.6 g (0.100 moles) of powdered KOH (Fluka, >85%) and 17.0 g (0.103 moles) of n-bromohexane (Fluka, 98%). The mixture is heated at 105° C. under stirring for 14 hours. The mixture is filtered hot and the filtrate evaporated (rotovapor). The product is submitted to a column chromatography [Kieselgel 60, 230–400 mesh; 10 cm diameter; h=30 cm; eluant: CH$_2$Cl$_2$]. The first eluted product is the di-hexyl-derivative, the second eluted title product and the third eluted product is the product dialkylated by two groups 11-hydroxyundecyl. After drying at 60° C./60 mmHg for 24 hours, there are obtained 22.5 g (35.8% yield) of 2-phenyl-4-(2-hydroxy-4-n-hexyloxy-phenyl)-6-[2-hydroxy-4-(11-hydroxy-undecyloxy)-phenyl]-1,3,5-triazine, as a pale yellow solid, F. 96°–99° C.

1H NMR (CDCl3, 300 MHz) spectrum is consistent with the desired product.

Analysis C$_{38}$H$_{49}$N$_3$O$_5$ Calc. C 72.70 H 7.87 N 6.69% (627.83) Found C 72.19 H 8.01 N 6.88

EXAMPLE 15

2-Phenyl-4-(2-hydroxy-4-n-hexyloxy-phenyl)-6-[2-hydroxy-4-(11-methacryloyloxy-undecyloxy)phenyl]-1,3,5-triazine (compound 207). The reaction is carried out under nitrogen protection. A mixture of 22.0 g (35.0 mmoles) of 2-phenyl-4-(2-hydroxy-4-n-hexyloxy-phenyl)-6-[2-hydroxy-4-(11-hydroxy-undecyloxy)phenyl]-1,3,5-triazine, 4.4 g (42.0 mmoles) of methacryloyl chloride (Fluka, 97%), 0.5 g (6.3 mmoles) of pyridine in 100 mL of toluene (Merck, 99.5%) are heated at 80°–85° C. for 21 hours. After cooling to 55° C., there are added 8.9 g (87.5 mmoles) of triethylamine (Fluka, 99.5%). The mixture is heated at 80° C. for further 7 hours then filtered hot. The filtrate is evaporated. The crude product (25.7 g) is dissolved in 120 mL of CH$_2$Cl$_2$, filtered through a Kieselgel 60 pad (230–400 mesh; 6.5 cm diameter; h=5 cm) and eluted with 380 mL of CH2Cl2. Solvent removal and drying at 80° C./0.1 mmHg for 2 hours 30 min. give 22.3 g (91.4% yield) of 2-phenyl-4-(2-hydroxy-4-hexyloxyphenyl)-6-[2hydroxy-4-(11-methacryloyloxy-undecyloxy)-phenyl]-1,3,5-triazine, as an orange resin, Tg=–13° C. (DSC).

1H NMR (CDCl3, 300 MHz) spectrum is consistent with the desired product.

Analysis C$_{42}$H$_{53}$N$_3$O$_6$ Calc. C 72.49 H 7.68 N 6.04% (695.90) Found C 72.14 H 7.48 N 5.98

EXAMPLE 16

2-Phenyl-4-[2-hydroxy-4-(11-acetyloxy-undecyloxy)phenyl]-6-[2-hydroxy-4-(11-methacryloyloxy-undecyloxy)phenyl]-1,3,5-triazine (compound 208). The reaction is carried out under nitrogen protection. A mixture of 20.0 g (28.0 mmol) 2-phenyl-4,6-bis-[2-hydroxy-4-(11-hydroxy-undecyloxy)phenyl]-1,3,5-triazine (intermediate compound for examples 11 and 12), 3.1 g (29.4 mmol) of methacryloyl chloride (Fluka, 97%), 0.2 g of hydroquinone (Fluka, 98%), 0.3 g (3.8 mmol) of pyridine in 115 ml toluene are heated in a first reaction step for 5 hours with stirring at 80° C., followed by cooling to 60° C. and addition of 4.62 g (58.8 mmol) acetic chloride and another 18 hours of heating at 60° C. After separation of the solvent and the excess acetic chloride (rotavap), the residue is dissolved in 100 ml of toluene. Addition of 7.1 g (70 mmol) triethylamine is followed by heating for 6 h with stirring at 70° C. After cooling the solid ([H$_5$C$_2$]$_3$N.HCl) is filtered off and the filtrate is concentrated to dryness. The crude product is dissolved in 100 mL of CH$_2$Cl$_2$, filtered through a layer of Kieselgel 60 (230–400 mesh) and eluted with 1000 mL of CH$_2$Cl$_2$/Methanol mixture (95:5). Separation of the solvent and drying at 40° C./60 mmHg for 48 h gives 20.8 g (90.1 of compound (208) as yellow solid, F. 70°–76° C.

EXAMPLE 17

Under nitrogen, a mixture of 7.0 g (14.1 mmol) of 2-(4-chlorophenyl)-4,6-bis[2-hydroxy-4-(2-hydroxyethoxy)phenyl]-1,3,5-triazine, 8.52 g (94.1 mmol) of acryloyl chloride and 0.3 g (3.8 mmol) of pyridine in 180 ml of toluene is heated at 75° C. for 14 hours. The excess acryloyl chloride and the toluene are removed on a rotary evaporator. After addition of 100 ml of toluene and 5.0 g (48 mmol) of triethylamine, the mixture is heated at 90° C. for 14 hours. The mixture is allowed to cool, and the solid residue $((CH_3Cl_2)_3N.Cl)$ is filtered off. The filtrate is evaporated and recrystallized from ethyl acetate, giving 4.4 g (52% yield) of 2-(4-chlorophenyl)-4,6-bis[2-hydroxy-4-(2acryloyloxyethoxy0phenyl]-1,3,5-triazine (compound 200) as a yellowish solid (melting point 115°–120° C.).

The $^1$H-NMR spectrum (CDCl$_3$, 300 MHz) is in agreement with the desired product.

Elemental analysis for $C_{31}H_{26}ClN_3O_8$ (604.02): Theory: C: 61.64 H: 4.34 N: 6.96 Cl: 5.87% Found: C: 61.36 H: 4.49 N: 6.98 Cl: 602

Intermediate for Examples 18 to 22b (i) 2-Mesityl-4,6-dichloro-1,3,5-triazine A solution of 109.5 g (0.55 mmol) of 2-bromomesitylene (purity 98%) in 150 ml of abs. THF (purity 99.5%) is added over the course of 1½ hours under nitrogen to a stirred suspension, held at 60° C., of 14.6 g (0.60 mmol) of magnesium turnings (purity 99.8%) in 100 ml of abs. THF to which an iodine crystal has been added. The mixture is subsequently kept at the reflux temperature (68° C.) for 30 minutes.

After cooling, the resultant Grignard reagent is transferred into a dropping funnel and added dropwise to a solution of 96.0 g (0.52 mmol) of cyanuric chloride (98% ) in 270 ml of THF. During the addition, which takes 1½ hours, a temperature of from 15° to 30° C. is maintained by cooling. The mixture is subsequently stirred at 25° C. for 2 hours, then poured into 2 l of an ice/water mixture containing 80 ml of 32% HCl (0.81 mol). The mixture is stirred for one hour and filtered. The filter cake is suspended in 1000 ml of water, stirred for 30 minutes and re-filtered. This operation is repeated twice. The filter cake is dried over P$_2$O$_5$ for 24 hours at 25° C. and a pressure of 60 mmHg (8000 Pa). 171.0 g of crude product are subsequently dissolved in toluene, filtered while hot and crystallized by the addition of hexane and cooling to 0° C. Filtration and drying give 82.8 g of the title product (i)

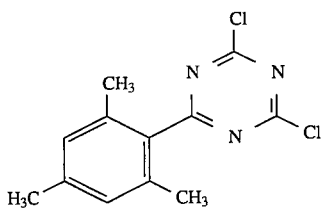

of m.p. 85°–91° C. $^1$H-NMR (CDCl$_3$, 300 MHz): δ2.22 (s, 6H); 2.32 (s, 3H); 6.95 (s, 2H).

(ii) 2-Mesityl-4,6-bis(2,4-dihydroxyphenyl)-1,3,5-triazine 148.7 g (1.21 mol) of anhydrous aluminium trichloride (purity 98%) are added with stirring to a suspension of 130.0 g (0.485 mmol) of 2-mesityl-4,6-dichloro-1,3,5-triazine (i) in 300 ml of petroleum ether with a boiling range of 110°–140° C. and 385 ml of sulfolane. During this addition, the mixture warms to 45° C. A solution of 133.5 g (1.21 mmol) of resorcinol (purity 98%) in 155 ml of sulfolane is added to the mixture over the course of 45 minutes. The mixture is warmed at 80°–85° C. for 5 hours 30 minutes with evolution of HCl. The upper phase (petroleum ether) is removed, and the lower, viscous phase is transferred while still hot into a stirred mixture of 2.1 l of methanol and 2.1 l of water. After the mixture has been stirred for 14 hours, the solid is filtered off, stirred in 2.2 l of 1 molar HCl for 1 hour and re-filtered. The filter cake is suspended in 1000 ml of water, stirred for 30 minutes and re-filtered. This operation is repeated twice. The filter cake is dried for 24 hours at 80° C. and a pressure of 60 mmHg (8000 Pa), giving 170.5 g of the title product (ii) of the formula

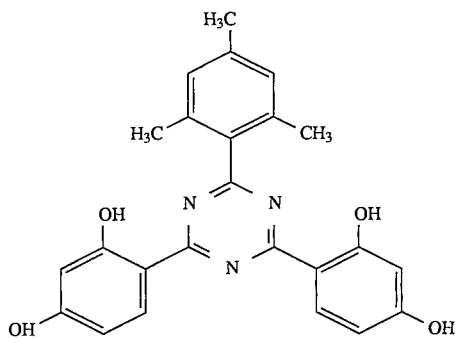

of m.p. 230°–234° C.

EXAMPLE 18

Compound (500) is prepared according to the method described in example 10. It is obtained as yellow resin; Tg.: 9° C. Analysis (C44H53N3010): Calc. C 67.42 H 6.81 N 5.36% (783.92) Found C 67.27 H 6.91 N 5.66%

EXAMPLE 19

Compound (501) is prepared according to the method described in example 10. It is obtained as 19 yellow resin, Tg.: −2° C. Analysis (C46H57N3010): Calc. C 68.04 H 7.08 N 5.18% (811.98) Found C 68.01 H 7.10 N 4.92%

EXAMPLE 20

Compound (502) is prepared according to the method described in example 12. It is obtained as a resin. Analysis (C54H73N308): Calc. C 72.70 H 8.25 N 4.71% (892.19) Found C 71.69 H 8.09 N 4.75%

EXAMPLE 21

Compound (503) is prepared according to the method described in examples 9 and 11. It is obtained as yellow resin, Tg.: 22° C. Analysis (C44H53N308): Calc. C 70.28 H 7.11 N 5.59% (751.92) Found C 69.81 H 6.87 N 5.67

Intermediate for Examples 22 and 22b

2-Mesityl-4-(2-hydroxy-4-n-hexyloxy-phenyl)-6-[2-hydroxy-4-(11-hydroxy-undecyloxy)phenyl]-1,3,5-triazine. The reaction is carried out under nitrogen protection. A mixture of 83.0 g triazine (0.200 moles) of 2-mesityl-4,6-bis-(2,4-dihydroxy-phenyl)-1,3,5-triazine, 13.2 g (0.200 moles) of powdered KOH (Fluka, >85% ), 51.8g (0.206 moles) of 11-bromo-1-undecanol (Fluka, 97%), and 1.2 g (7.2 mmoles) of Potassium iodide (Merck, 99.5%) in 300 mL of diethylene-glycol-di-methyl ether (Diglyme, Fluka, 99%) is heated under stirring at 120° C. for 3 hours. After cooling to 60° C., there are added 13.2 g of powdered KOH and 34.0 g of n-bromohexane (0.206 moles; Fluka, 98%). The mixture is heated at 110° C. under stirring for 16 hours. The mixture is filtered hot and the filtrate is evaporated (rotovapor). The product (152.1 g) is submitted to a column chromatography [Kieselgel 60; 230–400 mesh); 10 cm diameter; h=30 cm; eluant: toluene/methanol 98:2] to separate the product from the secondary product. The first eluted product is the di-hexyl-derivative, the second product eluted is the desired product and the third product is the product dialkylated by two groups 11-hydroxy-undecyl. After drying at 110° C./0.1 mmHg for 2 hours, there are obtained 55.2 g (41.2% yield) of 2-mesitylyl-4-(2-hydroxy-4-n-hexyloxyphenyl)-6-[2-hydroxy-4-(11-hydroxy-undecyloxy)-phenyl]-1,3,5-triazine, as a yellow resin which crystallises slowly at 25° C.

1H NMR (CDCl3, 300 MHz) spectrum is consistent with the desired product. Analysis ($C_{41}H_{55}N_3O_5$): Calc. C 73.51 H 8.27 N 6.27% (669.91) Found C 73.55 H 8.47 N 6.29%

EXAMPLE 22

2-Mesityl-4-(2-hydroxy-4-n-hexyloxyphenyl)-6-[2-hydroxy-4-(11-methacryloyl-oxy-undecyloxy)-phenyl]-1,3,5-triazine (compound 504). The reaction is carried out under nitrogen protection. A mixture of 10.9 g (16.0 mmoles) of 2-mesityl-4-(2-hydroxy-4-n-hexyloxyphenyl)-6-[2-hydroxy-4-(11-hydroxy-undecyloxy)-phenyl]-1,3,5-triazine, 2.0 g (19.2 mmoles) of methacryloyl chloride (Fluka, 97%), and 0.4 g (5.0 mmoles) of pyridine in 70 mL of toluene (Merck, 99.5%) are heated at 80°–85° C. for 16 hours. After cooling to 55° C., there are added 4.1 g (40.0 mmoles) of triethylamine (Fluka, 99.5%). The mixture is heated at 80° C. for further 6 hours then filtered hot. The filtrate is evaporated. The crude product (13.6 g) is dissolved in 100 mL of CH2Cl2, filtered through a Kieselgel 60 (230–400 mesh) pad (6.5 cm diameter; h=4 cm) and eluted with 380 mL of CH2Cl2. Solvent removal and drying at 80° C./0.1 mmHg for 2 hours 30 min. gives 22.3 g (91.4% yield) of 2-mesityl-4-(2-hydroxy-4-hexyloxyphenyl)-6-[2-hydroxy-4-(11-methacryloyloxy-undecyloxy)-phenyl]-1,3,5-triazine (compound 504) as a yellow resin; Tg.: −10° C. (DSC).

1H NMR (CDCl3, 300 MHz) spectrum is consistent with the desired product.

Analysis ($C_{45}H_{59}N_3O_6$): Calc. C 73.24 H 8.06 N 5.69% (737.98) Found C 73.01 H 7.76 N 5.61%

EXAMPLE 22a

Compound (505) is prepared according to the method described in example 8b. It is obtained as an orange resin; Tg. 13.3° C. (DSC).

Analysis ($C_{42}H_{37}N_3O_4$): Calc. C 77.88 H 5.76 N 6.49% (647.78) Found C 77.64 H 5.76 N 5.66%

EXAMPLE 22b

2-Mesityl-4-(2-hydroxy-4-n-hexyloxyphenyl)-6-[2-hydroxy-4-(11-acryloyloxyundecyloxy)-phenyl]-1,3,5-triazine (compound 506).

The reaction is carried out under nitrogen protection. A stirred mixture of 27.3 g (40.8 mmoles) of 2-mesityl-4-(2-hydroxy-4-n-hexyloxyphenyl)-6-[2-hydroxy-4-(11-hydroxy-undecyloxy)-phenyl]-1,3,5-triazine, 4.4 g (49.0 mmoles) of acryloyl chloride (Fluka, 97%), 0.1 g (0.9 mmoles) of hydroquinone (Fluka, 99%), and 0.75 g (9.5 mmoles) of pyridine in 170 mL of toluene (Merck, 99.5%) are heated at 70°–75° C. for 17 hours. After cooling to 50° C., there are added 20.0 g (197.6 mmoles) of triethylamine (Fluka, 99.5%). The mixture is heated at 85° C. for further 6 hours then filtered hot. The filtrate is evaporated. The crude product is dissolved in 100 mL of toluene/methanol (98:2), filtered through a Kieselgel 60 (230–400 mesh) pad (6.5 cm diameter; h=5 cm) and eluted with 400 mL of toluene/methanol (98:2). Solvent removal and drying at 80° C./0.1 mmHg for 3 hours gives 24.3 g (82.3% yield) of 2-mesityl-4-(2-hydroxy-4-hexyloxyphenyl)-6-[2-hydroxy-4-(11-acryloyloxy-undecyloxy)phenyl]-1,3,5-triazine (compound 506) as a yellow resin; Tg. −14.2° C. (DSC).

1H NMR (CDCl3, 300 MHz) spectrum is consistent with the desired product.

Analysis $C_{44}H_{57}N_3O_6$ Calc. C 73.00 H 7.94 N 5.80% (723.96) Found C 72.81 H 7.70 N 5.53%

EXAMPLE 23

Under nitrogen, a mixture of 15.9 g (20 mmol) of 2,4,6-tris[2-hydroxy-4-(3-n-butoxy-2-hydroxypropoxy)phenyl]1,3,5-triazine, 7.3 g (80 mmol) of acryloyl chloride and 0.4 g (5 mmol) of pyridine in 120 ml of toluene is heated at 75° C. for 24 hours. The excess acryloyl chloride and the toluene are removed on a rotary evaporator. The residue is dissolved in 100 ml of toluene, 10.1 g (100 mmol) of triethylamine are added, and the mixture is heated at 80° C. for 6 hours. The mixture is allowed to cool, and the solid residue (($CH_3CH_2$)$_3$N.HCl) is filtered off. The filtrate is evaporated and then taken up in 100 ml of methylene chloride. The solution is filtered through silica gel (silica gel 60; 230–400 mesh) and washed with 2000 ml of methylene chloride, giving, after the solvent has been stripped off, and the residue dried for 2 hours (90° C./0.5 mmHg), 12.0 g (63% yield) of 2,4,6-tris[2-hydroxy-4-(3-n-butoxy-2-acryloyloxypropoxy)phenyl]-1,3,5-triazine (compound 300) as a pale yellow resin.

The $^1$H-NMR spectrum (CDCl$_3$, 300 MHz) is in agreement with the desired product.

Elemental analysis for $C_{51}H_{63}N_3O_{15}$ (958.07): Theory: C: 63.94 H: 6.63 N: 4.39% Found: C: 63.24 H: 6.57 N: 4.02%

Preparation of the starting compound for Examples 24 and 25

Under nitrogen, 42.9 g (170 mmol) of 11-bromo-1-undecanol are added at 80° C. to 2,4,6-tris(2,4-dihydroxyphenyl)-1,3,5-triazine, 9.3 g (141 mmol) of potassium hydroxide and 150 ml of diglyne. The mixture is heated at 100° C. for 16 hours and filtered while hot, and the filtrate is cooled to 0° C. The crystallized solid is filtered off, pressed and dried for 48 hours under reduced pressure (60 mmHg, 70° C.), giving 24.3 g (53% yield) of 2,4,6-tris[2-hydroxy-4-(11-hydroxyundecyloxy)phenyl]-1,3,5-triazine as a pale yellow, resin-like solid.

The $^1$H-NMR spectrum (CDCl$_3$, 300 MHz) is in agreement with the desired product.

EXAMPLE 24

Under nitrogen, a mixture of 10.1 g (11 mmol) of 2,4,6-tris[2-hydroxy-4-(11-hydroxyundecyloxy)phenyl]-1,3,5-triazine, 3.6 g (30 mmol) of acryloyl chloride, 0.82 g of hydroquinone and 0.3 g (3.8 mmol) of pyridine in 80 ml of toluene is heated at 80° C. for 18 hours. The excess acryloyl chloride and the toluene are removed on a rotary evaporator. The residue is dissolved in 100 ml of toluene, 16.2 g (160 mmol) of triethylamine and 0.1 g of hydroquinone are added, and the mixture is heated at 78° C. for 5 hours. The mixture is allowed to cool, and the solid residue (($CH_3CH_2$)$_3$N.HCl) is filtered off. The filtrate is evaporated and then taken up in 100 ml of methylene chloride. The solution is filtered through silica gel (silica gel 60; 230–400 mesh) and washed with 400 ml of methylene chloride, giving, after the solvent has been stripped off, and the residue dried for 2 hours (70° C./0.1 mmHg), 7.7 g (65% yield) of 2,4,6-tris[2-hydroxy-4-(11-acryloyloxyundecyloxy)phenyl]-1,3,5-triazine (compound 301) as a pale yellow solid (melting point 72.8° C., determined by DSC).

The $^1$H-NMR spectrum (CDCl$_3$, 300 MHz) is in agreement with the desired product.

EXAMPLE 25

Under nitrogen, a mixture of 10.1 g (11 mmol) of 2,4,6-tris[2-hydroxy-4-(11-hydroxyundecyloxy)phenyl]-1,3,5-triazine, 4.2 g (30 mmol) of methacryloyl chloride, 0.82 g of hydroquinone and 0.3 g (3.8 mmol) of pyridine in 80 ml of toluene is heated at 80° C. for 18 hours. The excess acryloyl chloride and the toluene are removed on a rotary evaporator. The residue is dissolved in 100 ml of toluene, 8.1 g (80 mmol) of triethylamine and 0.1 g of hydroquinone are added, and the mixture is heated at 70° C. for 5 hours. The mixture is allowed to cool, and the solid residue ((CH$_3$CH$_2$)$_3$N.HCl) is filtered off. The filtrate is evaporated and then taken up in 100 ml of methylene chloride. The solution is filtered through silica gel (silica gel 60; 230–400 mesh) and washed with 400 ml of methylene chloride, giving, after the solvent has been stripped off, and the residue dried for 2 hours (70° C./0.1 mmHg), 7.7 g (65% yield) of 2,4,6-tris[2-hydroxy-4-(11-methacryloyloxyundecyloxy)phenyl]-1,3,5-triazine (compound 302) as a pale yellow solid (melting point 60.2° C., determined by DSC).

The $^1$H-NMR spectrum (CDCl$_3$, 300 MHz) is in agreement with the desired product.

EXAMPLE 28

Homopolymer of 2-phenyl-4-(2-hydroxy-4-hexyloxyphenyl)-6-[2-hydroxy-4-(11-methacryloyloxyundecyloxy)phenyl]-1,3,5-triazine (compound 602).

A solution of 5.2 g (7.5 mmol) of 2-(phenyl)-4-(2-hydroxy-4-hexyloxyphenyl)-6-(2-hydroxy-11-methacryloyloxyundecyloxyphenyl)-1,3,5-triazine (compound 207) in 40 ml of toluene (Fluka, 99.5% ) is treated, in a 100 ml three-neck flask under argon, with 40 mg (0.22 mmol) of α,α'-(-azobisisobutyronitrile (AIBN, Fluka 98%) and 70 mg (0.75 mmol) of n-butyl mercaptan (Fluka, 97%).

The mixture is kept at 85° C. for 16 hours with stirring. After cooling, the clear yellow solution is added dropwise with stirring to a solution of 400 ml of acetonitrile (Fluka, 99.5%).

The precipitate is decanted and taken up in 30 ml of toluene. Stripping-off of the solvent and drying for 2 hours at 80° C./0.1 mmHg gives 3.35 g (64%) of the title product (compound 602); T$_g$: 29.9° C.

1H NMR (CDCl$_3$, 300 MHz) spectrum is consistent with the desired product (no vinyl-H signal).
MALDI-MS
Mn=1698
Mw=3251

EXAMPLE 29

Copolymer of 2-phenyl-4-(2-hydroxy-4-hexyloxyphenyl)-6-[2hydroxy-4-(11-methacryloyloxyundecyloxy)phenyl]-1,3,5-triazine and n-butyl acrylate in the molar ratio 1:4

A solution of 5.2 g (7.5 mmol) of 2-phenyl-4-(2-hydroxy-4-hexyloxyphenyl)-6-(2-hydroxy-11-methacryloyloxyundecyloxyphenyl)-1,3,5-triazine (compound 207) and 3.8 g (30 mmol) of n-butyl acrylate (Fluka, 99%) in 40 ml of toluene (Fluka, 99.5%) is treated, in a 100 ml three-neck flask under argon, with 200 mg (1.12 mmol) of α,α'-azobisisobutyronitrile (AIBN, Fluka 98%) and 300 mg (3.75 mmol) of n-butyl mercaptan (Fluka, 97%). The mixture is kept at 85° C. for 17 hours with stirring. After cooling, the clear yellow solution is added dropwise with stirring to a solution of 400 ml of acetonitrile (Fluka, 99.5%).

The precipitate is decanted and taken up in 30 ml of toluene; solid impurities are removed by filtration. Stripping-off of the solvent and drying for 2 hours at 80° C./0.1 mmHg gives 6.60 g (73%) of the title product (compound 603); T$_g$: −3.5° C.
MALDI-MS
Mn=2905
Mw=4199

EXAMPLE 30

Compound (604) is prepared by the method indicated in Example 28, giving an orange-yellow resin, T$_g$.=49.8° C.

[C$_{45}$H$_{59}$N$_3$O$_6$] (737.98) calculated C 73.24H 8.06 N 5.69% found C 72.57 H 8.43 N 5.49%
M$_n$=1920
M$_w$=4198 (MALDI-MS)

EXAMPLE 31

Compound (605) is prepared by the method indicated in Example 29, giving an orange resin, T$_g$.=−4.2° C.

[C$_{45}$H$_{59}$N$_3$O$_6$]$_1$[C$_7$H$_{12}$O$_2$]$_4$ calculated C 70.11 H 8.62 N 3.36% found C 70.71 H 8.74 N 3.67%
M$_n$=3238
M$_w$=4923 (MALDI-MS)

EXAMPLE 31a

Compound (606) is prepared by the method indicated in Example 29, but replacing n-butyl acrylate by 30 mmol of n-dodecyl methacrylate; Tg. −33.4° C. MALDI-MS
Mn=2023
Mw=3661

EXAMPLE 32

Compound (607) is prepared by the method indicated in Example 28, giving a white solid.

[C$_{35}$H$_{39}$N$_3$O$_4$] (565.71) calculated C 74.31 H 6.95 N 7.43% found C 74.13H 7.16 N 7.27%
M$_n$=1938
M$_w$=3054 (MALDI-MS)

EXAMPLE 33

Compound (608) is prepared by the method indicated in Example 29.[C$_{35}$H$_{39}$N$_3$O$_4$]$_1$[C$_7$H$_{12}$O$_2$]$_4$ calculated C 70.17 H 8.13 N 3.90% found C 70.70 H 8.33 N 4.60%
M$_n$=2310
M$_w$=3341 (MALDI-MS)

EXAMPLE 34

Compound (609) is prepared by the method indicated in Example 28, giving a yellow resin.

$[C_{40}H_{49}N_3O_4]$ (635.85) calculated C 75.56 H 7.77 N 6.61% found C 74.02 H 8.06 N 6.06%

$M_n=1781$ $M_w=3669$ ( MALDI-MS )

EXAMPLE 35

Compound (610) is prepared by the method indicated in Example 29, but using only half the amount of n-butyl acrylate.

$.[C_{40}H_{49}N_3O_4]_1[C_7H_{12}O_2]_2$ calculated C 72.70 H 8.25 N 4.71% found C 71.81 H 8.41 N 4.68%

$M_n=1908$ $M_w=3111$ (GPC)

EXAMPLE 36

Compound (611) is prepared by the method indicated in Example 28, giving a yellow solid of melting point 85.7° C. (DSC).

$[C_{36}H_{41}N_3O_4]$ (579.74) calculated C 74.58 H 7.13 N 7.25% found C 73.90 H 7.15 N 7.03%

$M_n=2405$ $M_w=3701$ (MALDI-MS)

EXAMPLE 37

Compound (612) is prepared by the method indicated in Example 35, giving a yellow resin, $T_g=15.8\%$.

$[C_{36}H_{41}N_3O_4]_1[C_7H_{12}O_2]_2$ calculated C 71.83 H 7.84 N 5.03% found C 71.71 H 7.61 N 5.19%

$M_n=3241$ $M_w=4920$ (MALDI-MS)

EXAMPLE 38

Compound (613) is prepared by the method indicated in Example 28, giving a yellow solid, $T_g=59.1°$ C.

$[C_{36}H_{41}N_3O_5]$ (595.74) calculated C 72.58 H 6.94 N 7.05% found C 72.25 H 6.95 N 6.63%

$M_n=2405$ $M_w=5533$ (MALDI-MS)

EXAMPLE 39

Compound (614) is prepared by the method indicated in Example 35, giving an orange resin, $T_g=35.7°$ C.

$[C_{36}H_{41}N_3O_5]_1[C_7H_{12}O_2]_2$ calculated C 70.48 H 7.69 N 4.93% found C 70.61 H 7.76 N 5.35%

$M_n=3612$ $M_w=5264$ (MALDI-MS)

EXAMPLE 40

Compound (615) is prepared by the method indicated in Example 35; Tg. 66.5° C.

$M_n=2111$ $M_w=3174$ (MALDI-MS)

EXAMPLE 41

Compound (616) is prepared by the method indicated in Example 35; Tg. 59.8° C.

$[C_{34}H_{31}N_3O_2]_1 [C_7H_{12}O_2]_2$ $M_n=2223$ $M_w=3634$ (MALDI-MS)

Use Examples

EXAMPLE 50

A gelatin layer containing silver bromide and yellow coupler (Y-9) is applied to a polyethylene-coated base material. A further gelatin layer contains an UV absorber of formula I.

The composition of the gelatin layers is described in the following table (components per $m^2$ of base material, respectively):

| component | AgBr-layer | UVA-layer |
|---|---|---|
| gelatin | 5.15 g | 1.2 g |
| curing agent | 300 mg | 40 mg |
| wetting agent | 85 mg | 200 mg |
| silver bromide | 260 mg | — |
| yellow coupler | 854 mg | — |
| trikresyl phosphate | 285 mg | — |
| UV absorber | — | 350 mg |

The curing agent is the potassium salt of 2,4-dichloro-6-hydroxytriazine, and the wetting agent is Triton B (benzyl-trimethylammoniumhydroxid).

For the purpose of comparison, an equivalent sample is prepared without compound of formula I (UVA).

A step wedge having a density difference of 0.30 logE per step is exposed onto each of the resultant samples and then processed in accordance with the manufacturer's instructions by the Kodak RA-4 process for colour negative papers.

After exposure and processing, the remission density in the blue region for the yellow step having a density of 0.9 to 1.1 of the wedge is measured. The wedge is then exposed in an Atlas exposure unit with 60 kJ/cm$^2$, and the remission density is re-measured. The drop in yellow dye density $(-\Delta D_B)$ in percent is given in the following table.

Table: Drop in yellow dye density $(-\Delta D_B)$ after exposure

| yellow coupler | UVA (compound No.) | $-\Delta D_B$ |
|---|---|---|
| Y-9 | — | 80% |
| Y-9 | (605) | 40% |

The drop in yellow dye density $(-\Delta D_B)$ is greatly reduced when a compound of formula I is used as stabilizer compared with the sample containing no stabilizer.

EXAMPLE 51

A gelatin layer of the following composition (per m$^2$) is applied in the conventional manner to a polyester base:

| Component | Amount |
|---|---|
| Gelatin | 1200 mg |
| Tricresyl phosphate | 510 mg |
| Curing agent | 40 mg |
| Wetting agent | 100 mg |

-continued

| Component | Amount |
| --- | --- |
| Comp. of the formula (I) | 400 mg |

The curing agent is the potassium salt of 2-hydroxy-4,6-dichloro-1,3,5-triazine. The wetting agent is sodium 4,8-diisobutylnaphthalene-2-sulfonate.

The gelatin layers are dried at 20° C. for 7 days.

Compounds (202), (300), (600) and (601) give clear transparent layers which are suitable for a photographic recording material.

EXAMPLE 52

A gelatin layer containing silver bromide, magenta coupler (M-6) and, as stabilizer, a compound of the formula (I) is applied to a polyethylene-coated base material.

The gelatin layer contains the following components (per $m^2$ of base material):

| Component | AgBr layer |
| --- | --- |
| Gelatin | 5.15 g |
| Curing agent | 300 mg |
| Wetting agent | 85 mg |
| Silver bromide | 260 mg |
| Magenta coupler | 325 mg |
| Tricresyl phosphate | 162 mg |
| Stabilizer | 114 mg |

The curing agent is the potassium salt of 2,4-dichloro-6-hydroxytriazine, and the wetting agent is the sodium salt of diisobutylnaphthalenesulfonic acid.

A step wedge having a density difference of 0.15 logE per step is exposed onto each of the resultant samples and then processed in accordance with the manufacturer's instructions by the Kodak RA-4 process for colour negative papers.

After exposure and processing, the remission density in the green region for the magenta step having a density of 0.9 to 1.1 of the wedge is measured. The wedge is then exposed behind a UV absorber filter in an Atlas exposure unit with 15 $kJ/cm^2$, and the remission density is re-measured. The drop in magenta dye density (−ΔD) is greatly reduced when compounds (202), (300), (600) or (601) are used as stabilizer compared with the sample containing no stabilizer.

What is claimed is:

1. A photographic recording material comprising, on a base, a silver-halide emulsion layer or a silver-halide emulsion layer and additionally an interlayer and/or a protection layer, and containing in a layer a UV absorber, wherein said UV absorber is a homopolymer obtained by addition polymerization of a monomer of the formula I, a copolymer of different compounds of the formula I, or a copolymer of a compound of the formula I and a further ethylenically unsaturated compound

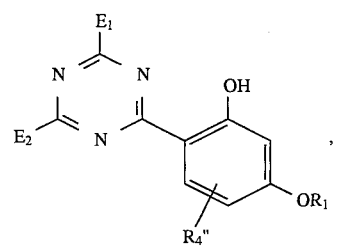

in which $E_1$ and $E_2$, independently of one another, are each a group of the formula Ia or Ib

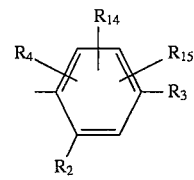

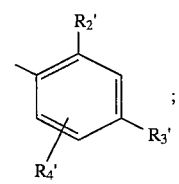

$R_1$ is —A, —$CH_2$—$CH(XA)$—$CH_2$—O—$R_7$, —$CR_8R'_8$—$(CH_2)_1$—XA, —$CH_2$—$CH(OA)$—$R_9$, —$CH_2$—$CH(OH)$—$CH_2$—XA,

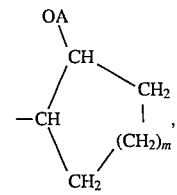

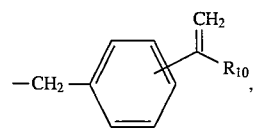

—$CH_2$—$C(=CH_2)$—$R_{10}$, —$(CH_2)_p$—$SiR_{11}R_{11}'$—$CH=CH_2$, —$C(=O)$—$(CH_2)_q$—$CH=CH_2$, —$CHR_8$—$(CH_2)_r$—$C(=O)$—O—$CH_2$—$CH(OH)$—$CH_2$—OA, —$CR_8R'_8$—$(CH_2)_1$—$C(=O)$—XA or —$C(=O)$—O—$CH_2$—$C(=CH_2)$—$R_{10}$;

A is —$C(=O)$—$CR_5=CH$—$R_6$;

$R_2$, independently of one another, are H, $C_1$–$C_{12}$alkyl, $C_5$–$C_{12}$cycloalkyl, $C_3$–$C_6$alkenyl, halogen, phenyl or trifluoromethyl;

$R_2'$, independently of one another, are $C_1$–$C_{18}$alkoxy, $C_3$–$C_{18}$alkenoxy, —O—CO—$R_{12}$, —OH or —OA;

$R_3$ and $R_3'$, independently of one another, are H, —OH, —$OR_1$, —$OR_{131}$, $C_1$–$C_{18}$alkyl, $C_3$–$C_{18}$alkenyl, $C_6$–$C_{12}$cycloalkyl, halogen, trifluoromethyl, phenyl, phenyl-$C_1$–$C_4$alkyl, —CN, $C_1$–$C_{18}$alkyl-S(=O)$_t$— or phenyl-S(=O)$_t$—;

$R_4$, $R_4'$ and $R_4''$, independently of one another, are H, $C_1$–$C_{18}$alkyl, $C_3$–$C_6$alkenyl, —$OR_{131}$, halogen, trifluoromethyl, phenyl, phenyl-$C_1$–$C_4$alkyl, mono- to tri-$C_1$–$C_4$alkyl-substituted phenyl-$C_1$–$C_4$alkyl, —CN, $C_1$–$C_{18}$alkyl-S(=O)$_t$— or phenyl-S(=O)$_t$—;

$R_5$ is H, —$CH_2$—$COOR_{13}$, $C_1$–$C_4$alkyl or —CN;

$R_6$ is H, —$COOR_{13}$, $C_1$–$C_{17}$alkyl or phenyl;

$R_7$ is $C_1$–$C_{18}$alkyl, $C_5$–$C_{12}$cycloalkyl, $C_3$–$C_{18}$alkenyl; phenyl; phenyl which is substituted by one to three $C_1$–$C_8$alkyl, $C_1$–$C_8$alkoxy, $C_3$–$C_8$alkenoxy, halogen or trifluoromethyl radicals; phenyl-$C_1$–$C_4$alkyl; $C_3$–$C_{50}$alkyl which is interrupted by —O—; 1-adamantyl; 2-adamantyl; norbornyl; 2-methylnorbornyl, —C(=O)—$R_{12}$ or —A;

$R_8$ and $R_8'$, independently of one another, are H; $C_1$–$C_{18}$alkyl; phenyl; phenyl which is substituted by one to three $C_1$–$C_8$alkyl, $C_1$–$C_8$alkoxy, $C_3$–$C_8$alkenoxy, halogen or trifluoromethyl radicals; or are phenyl-$C_1$–$C_4$alkyl;

$R_9$ is $C_1$–$C_{18}$alkyl, phenyl or phenyl-$C_1$–$C_4$alkyl;

$R_{10}$ is H or —$CH_3$;

$R_{11}$ and $R_{11}'$, independently of one another, are $C_1$–$C_4$alkyl or phenyl or phenyl which is substituted by one to three $C_1$–$C_8$alkyl, $C_1$–$C_8$alkoxy, $C_3$–$C_8$alkenoxy, halogen or trifluoromethyl radicals;

$R_{12}$ is H, $C_{1-C18}$alkyl, phenyl, phenyl-$C_1$–$C_4$alkyl, $C_5$–$C_{12}$cycloalkyl, $C_1$–$C_{12}$alkoxy, phenoxy, norborn-2-yl, 5-norbornen-2-yl or 1-adamantyl;

$R_{13}$ is $C_1$–$C_{18}$alkyl; $C_3$–$C_{18}$alkenyl; phenyl; $C_5$–$C_{12}$cycloalkyl; $C_3$–$C_{50}$alkyl which is interrupted by —O—; phenyl which is substituted by one to three $C_1$–$C_8$alkyl, $C_1$–$C_8$alkoxy, $C_3$–$C_8$alkenoxy, halogen or trifluoromethyl radicals; phenyl-$C_1$–$C_4$alkyl; 2-adamantyl;

norbornyl or 2-methylnorbornyl;

$R_{14}$ and $R_{15}$, independently of one another, are H, $C_1$–$C_{18}$alkyl, $C_3$–$C_{18}$alkenyl, $C_6$–$C_{12}$cycloalkyl, halogen, trifluoromethyl, phenyl, phenyl-$C_1$–$C_4$-alkyl, —CN, $C_1$–$C_{18}$alkyl-(S=O)$_t$—, phenyl-(S=O)$_t$— or —$OR_{131}$;

$R_{131}$ is $C_1$–$C_{18}$alkyl; $C_1$–$C_{18}$alkyl which is substituted by —OH, $C_1$–$C_{18}$alkoxy, $C_5$–$C_{12}$cycloalkoxy, $C_3$–$C_6$alkenyloxy, halogen, —$COOR_{13}$, —$CONH_2$, —$COHNR_{132}$, —$CON(R_{132})(R_{133})$, —$NHCOR_{12}$, —CN, —$OCOR_{12}$, phenoxy and/or by phenoxy which is substituted by $C_1$–$C_{18}$alkyl, $C_1$–$C_{18}$alkoxy or halogen; or is $C_3$–$C_{18}$alkenyl;

$C_6$–$C_{12}$cycloalkyl; $C_1$–$C_4$alkyl- and/or —$OCOR_{12}$-substituted $C_6$–$C_{12}$cycloalkyl; $C_3$–$C_{50}$alkyl which is interrupted by —O—; $C_3$–$C_{50}$alkyl which is interrupted by —O— and substituted by —OH or —O—CO—$R_{12}$; phenyl; phenyl-$C_1$–$C_4$alkyl; —$COR_{12}$ or —$SO_2R_{12}$;

$R_{132}$ and $R_{133}$, independently of one another, are $C_1$–$C_{12}$alkyl, $C_3$–$C_{12}$alkoxyalkyl, $C_4$–$C_{16}$dialkylaminoalkyl or $C_5$–$C_{12}$cycloalkyl; or $R_{132}$ and $R_{133}$ together are $C_3$–$C_9$alkylene, $C_3$–$C_9$oxaalkylene or -azaalkylene;

X is —$NR_8$, —O—, —NH—($C_nH_{2n}$)—NH— or —O—($C_kH_{2k}$)—NH;

k is a number from 2 to 4;

l is a number from 0 to 19;

m is a number from 2 to 8;

n is a number from 0 to 4;

p is a number from 0 to 10;

q is a number from 1 to 8;

r is a number from 0 to 18; and t is the number 0, 1 or 2.

2. A photographic recording material according to claim 1 comprising, on a base, a silver-halide emulsion layer or a silver-halide emulsion layer and additionally an interlayer and/or a protection layer, and containing in a layer a UV absorber, wherein said UV absorber is a homopolymer obtained by addition polymerization of a monomer of the formula Ic, a copolymer of different compounds of the formula Ic, a copolymer of a compound of the formula Ic and a further ethylenically unsaturated compound, or a compound of the formula Ic in which

A —C(=O)—$CR_5$=CH—$R_6$;

$R_1$, independently of one another, are —A, —$CH_2$—CH(OA)—$CH_2$—O—$R_7$, —$CHR_8$—($CH_2$)$_l$—OA, —$CH_2$—CH(OA)—$R_9$, —$CH_2$—CH(OH)—$CH_2$—OA, —$CH_2$—C(=$CH_2$)—$R_{10}$, —($CH_2$)$_p$—$SiR_{11}R_{11}'$—CH=$CH_2$, —C(=O)—($CH_2$)$_q$—CH=$CH_2$, —$CHR_8$—($CH_2$)$_r$—C(=O)—O—$CH_2$—CH(OH)—$CH_2$—OA or —C(=O)—O—$CH_2$—C(=$CH_2$)—$R_{10}$;

$R_2''$, independently of one another, are H, —OH, —OA, $C_1$–$C_{12}$alkyl, cyclohexyl, $C_3$–$C_6$alkenyl, $C_1$–$C_{18}$alkoxy, $C_3$–$C_{18}$alkenoxy, halogen, phenyl or trifluoromethyl;

$R_3$ and $R_3'$, independently of one another, are H, —OH, —$OR_1$, $C_1$–$C_{12}$alkyl, cyclohexyl, $C_3$–$C_6$alkenyl, $C_1$–$C_{18}$alkoxy, $C_3$–$C_{18}$alkenoxy, halogen, trifluoromethyl, phenyl, phenoxy, phenyl-$C_1$–$C_4$alkyl, phenyl-$C_1$–$C_4$alkoxy, —CN, $C_1$–$C_{18}$alkyl-S(=O)$_t$— or phenyl-S(=O)$_t$—;

$R_4$, $R_4'$ and $R_4''$, independently of one another, are H, $C_1$–$C_{12}$alkyl, $C_3$–$C_6$ alkenyl, $C_1$–$C_{18}$alkoxy, $C_3$–$C_{18}$alkenoxy, halogen, trifluoromethyl, phenyl, phenoxy, phenyl-$C_1$–$C_4$alkyl, mono- to tri-$C_1$–$C_4$alkyl-substituted phenyl-$C_1$–$C_4$alkyl, phenyl-$C_1$–$C_4$alkoxy, —CN, $C_1$–$C_{18}$alkyl-S(=O)$_t$— or phenyl-S(=O)$_t$—;

$R_5$ is H, —$CH_2$—$COOR_{13}$, $C_1$–$C_4$alkyl or —CN;

$R_6$ is H, —$COOR_{13}$, $C_1$–$C_{17}$alkyl or phenyl;

$R_7$ is $C_1$–$C_{18}$alkyl, cyclohexyl, $C_3$–$C_{18}$alkenyl, phenyl, phenyl which is substituted by one to three $C_1$–$C_8$alkyl, $C_1$–$C_8$alkoxy, $C_2$–$C_8$alkenoxy, halogen or trifluoromethyl radicals, phenyl-$C_1$–$C_4$alkyl or —C(=O)—$R_{12}$;

$R_8$ is H or $C_1$–$C_{18}$alkyl;

$R_9$ is $C_1$–$C_{18}$alkyl, phenyl or phenyl-$C_1$–$C_4$alkyl;

$R_{10}$ is H or —$CH_3$;

$R_{11}$ and $R_{11}'$, independently of one another, are $C_1$-$C_4$alkyl or phenyl or phenyl which is substituted by one to three $C_1$-$C_8$alkyl, $C_1$-$C_8$alkoxy, $C_3$-$C_8$alkenoxy, halogen or trifluoromethyl radicals;

$R_{12}$ is $C_1$-$C_{18}$alkyl, $C_2$-$C_{18}$alkenyl or phenyl;

$R_{13}$ is $C_1$-$C_{18}$alkyl, $C_3$-$C_{18}$alkenyl or phenyl;

l is a number from 0 to 19;

p is a number from 0 to 10;

q is a number from 1 to 8;

r is a number from 0 to 18; and t is the number 0, 1 or 2.

3. A photographic recording material according to claim 1, in which, in the formula (I), the radicals $R_1$, independently of one another, are —A, —$CH_2$—CH(XA)—$CH_2$—O—$R_7$, —$CR_8R_8'$—$(CH_2)_l$—XA, —$CH_2$—CH(OA)—$R_9$, —$CH_2$—CH(OH)—$CH_2$—XA,

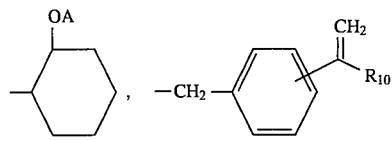

—$CHR_8$—$(CH_2)_r$—C(=)—O—$CH_2$—CH(OH)—$CH_2$—OA;

$R_2$ is H, $C_1$-$C_4$ alkyl, $C_3$alkenyl, $C_1$-$C_4$alkoxy, $C_3$alkenoxy, F, Cl or phenyl;

$R_2'$ is $C_1$-$C_4$alkoxy, $C_3$alkenoxy, —O—$COR_{12}$, —OA or —OH;

$R_3$ and $R_3'$, independently of one another, are H, —OH, —$OR_1$, —$OR_{131}$, $C_1$-$C_4$alkyl, cyclohexyl, $C_3$alkenyl, F, Cl, trifluoromethyl, phenyl, benzyl or —CN;

$R_4'$ and $R_4''$, independently of one another, are H, $C_1$-$C_4$alkyl, $C_3$alkenyl, $C_1$-$C_4$alkoxy, $C_3$alkenoxy, F, Cl, trifluoromethyl, phenyl, phenyl-$C_1$-$C_3$alkyl or —CN;

$R_5$ is H or —$CH_3$;

$R_6$ is H, —$COOR_{13}$, —$CH_3$ or phenyl;

$R_7$ is $C_1$-$C_8$alkyl, cyclohexyl, $C_2$-$C_8$alkenyl, phenyl, or phenyl which is substituted by one to three $C_1$-$C_4$alkyl or $C_1$-$C_4$alkoxy substituents, or benzyl;

$R_8$ and $R_8'$, independently of one another, are H or $C_1$-$C_{18}$alkyl;

$R_9$ is $C_1$-$C_{10}$alkyl, phenyl or benzyl;

$R_{12}$ is H, $C_1$-$C_{18}$alkyl, phenyl, phenyl-$C_1$-$C_4$alkyl or cyclohexyl;

$R_{13}$ is $C_1$-$C_4$alkyl, $C_3$alkenyl, cyclohexyl, phenyl-$C_1$-$C_4$alkyl or phenyl;

$R_4$, $R_{14}$ and $R_{15}$, independently of one another, are H, F, Cl, $C_1$-$C_4$alkoxy, $CF_3$, phenyl, CN or $C_1$-$C_4$alkyl;

$R_{131}$ is $C_1$-$C_{18}$alkyl, $C_3$-$C_{18}$alkyl which is substituted by —OH, $C_1$-$C_{18}$alkoxy, $C_5$-$C_{12}$cycloalkoxy, —$COOR_{13}$, —$CONH_2$, —$COHNR_{132}$, —$CON(R_{132})(R_{133})$, —$NHCOR_{12}$, —CN, —$OCOR_{12}$ and/or phenoxy, or is $C_3$alkenyl, $C_6$-$C_{12}$cycloalkyl, $C_3$-$C_{50}$alkyl which is interrupted by one or more —O— and may be substituted by OH or —O—$COR_{12}$, or is phenyl, phenyl-$C_1$-$C_4$alkyl, —$COR_{12}$ or —$SO_2R_{12}$;

X is —O— or —$NR_8$—;

l is a number from 1 to 19; and r is a number from 0 to 10.

4. A photographic recording material according to claim 1, in which the UV absorber is derived from a compound of the formula I, in which the radicals $E_1$ and $E_2$, independently of one another, are each a group of the formula Ib or Ie,

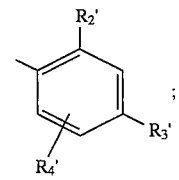

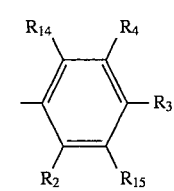

and in which $R_4'$ and $R_4''$ are in the meta-position to the triazine ring.

5. A photographic recording material according to claim 1, in which the radicals A is —C(=O)—$CR_5$=CH—$R_6$;

$R_1$, independently of one another, are —A, —$CH_2$—CH(OA)—$CH_2$—O—$R_7$, —$CH_2$—CH(OA)—$R_9$,

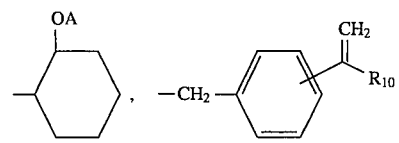

or —$CHR_8$—$(CH_2)_l$—OA;

$R_2$ is H, —$CH_3$, $C_1$-$C_2$alkoxy, $C_3$alkenoxy or Cl;

$R_2'$ is —OH;

$R_3$ is H, —$CH_3$, $C_1$-$C_4$alkoxy, $C_3$alkenoxy, F, Cl, phenyl, benzoxy or —CN;

$R_3'$ is —$OR_1$ or —$OR_{131}$;

$R_4$, $R_{14}$ and $R_{15}$, independently of one another, are H, $OCH_3$, F, Cl, phenyl, CN or $CH_3$;

$R_4'$ and $R_4''$, independently of one another, are H, —$CH_3$, $C_3$alkenyl, —$OCH_3$, $C_3$alkenoxy, F, Cl, phenyl-$C_1$-$C_3$alkyl or —CN;

$R_5$ is H or —$CH_3$;

$R_6$ is H or —$CH_3$;

$R_7$ is $C_1$-$C_8$alkyl, cyclopentyl, cyclohexyl, $C_3$alkenyl, phenyl or benzyl;

$R_8$ is H or $C_1$-$C_{18}$alkyl;

$R_9$ is $C_1$-$C_{10}$alkyl or phenyl;

$R_{12}$ is $C_1$-$C_{18}$alkyl, phenyl or cyclohexyl;

$R_{131}$ is $C_1$-$C_{18}$alkyl or $C_3$-$C_{18}$alkyl which is substituted by $C_1$-$C_{18}$alkoxy, OH, phenoxy, —$NHCOR_{12}$ and/or —$OCOR_{12}$; and l is a number from 1 to 19.

6. A photographic recording material according to claim 1, in which, in the formula (I), A is —C(=O)—$CR_5$=CH—$R_6$;

$R_1$, independently of one another, are —A, —$CH_2$—CH(OA)—$CH_2$—O—$R_7$, —$CH_2$—CH(OA)—$R_9$,

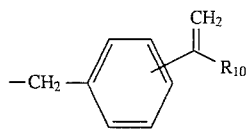

or —CH$_2$—(CH$_2$)$_l$—OA;

R$_2$ is H or CH$_3$;

R$_2$' is —OH;

R$_3$ is H, —CH$_3$, OCH$_3$, Cl or phenyl;

R$_3$' is —OR$_1$ or —OR$_{131}$;

R$_4$ is H, Cl, OCH$_3$, F or CH$_3$;

R$_4$' and R$_4$" are H or CH$_3$;

R$_{14}$ and R$_{15}$ are hydrogen, CH$_3$ or OCH$_3$;

R$_5$ is H or —CH$_3$;

R$_6$ is H;

R$_7$ is C$_1$–C$_8$alkyl;

R$_9$ is C$_1$–C$_{10}$alkyl;

R$_{12}$ is C$_1$–C$_8$alkyl;

R$_{131}$ is C$_1$–C$_{18}$alkyl or C$_3$–C$_{18}$alkyl which is substituted by —OCOR$_{12}$; and l is a number from 1 to 10.

7. A photographic recording material according to claim 1, wherein the UV absorber is a homopolymer obtained by addition polymerization of a monomer of the formula I, a copolymer of different compounds of the formula I or a copolymer of a compound of the formula I and a comonomer, where the comonomer is selected from the group consisting of acrylic acid, methacrylic acid, acrylates, methacrylates, acrylamides, methacrylamides, vinyl ethers, styrene, styrene derivatives, vinylpyridines, acrylonitrile, methacrylonitrile, vinylpyrrolidone, derivatives of vinylpyrrolidone, and ethylenically unsaturated derivatives of sterically hindered amines, 2-(2'-hydroxyphenyl)benzotriazoles, 2-hydroxybenzophenones, derivatives of cinnamic acid and sterically hindered phenols.

8. A photographic recording material according to claim 7, where the comonomer conforms to one of formulae (II)–(VII)

(II) R$_{18}$—CH=C(R$_{17}$)—C(=O)—X'—R$_{20}$, in which X' is —O— or —NR$_{19}$—;

R$_{17}$ is H, C$_1$–C$_4$alkyl, —CH$_2$—COOR$_{21}$, —Cl or —CN;

R$_{18}$ is H, —COOR$_{21}$ or —CH$_3$;

R$_{19}$ is H, C$_1$–C$_8$alkyl, C$_4$–C$_{12}$cycloalkyl, —N(R$_X$)$_2$-substituted C$_1$–C$_4$alkyl, —S(=O)—R$_X$, —C(CH$_3$)$_2$—CH$_2$—C(=O)—CH$_3$, —C(CH$_3$)$_2$—CH$_2$—SO$_3$M, —(CH$_2$)$_s$—SO$_3$M or

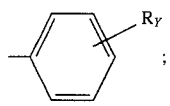

R$_{20}$ is H; C$_1$–C$_{18}$alkyl; C$_3$–C$_{18}$alkenyl; C$_2$–C$_{30}$alkyl which is interrupted by —O—; C$_2$–C$_{30}$alkyl which is interrupted by —O— and substituted by OH; or —(CH$_2$)$_s$—SO$_3$M;

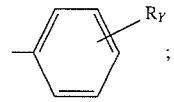

—CH$_2$F, —CH$_2$Cl, —CH$_2$CN, —CH$_2$CH$_2$Cl, —CH$_2$CH$_2$CN, —CH$_2$CH$_2$—COOR$_X$, C$_7$–C$_{11}$phenylalkyl, naphthyl, —N(R$_X$)$_2$-substituted C$_1$–C$_4$alkyl, adamantyl or C$_6$–C$_{12}$cycloalkyl;

R$_{21}$ is H, C$_1$–C$_{18}$alkyl, phenyl or C$_3$–C$_{18}$alkenyl;

R$_X$ is C$_1$–C$_4$alkyl or phenyl;

R$_Y$ is H, C$_1$–C$_{12}$alkyl, phenyl, —CO—OR$_X$, —CN, —F, or —Cl;

M is H or an alkali metal; and s is a number from 1 to 5;

(III) R$_{22}$—C(=O)—O—CH=CH$_2$, in which R$_{22}$ is C$_1$–C$_{19}$alkyl or phenyl;

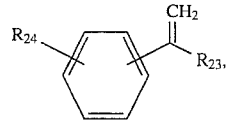

(IV)

in which R$_{23}$ is H or —CH$_3$;

R$_{24}$ is H, —CR$_{23}$=CH$_2$, —C(O)-phenyl or —SO$_3$M; and

M is H or an alkali metal;

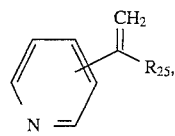

(V)

in which R$_{25}$ is H or —CH$_3$;

(VI) CH$_2$=CR$_{26}$—R$_{27}$, in which R$_{26}$ is H, —F, —Cl or —CH$_3$ and R$_{27}$ is —Cl, —Br, —F or —CN;

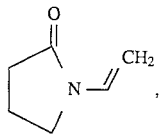

(VII)

or is a copolymerizable ethylenically unsaturated derivative of a compound which contains the structural unit

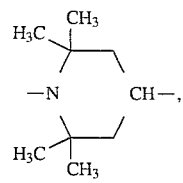

where the three free bonds are saturated by H or an organic substituent, and the molecule contains at least one polymerizable, ethylenically unsaturated double bond; the structural unit

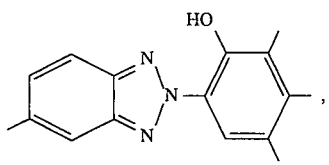

where the four free bonds are saturated by H or organic substituents, and the molecule contains at least one polymerizable, ethylenically unsaturated double bond; the structural unit

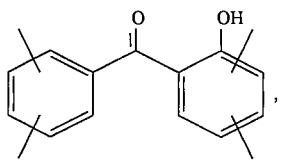

where the four free bonds are saturated by H or organic substituents, and the molecule contains at least one polymerizable, ethylenically unsaturated double bond; the structural unit

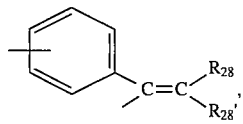

in which $R_{28}$ and $R_{28}'$ are independently CN or $COOR_{13}$ and $R_{13}$ is as defined in claim 1, and the two free bonds are saturated by H or organic substituents, and the molecule contains at least one polymerizable, ethylenically unsaturated double bond; or the structural unit

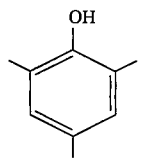

where the three free bonds are saturated by organic substituents, and the molecule contains at least one polymerizable, ethylenically unsaturated double bond.

9. A photographic recording material according to claim 8, wherein the UV absorber is a copolymer of a compound of the formula (I) and a comonomer selected from compounds of the formulae (II), (III), (IV) and (VII).

10. A photographic recording material according to claim 1, wherein the UV absorber is present in an amount of 0.05 to 10 g per m².

11. A photographic recording material according to claim 1, wherein the UV absorber is in a layer above the green-sensitive layer.

12. A photographic recording material according to claim 1, which comprises in a layer a hydrophobic homopolymer or copolymer of a monomer of the formulae II, III, IV, V, VI and/or VII according to claim 8, in addition to the UV absorber.

13. A photographic recording material according to claim 12, comprising the copolymeric UV absorber and the hydrophobic polymer in a layer, which material is obtainable by dissolving the UV absorber and the hydrophobic polymer in an organic solvent and then emulsifying and dispersing the solution in an aqueous medium and introducing the dispersion into the photographic system.

14. A photographic recording material comprising, on a base, a silver-halide emulsion layer or a silver-halide emulsion layer and additionally an interlayer and/or a protection layer, and containing in a layer a UV absorber, wherein said UV absorber is a compound of the formula I

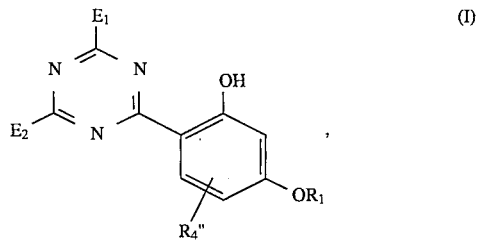

in which $E_1$ and $E_2$, independently of one another, are each a group of the formula Ia or Ib

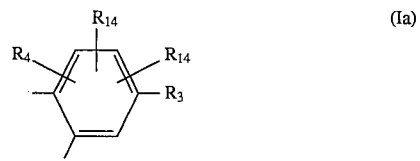

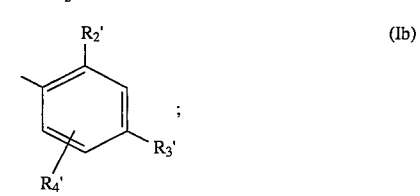

$R_1$ is —A,

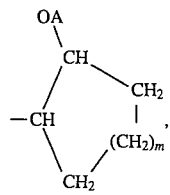

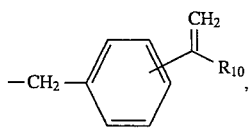

—$CH_2$—C(=$CH_2$)—$R_{10}$, —($CH_2$)$_p$—$SiR_{11}R_{11}'$—CH=$CH_2$, —C(=O)—($CH_2$)$_q$—CH=$CH_2$, —$CHR_8$—($CH_2$)$_r$—C(=O)—O—$CH_2$—CH(OH)—$CH_2$—OA, —$CR_8R'_8$—($CH_2$)$_1$—(=O)—XA or —C(=O)—O—$CH_2$—C(=$CH_2$)—$R_{10}$, and, in case that $E_1$ or $E_1$ and $E_2$ are a group of formula Ib, $R_1$ is also —$CH_2$—CH(XA)—$CH_2$—O—$R_7$, —$CR_8R'_8$—($CH_2$)$_1$—XA, —$CH_2$—CH(OA)—$R_9$ or

—$CH_2$—CH(OH)—$CH_2$—XA;

A is —C(=O)—$CR_5$=CH—$R_6$;

$R_2$, independently of one another, are H, $C_1$–$C_{12}$alkyl, $C_5$–$C_{12}$cycloalkyl, $C_3$–$C_6$alkenyl, halogen, phenyl or trifluoromethyl;

$R_2'$, independently of one another, are $C_1$–$C_{18}$alkoxy, $C_3$–$C_{18}$alkenoxy, —O—CO—$R_{12}$, —OH or —OA;

$R_3$ and $R_3'$, independently of one another, are H, —OH, —$OR_1$, —$OR_{131}$, $C_1$–$C_{18}$alkyl, $C_3$–$C_{18}$alkenyl, $C_6$–$C_{12}$cycloalkyl, halogen, trifluoromethyl, phenyl, phenyl-$C_1$–$C_4$alkyl, —CN, $C_1$–$C_{18}$alkyl-S(=O)$_t$— or phenyl-S(=O)$_t$—;

$R_4$, $R_4'$ and $R_4''$, independently of one another, are H, $C_1$–$C_{18}$alkyl, $C_3$–$C_6$alkenyl, —OR$_{131}$, halogen, trifluoromethyl, phenyl, phenyl-$C_1$–$C_4$alkyl, mono- to tri-$C_1$–$C_4$alkyl-substituted phenyl-$C_1$–$C_4$alkyl, —CN, $C_1$–$C_{18}$alkyl-S(=O)$_t$— or phenyl-S(=O)$_t$—;

$R_5$ is H, —CH$_2$—COOR$_{13}$, $C_1$–$C_4$alkyl or —CN;

$R_6$ is H, —COOR$_{13}$, $C_1$–$C_{17}$alkyl or phenyl;

$R_7$ is $C_1$–$C_{18}$alkyl, $C_5$–$C_{12}$cycloalkyl, $C_3$–$C_{18}$alkenyl; phenyl; phenyl which is substituted by one to three $C_1$–$C_8$alkyl, $C_1$–$C_8$alkoxy, $C_3$–$C_8$alkenoxy halogen or trifluoromethyl radicals; phenyl-$C_1$–$C_4$alkyl; $C_3$–$C_{50}$alkyl which is interrupted by —O—; 1-adamantyl; 2-adamantyl; norbornyl; 2-methylnorbornyl, —C(=O)—R$_{12}$ or —A;

$R_8$ and $R_8'$, independently of one another, are H; $C_1$–$C_{18}$alkyl; phenyl; phenyl which is substituted by one to three $C_1$–$C_8$alkyl, $C_1$–$C_8$alkoxy, $C_3$–$C_8$alkenoxy, halogen or trifluoromethyl radicals; or are phenyl-$C_1$–$C_4$ alkyl;

$R_9$ is $C_1$–$C_{18}$alkyl, phenyl or phenyl-$C_1$–$C_4$alkyl;

$R_{10}$ is H or —CH$_3$;

$R_{11}$ and $R_{11}'$, independently of one another, are $C_1$–$C_4$alkyl or phenyl or phenyl which is substituted by one to three $C_1$–$C_8$alkyl, $C_1$–$C_8$alkoxy, $C_3$–$C_8$alkenoxy, halogen or trifluoromethyl radicals;

$R_{12}$ is H, $C_1$–$C_{18}$alkyl, phenyl, phenyl-$C_1$–$C_4$alkyl, $C_5$–$C_{12}$cycloalkyl, $C_1$–$C_{12}$-alkoxy, phenoxy, norborn-2-yl, 5-norbornen-2-yl or 1-adamantyl;

$R_{13}$ is $C_1$–$C_{18}$alkyl; $C_3$–$C_{18}$alkenyl; phenyl; $C_5$–$C_{12}$cycloalkyl; $C_3$–$C_{50}$alkyl which is interrupted by —O—; phenyl which is substituted by one to three $C_1$–$C_8$alkyl, $C_1$–$C_8$alkoxy, $C_3$–$C_8$alkenoxy, halogen or trifluoromethyl radicals; phenyl-$C_1$–$C_4$alkyl; 2-adamantyl; norbornyl or 2-methylnorbornyl;

$R_{14}$ and $R_{15}$, independently of one another, are H, $C_1$–$C_{18}$alkyl, $C_3$–$C_{18}$alkenyl, $C_6$–$C_{12}$cycloalkyl, halogen, trifluormethyl, phenyl, phenyl-$C_1$–$C_4$-alkyl, —CN, $C_1$–$C_{18}$alkyl-(S=O)$_t$—, phenyl-(S=O)$_t$— or —OR$_{131}$;

$R_{131}$ is $C_1$–$C_{18}$alkyl; $C_1$–$C_{18}$alkyl which is substituted by —OH, $C_1$–$C_{18}$alkoxy, $C_5$–$C_{12}$cycloalkoxy, $C_3$–$C_6$alkenyloxy, halogen, —COOR$_{13}$, —CONH$_2$, —COHNR$_{132}$, —CON(R$_{132}$)(R$_{133}$), —NHCOR$_{12}$, —CN, —OCOR$_{12}$, phenoxy and/or by phenoxy which is substituted by $C_1$–$C_{18}$alkyl, $C_1$–$C_{18}$alkoxy or halogen; or is $C_3$–$C_{18}$alkenyl;

$C_6$–$C_{12}$cycloalkyl; $C_1$–$C_4$alkyl- and/or —OCOR$_{12}$-substituted $C_6$–$C_{12}$cycloalkyl; $C_3$–$C_{50}$alkyl which is interrupted by —O—; $C_3$–$C_{50}$alkyl which is interrupted by —O— and substituted by —OH or —O—CO—R$_{12}$; phenyl; phenyl-$C_1$–$C_4$alkyl; —COR$_{12}$ or —SO$_2$R$_{12}$;

$R_{132}$ and $R_{133}$, independently of one another, are $C_1$–$C_{12}$alkyl, $C_3$–$C_{12}$alkoxyalkyl, $C_4$–$C_{16}$dialkylaminoalkyl or $C_5$–$C_{12}$cycloalkyl; or $R_{132}$ and $R_{133}$ together are $C_3$–$C_9$alkylene, $C_3$–$C_9$oxaalkylene or -azaalkylene;

X is —NR$_8$, —O—, —NH—(C$_n$H$_{2n}$)—NH— or —O—(C$_k$H$_{2k}$)—NH;

k is a number from 2 to 4;

l is a number from 0 to 19;

m is a number from 2 to 8;

n is a number from 0 to 4;

p is a number from 0 to 10;

q is a number from 1 to 8;

r is a number from 0 to 18; and t is the number 0, 1 or 2.

15. A process for protecting photographic recording material comprising, on a base, a silver-halide emulsion layer or a silver-halide emulsion layer and additionally an interlayer and/or a protection layer against harmful effects of UV radiation, which process comprises incorporating a UV absorber of the formula I according to claim 14 or a homopolymer of the compound of the formula (I), a copolymer of different compounds of the formula (I) or a copolymer of a compound of the formula (I) and a further ethylenically unsaturated compound according to claim 1 into a layer of said material.

16. A process according to claim 15, wherein a homopolymer of a compound of the formula (I), a copolymer of different compounds of the formula (I) or a copolymer of a compound of the formula (I) and a further ethylenically unsaturated compound is incorporated.

17. A photographic recording material according to claim 1 comprising additionally a sterically hindered amine.

* * * * *